(12) United States Patent
Kelts et al.

(10) Patent No.: US 8,592,172 B2
(45) Date of Patent: *Nov. 26, 2013

(54) BIOLUMINESCENT ASSAYS USING CYANOBENZOTHIAZOLE COMPOUNDS

(75) Inventors: Jessica Kelts, Flint, MI (US); Poncho Meisenheimer, San Luis Obispo, CA (US); John Shultz, Verona, WI (US); James J. Cali, Verona, WI (US); Dongping Ma, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/046,374

(22) Filed: Mar. 11, 2011

(65) Prior Publication Data

US 2011/0223625 A1 Sep. 15, 2011

Related U.S. Application Data

(60) Provisional application No. 61/312,858, filed on Mar. 11, 2010.

(51) Int. Cl.
*C12Q 1/66* (2006.01)

(52) U.S. Cl.
USPC .................. 435/8; 435/7.2; 435/25; 435/7.4; 435/7.72

(58) Field of Classification Search
USPC ........................................ 435/7.72, 8, 7.4, 25
See application file for complete search history.

(56) References Cited

U.S. PATENT DOCUMENTS

| | | | |
|---|---|---|---|
| 5,424,440 | A | 6/1995 | Klem et al. |
| 6,376,208 | B1 | 4/2002 | Kajiyama |
| 7,122,303 | B2 | 10/2006 | Delenstarr et al. |
| 2003/0211560 | A1 | 11/2003 | O'Brien et al. |
| 2004/0171099 | A1 | 9/2004 | Cali et al. |
| 2004/0254120 | A1 | 12/2004 | Fogelman et al. |
| 2009/0148386 | A1 | 6/2009 | Mao et al. |
| 2010/0075351 | A1 | 3/2010 | Anderson et al. |

FOREIGN PATENT DOCUMENTS

| | | |
|---|---|---|
| EP | 1935986 | 6/2008 |
| WO | 2006/130551 | 12/2006 |
| WO | 2010/030343 | 3/2010 |
| WO | 2011/112966 | 9/2011 |

OTHER PUBLICATIONS

McCapra F. Accounts of Chemical Research (1976) 9(6): 201-208.*
European Patent Office Examination Report for Application No. 09789278.0 dated Apr. 19, 2012 (6 pages).
Niwa, K. et al., "Applications of luciferin biosynthesis: bioluminescence assays for 1-cysteine and luciferase," Anal. Biochem. (2010) 396(2):316-318.
International Search Report and Written Opinion for Application No. PCT/US2011/028147 dated May 25, 2011 (11 pages).
Becker, C.F.W. et al., "C-terminal fluorescence labeling of proteins for interaction studies on the single-molecule level," Chem. Bio. Chem. (2006) 7(6):891-895.
Carreras, C.W. et al., "A C-terminal conformational equilibrium in thymidylate synthase observed by electron paramagnetic resonance spectroscopy," Biochem. (1994) 33(8):2071-2077.
Chen, Q. et al., "Construction, properties and specific fluorescent labeling of a bovine prothrombin mutant engineered with a free C-terminal cysteine," Protein Engineering (1996) 9(6):545-553.
Dirksen, A. et al., "Strategy for the snthesis of multivalent peptide-based nonsymmetric dendrimers by native chemical litigation," Chem. Commun. (2006) 1667-1669.
Hong, S.-H. et al., "Domain-specific fluorescence resonance energy transfer (FRET) sensors of metallothionein/thionein," Protein Engineering Design and Section (2005) 18(6):255-263.
Kapanidis, A.N. et al., "Fluorescent probes and bioconjugation chemistries for single-molecule fluorescence analysis of biomolecules," J. Chem. Phys. (2002) 117(24):10953-10964.
Kushnir, S. et al., "Rapid production of functionalized recombinant proteins: marrying ligation independent cloning and in vitro protein litigation," Bioconjugate Chem. (2006) 17:610-617.
Monsees, T. et al., "Synthesis and characterization of a bioluminogenic substrate for alpha-chymotrypsin," Anal. Biochem. (1994) 221(2):329-334.
O'Brien, M.A. et al., "Homogeneous bioluminescent protease assays: caspase-3 as a model," J. Biomol. Screening (2005) 10(2):137-148.
Schuette, C.G. et al., "Determinants of liposome fusion mediated by synaptic SNARE proteins," Proc. Natl. Acad. Sci. USA (2004) 101(9):2858-2863.
Shinde, R. et al., "Luciferin derivatives for enhances in vitro and in vivo bioluminescence assays," Biochem. (2006) 45:11103-11112.
International Search Report and Written Opinion for Application No. PCT/US2009/005052 dated Jan. 29, 2010 (12 pages).
United States Patent Office Action for U.S. Appl. No. 12/556,505 dated Jul. 27, 2012 (11 pages).
European Patent Office Examination Report for Application No. 11709845.9 dated Oct. 19, 2012 (2 pages).
United States Patent Office Action for U.S. Appl. No. 12/556,505 dated Dec. 31, 2012 (9 pages).

* cited by examiner

*Primary Examiner* — Susan Hanley
(74) *Attorney, Agent, or Firm* — Michael Best & Friedrich LLP

(57) ABSTRACT

The invention provides methods that employ derivatives of 2-cyano-6-hydroxy- or 2-cyano-6-amino-benzothiazole, for example, in a bioluminogenic reaction. The invention further provides methods for detecting or determining the presence of molecules and/or enzymes, the modulator activity of such molecules, and/or the activity of such enzymes. The methods are adaptable to high-throughput format.

30 Claims, 34 Drawing Sheets

*LUCIFERIN*

PBI3138
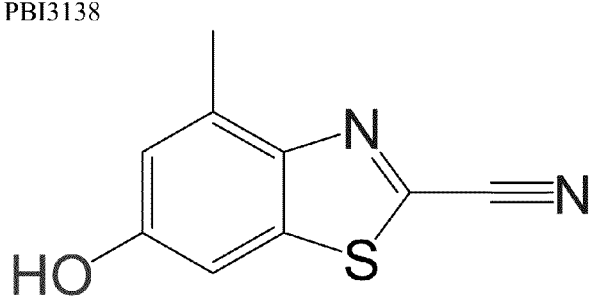
PBI3019
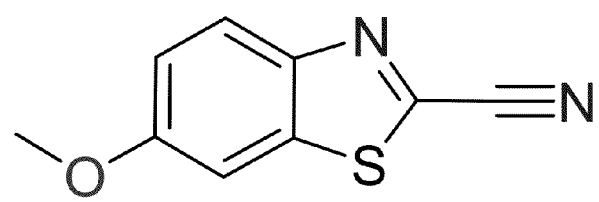
*FIG. 32*

| CYP Preferences: | 1A1, 1A2, 1B1, 2A6, 2B6 | 1A1, 1A2, 1B1, 2A6, 2B6 | 1A1, 1A2, 1B1 | 1A1, 1A2, 1B1 | 1A2, 4F12 | 1A2 | 1A2, 2I2, 2C19, 4F3B | 1A2, 4F3B | 1A1, 1A2, 1B1, 2C19 | 1A1, 1A2, 1B1, 2B6, 2C19 | 1A1, 1A2, 1B1, 2B6, 2C19, 4F3B | 1A1, 1A2, 1B1, 2B6, 2C19, 4F3B | 2A6 | 1A2, 2A6, 2E1 | 1A1, 1A2, 1B1, 2C19 |
|---|---|---|---|---|---|---|---|---|---|---|---|---|---|---|---|
| Compound: | PBI3019 | PBI3019 | PBI3806 | PBI3806 | PBI3835 | PBI3835 | PBI3883 | PBI3883 | PBI3868 | PBI3866 | PBI3821 | PBI3821 | PBI3819 | PBI3026 | PBI3868 |
| Substrate concentration: | 50μM | 6μM | 50μM | 2μM | 50μM | 10μM | 50μM | 7μM | 50μM | 50μM | 50μM | 3μM | 50μM | 50μM | 50μM |
| CYP concentration: | 20nM | 10nM | 20nM | 5nM | 20nM | 10nM | 20nM | 5nM | 20nM | 20nM | 20nM | 5nM | 20nM | 20nM | 20nM |
| CYP enzyme | Ave RLU | Ave | Ave | Ave | Ave | Ave | Ave | Ave | Ave | Ave | Ave | Ave | Ave | Ave | Ave |
| 1A1 | 1109043 | 119984 | 70386 | 5804 | 204190 | 14120 | 42112 | 2165 | 3441540 | 1076018 | 1903416 | 339726 | 672 | 1529 | 3441540 |
| 1A2 | 7064420 | 1067282 | 616746 | 67780 | 1010890 | 274495 | 490020 | 34890 | 353690 | 264188 | 626524 | 201329 | 926 | 35300 | 353690 |
| 1B1 | 173875 | 21208 | 106399 | 7080 | 233254 | 22527 | 22637 | 1907 | 229432 | 501833 | 940197 | 71298 | 223 | 338 | 229432 |
| 2A6 | 1512327 | 199263 | 3550 | 555 | 168697 | 16556 | 1681 | 1373 | 1339 | 17977 | 83086 | 4540 | 12507 | 200350 | 1339 |
| 2B6-b5 | 1607234 | 83207 | 6607 | 453 | 215355 | 16376 | 9565 | 1259 | 3763 | 852679 | 1959513 | 168844 | 225 | 559 | 3763 |
| 2B6+b5 | 1524786 | 109100 | 5348 | 537 | 221974 | 20131 | 10371 | 1259 | 3663 | 1163385 | 2113666 | 183633 | 235 | 669 | 3663 |
| 2C8-b5 | 813 | 296 | 7861 | 697 | 257432 | 18722 | 12123 | 1597 | 1530 | 10407 | 40032 | 2958 | 239 | 335 | 1530 |
| 2C8+b5 | 4759 | 321 | 7226 | 631 | 267558 | 19508 | 12985 | 1583 | 1490 | 13044 | 65414 | 3267 | 227 | 292 | 1490 |
| 2C9-b5 | 18341 | 1410 | 9703 | 773 | 293107 | 21640 | 14292 | 1763 | 2005 | 14968 | 54482 | 3759 | 177 | 320 | 2005 |
| 2C9+b5 | 111742 | 1785 | 11832 | 794 | 290116 | 26575 | 16435 | 1906 | 4789 | 31461 | 135073 | 5029 | 176 | 451 | 4789 |
| 2C18 | 181282 | 6432 | 37761 | 715 | 237977 | 21286 | 26931 | 1693 | 4051 | 20646 | 200191 | 8758 | 170 | 344 | 4051 |
| 2C19-b5 | 143482 | 2800 | 13116 | 836 | 419910 | 87631 | 35102 | 1715 | 61951 | 3844262 | 5400074 | 520979 | 217 | 595 | 61951 |
| 2C19+b5 | 370925 | 5841 | 29515 | 803 | 341630 | 41697 | 99989 | 2362 | 235920 | 6119885 | 8701002 | 756316 | 155 | 914 | 235920 |
| 2D6 | 441868 | 13674 | 24974 | 712 | 276378 | 25113 | 62029 | 1698 | 37100 | 41371 | 303132 | 17107 | 177 | 1157 | 37100 |
| 2E1 | 1293035 | 69702 | 4661 | 511 | 237692 | 20597 | 11506 | 1164 | 1645 | 13622 | 63747 | 3316 | 439 | 40637 | 1645 |
| 2J2 | 3946 | 300 | 5229 | 464 | 220582 | 15029 | 93644 | 2002 | 1939 | 17259 | 142561 | 6209 | 134 | 229 | 1939 |
| 3A4-b5 | 1707 | 208 | 3309 | 338 | 206522 | 19329 | 6222 | 781 | 896 | 6894 | 27561 | 1952 | 204 | 196 | 896 |
| 3A4+b5 | 25884 | 549 | 3527 | 328 | 285506 | 41618 | 7088 | 833 | 4289 | 14861 | 47935 | 2987 | 270 | 241 | 4289 |
| 3A5-b5 | 1602 | 233 | 4570 | 469 | 260309 | 20154 | 9571 | 1120 | 1055 | 7934 | 32461 | 2423 | 136 | 241 | 1055 |
| 3A5+b5 | 16711 | 458 | 4891 | 453 | 269281 | 29023 | 9213 | 1171 | 2017 | 10618 | 39472 | 2763 | 194 | 231 | 2017 |
| 3A7 | 2275 | 241 | 4763 | 449 | 242062 | 17477 | 8979 | 998 | 2973 | 9134 | 33691 | 2493 | 187 | 220 | 2973 |
| 4A11 | 15550 | 697 | 6672 | 613 | 242073 | 20323 | 12444 | 1456 | 4093 | 32100 | 118601 | 9122 | 133 | 259 | 4093 |
| 4F2 | 292645 | 11238 | 8146 | 625 | 351605 | 33406 | 12585 | 1523 | 1285 | 31113 | 375739 | 25129 | 107 | 403 | 1285 |
| 4F3A | 8630 | 519 | 6964 | 617 | 274083 | 20067 | 12101 | 1390 | 3279 | 17177 | 70227 | 4752 | 120 | 232 | 3279 |
| 4F3B | 536576 | 10134 | 7763 | 637 | 317266 | 25251 | 95387 | 2044 | 1098 | 241056 | 1522633 | 161251 | 115 | 603 | 1098 |
| 4F12 | 39399 | 1383 | 6758 | 475 | 404418 | 37943 | 9509 | 1053 | 1175 | 43521 | 257233 | 12019 | 105 | 188 | 1175 |
| 19 | 232225 | 7086 | 4985 | 472 | 254263 | 16540 | 9566 | 1095 | 2404 | 60903 | 105133 | 7952 | 107 | 349 | 2404 |
| control | 570 | 242 | 6471 | 431 | 260942 | 21526 | 9199 | 999 | 1429 | 7733 | 31520 | 2425 | 91 | 203 | 1429 |

FIG. 33A

| CYP Preferences: | 1A1, 1A2, 1B1, 2A6, 2B6, 2C19, 2E1 | 1A1 | 1A1, 3A4 | 1A1 | 1A1, 1A2, 1B1, 2A6, 2E1, 2C19, 3A4 | 1A1, 1B1, 2A6, 2E1 | 1A1, 1A2, 2B6 | 1A1, 1A2, 1B1, 2B6, 2C19, 2D6, 2E1 | 1A1, 1A2, 1B1, 2B6, 2C19, 2D6, 2E1, 4F3B | 1A1, 2C19, 3A4 | 1A1, 1A2, 1B1, 2C19, 3A4, 4F12, 19 | 3A4 | 3A4, 3A5 | 1A1, 1A2, 2C19, 19 | 1A1, 1A2, 2A6, 3A4 |
|---|---|---|---|---|---|---|---|---|---|---|---|---|---|---|---|
| Compound: | PBI3833 | PBI3823 | PBI3023 | PBI3016 | PBI3814 | PBI3814 | PBI3828 | PBI3820 | PBI3820 | PBI3017 | PBI3018 | PBI3020 | PBI3021 | PBI3022 | PBI3024 |
| Substrate concentration: | 50µM | 50µM | 50µM | 50µM | 50µM | 4µM | 50µM | 50µM | 50µM | 50µM | 50µM | 50µM | 50µM | 50µM | 50µM |
| CYP concentration: | 20nM | 20nM | 20nM | 20nM | 20nM | 5nM | 20nM | 20nM | 20nM | 20nM | 20nM | 20nM | 20nM | 20nM | 20nM |
| CYP enzyme | Ave | Ave | Ave | Ave | Ave | Ave | Ave | Ave | Ave | Ave | Ave | Ave | Ave | Ave | Ave |
| 1A1 | 10245375 | 30662 | 1399364 | 411302 | 20118137 | 894639 | 10362 | 1816132 | 131402 | 536197 | 1900440 | 64891 | 7160 | 2173487 | 339004 |
| 1A2 | 926313 | 1593 | 1130559 | 79819 | 1176674 | 53688 | 52780 | 4017546 | 472189 | 23073 | 758313 | 2995 | 2243 | 563790 | 219584 |
| 1B1 | 391498 | 1707 | 104274 | 51825 | 478153 | 18765 | 1525 | 1083153 | 52865 | 55697 | 807245 | 2257 | 1222 | 43675 | 50513 |
| 2A6 | 482399 | 2167 | 9528 | 26853 | 1795588 | 21806 | 13862 | 6516 | 2543 | 25511 | 7675 | 1015 | 6282 | 2047 | 207626 |
| 2B6-b5 | 176794 | 2442 | 46264 | 21262 | 226018 | 2496 | 132326 | 15954067 | 785055 | 35543 | 105041 | 18017 | 2467 | 21263 | 52658 |
| 2B6+b5 | 270265 | 2667 | 49660 | 21807 | 311558 | 3695 | 149132 | 15747820 | 1288652 | 38680 | 136713 | 22182 | 2493 | 29368 | 51892 |
| 2C8-b5 | 4801 | 1757 | 4962 | 27990 | 2583 | 196 | 876 | 18305 | 2974 | 35677 | 5390 | 3983 | 1459 | 2687 | 60505 |
| 2C8+b5 | 10284 | 1726 | 5254 | 27520 | 13668 | 219 | 943 | 289517 | 5368 | 91489 | 14364 | 12711 | 2265 | 6607 | 58763 |
| 2C9-b5 | 14162 | 1879 | 5798 | 32691 | 12168 | 203 | 1138 | 80429 | 3455 | 36315 | 13162 | 5394 | 1114 | 3593 | 72246 |
| 2C9+b5 | 68451 | 2120 | 6593 | 34213 | 84286 | 458 | 9003 | 406326 | 6574 | 42917 | 31400 | 26037 | 1555 | 7005 | 74177 |
| 2C18 | 14863 | 1723 | 8090 | 29681 | 14125 | 233 | 7519 | 71057 | 3511 | 51788 | 154880 | 17723 | 3744 | 120397 | 65948 |
| 2C19-b5 | 173124 | 3588 | 15024 | 28939 | 226892 | 1265 | 2391 | 1706076 | 59721 | 125014 | 505707 | 21003 | 1991 | 204803 | 59726 |
| 2C19+b5 | 450684 | 3537 | 52125 | 30531 | 638787 | 4241 | 4741 | 3817973 | 106422 | 332026 | 1385914 | 41624 | 3161 | 863988 | 64084 |
| 2D6 | 65640 | 1719 | 6262 | 21352 | 92332 | 979 | 1685 | 1480506 | 40916 | 25633 | 86231 | 5593 | 1349 | 9358 | 48418 |
| 2E1 | 960850 | 1902 | 11579 | 30783 | 1578272 | 8086 | 18661 | 241230 | 6787 | 23494 | 178138 | 921 | 2295 | 22863 | 49790 |
| 2J2 | 6086 | 1657 | 6904 | 22856 | 7452 | 143 | 657 | 3596170 | 81326 | 29297 | 49442 | 1477 | 1175 | 6101 | 47220 |
| 3A4-b5 | 19062 | 990 | 27584 | 19940 | 49967 | 119 | 522 | 51385 | 2314 | 47615 | 12887 | 64930 | 58989 | 4058 | 75078 |
| 3A4+b5 | 300111 | 1064 | 312920 | 30511 | 792669 | 1236 | 686 | 643806 | 17281 | 301626 | 120448 | 334484 | 627912 | 57220 | 888370 |
| 3A5-b5 | 26867 | 1290 | 11226 | 24655 | 83196 | 129 | 619 | 37749 | 2551 | 32869 | 7684 | 12936 | 212046 | 4070 | 55654 |
| 3A5+b5 | 237620 | 1279 | 86501 | 25064 | 999428 | 639 | 819 | 341647 | 8221 | 116116 | 47112 | 66780 | 1487207 | 37217 | 156993 |
| 3A7 | 17115 | 1303 | 16548 | 25541 | 32581 | 187 | 678 | 36959 | 3071 | 122611 | 8880 | 38476 | 13864 | 4677 | 87157 |
| 4A11 | 3061 | 1743 | 5234 | 30130 | 1675 | 156 | 913 | 210275 | 5860 | 32999 | 4792 | 1105 | 3385 | 2665 | 62566 |
| 4F2 | 3329 | 2579 | 5056 | 30110 | 2043 | 161 | 1114 | 424301 | 15627 | 31090 | 7286 | 930 | 1957 | 2410 | 60882 |
| 4F3A | 2861 | 1655 | 4752 | 28520 | 1487 | 139 | 718 | 35369 | 3669 | 31709 | 5129 | 1043 | 1583 | 2471 | 59568 |
| 4F3B | 4747 | 3079 | 5919 | 30392 | 3195 | 163 | 1991 | 856712 | 36466 | 32273 | 43383 | 1026 | 2042 | 2683 | 62728 |
| 4F12 | 77520 | 1874 | 104333 | 25676 | 111397 | 695 | 1489 | 405382 | 102217 | 26993 | 2135067 | 851 | 1412 | 6414 | 63314 |
| 19 | 68159 | 1379 | 5160 | 26009 | 59871 | 794 | 1243 | 41106 | 3536 | 63002 | 1020987 | 6020 | 161410 | 460165 | 62089 |
| control | 2433 | 1319 | 3945 | 24874 | 1141 | 122 | 651 | 6330 | 2351 | 27603 | 4274 | 2747 | 1163 | 2077 | 50544 |

FIG. 33B

| CYP Preferences: | 1A1, 1A2, 2A6, 2B6, 2C18, 2D6 | 1A1, 1A2, 2A6, 2C18, 2E1, 4F2, 4F3B | broad profile | 4F12 | 1A1, 1A2, 2A6, 2E1, 4F2, 4F3B | 4F2, 4F3B, 19 | 1A1, 1A2, 2A6, 2E1, 4F2, 4F3B, 19 | 1A1, 1A2, 1B1, 2A6, 2C18, 2C19, 2E1, 2J2 4F2, 4F3B, 19 | 1A2, 2A6, 2B6, 2E1 | 1A1, 1A2, 2A6, 2B6, 2C19, 2E1, 3A4, 19 | 1A1, 1A2, 1B1, 2A6, 2C19, 2B6, 2C19, 4F3B | 1A1, 1A2, 1B1, 2A6, 2C19, 2B6, 2C19, 2D6, 2J2, 4F3B | 1A1, 1A2, 2C19, 2D6 |
|---|---|---|---|---|---|---|---|---|---|---|---|---|---|
| Compound: | PBI3815 | PBI3817 | PBI3822 | PBI3822 | PBI3825 | PBI3826 | PBI3827 | PBI3829 | PBI3830 | PBI3851 | PBI3852 | PBI3891 | PBI3907 |
| Substrate concentration: | 50μM | 50μM quinolyl | 50μM | 50μM | 50μM | 50μM | 50μM | 50μM | 50μM | 50μM | 50μM | 50μM | 50μM |
| CYP concentration: | 20nM | 20nM | 20nM | 20nM | 20nM | 20nM | 20nM | 20nM | 20nM | 20nM | 20nM | 20nM | 20nM |
| CYP enzyme | Ave | Ave | Ave | Ave | Ave | Ave | Ave | Ave | Ave | Ave | Ave | Ave | Ave |
| 1A1 | 34697 | 24760 | 641365 | 421492 | 69864 | 2249 | 22300 | 5647833 | 52175 | 62516 | 1433379 | 798735 | 3412517 |
| 1A2 | 65310 | 43383 | 283783 | 119716 | 168369 | 1441 | 8739 | 1918000 | 583654 | 76918 | 368759 | 978220 | 4033284 |
| 1B1 | 9590 | 1926 | 231701 | 74821 | 7472 | 721 | 376 | 791709 | 3158 | 3062 | 576580 | 170382 | 485834 |
| 2A6 | 15165 | 14102 | 293710 | 89168 | 33492 | 3035 | 12429 | 1843229 | 125990 | 138626 | 14588 | 7090 | 19283 |
| 2B6-b5 | 33951 | 2677 | 1106097 | 13917 | 8719 | 1433 | 964 | 291202 | 435527 | 19853 | 1451170 | 2819443 | 176939 |
| 2B6+b5 | 46457 | 3834 | 466693 | 17787 | 11406 | 2380 | 1417 | 244114 | 559206 | 35082 | 1713789 | 3837521 | 364058 |
| 2C8-b5 | 207 | 249 | 209201 | 599 | 345 | 539 | 285 | 3784 | 347 | 4625 | 19897 | 28029 | 4875 |
| 2C8+b5 | 519 | 665 | 100466 | 2765 | 667 | 845 | 436 | 41047 | 1058 | 4690 | 35094 | 199067 | 37837 |
| 2C9-b5 | 525 | 1431 | 104850 | 581 | 333 | 597 | 326 | 16229 | 8566 | 1082 | 28059 | 72970 | 9618 |
| 2C9+b5 | 1335 | 2637 | 161330 | 4298 | 2727 | 555 | 1781 | 280492 | 46316 | 7708 | 63524 | 597586 | 36938 |
| 2C18 | 34679 | 7740 | 248285 | 3516 | 3049 | 859 | 319 | 1283922 | 38864 | 2241 | 57648 | 118374 | 37056 |
| 2C19-b5 | 2295 | 1145 | 229533 | 44385 | 2957 | 1937 | 318 | 917750 | 15632 | 11097 | 4685027 | 3455203 | 620854 |
| 2C19+b5 | 4010 | 1301 | 400033 | 150356 | 5672 | 2417 | 871 | 890751 | 41081 | 29369 | 5070204 | 4318554 | 937273 |
| 2D6 | 17967 | 2077 | 297438 | 2569 | 22399 | 1655 | 871 | 288214 | 12815 | 7965 | 155451 | 5841953 | 662715 |
| 2E1 | 3126 | 8218 | 320865 | 20083 | 69246 | 3587 | 8608 | 2450447 | 224356 | 36517 | 21700 | 462904 | 204290 |
| 2J2 | 149 | 155 | 305763 | 504 | 417 | 4904 | 204 | 1136326 | 529 | 407 | 55156 | 1669517 | 316769 |
| 3A4-b5 | 113 | 149 | 51944 | 1352 | 349 | 328 | 170 | 8580 | 239 | 2612 | 10510 | 54079 | 7504 |
| 3A4+b5 | 479 | 234 | 252892 | 18473 | 720 | 847 | 226 | 139580 | 1293 | 42681 | 14282 | 369465 | 73930 |
| 3A5-b5 | 117 | 168 | 48795 | 778 | 287 | 461 | 181 | 6912 | 275 | 761 | 13264 | 26357 | 3280 |
| 3A5+b5 | 519 | 259 | 202371 | 5059 | 448 | 639 | 238 | 69584 | 2421 | 2253 | 16801 | 169912 | 22328 |
| 3A7 | 111 | 149 | 78334 | 1963 | 353 | 589 | 164 | 5366 | 397 | 2483 | 14550 | 18915 | 6013 |
| 4A11 | 218 | 337 | 630298 | 807 | 1880 | 637 | 307 | 61951 | 474 | 792 | 61258 | 385786 | 31087 |
| 4F2 | 269 | 5730 | 214163 | 2134 | 37247 | 754859 | 3874 | 353620 | 6006 | 4552 | 172837 | 448474 | 122311 |
| 4F3A | 118 | 257 | 708375 | 457 | 891 | 8553 | 279 | 17019 | 251 | 457 | 32512 | 65604 | 15310 |
| 4F3B | 405 | 8376 | 229357 | 2025 | 78845 | 649579 | 12386 | 756643 | 8302 | 4406 | 963378 | 1260343 | 399756 |
| 4F12 | 194 | 1239 | 121785 | 3146692 | 662 | 4025 | 218 | 227638 | 5637 | 534 | 110491 | 146521 | 40032 |
| 19 | 6281 | 196 | 509950 | 465828 | 17165 | 76767 | 5532 | 146606 | 2165 | 45142 | 31819 | 50171 | 21180 |
| control | 89 | 144 | 61680 | 459 | 216 | 381 | 150 | 1854 | 105 | 479 | 13514 | 10110 | 1188 |

FIG. 33C

BIOLUMINESCENT ASSAYS USING CYANOBENZOTHIAZOLE COMPOUNDS

CROSS-REFERENCE TO RELATED APPLICATIONS

This application claims the benefit of U.S. Application Ser. No. 61/312,858, filed Mar. 11, 2010, which is incorporated by reference herein.

BACKGROUND

Luciferases can generate light via the oxidation of enzyme-specific substrates, e.g., luciferins. This provides the basis for assays directed at detecting the presence or level of luciferin in a sample. In one configuration, the luciferin detected is produced by a non-luciferase enzyme of interest converting a pro-luciferin substrate to a luciferin product. For firefly luciferase and all other beetle luciferases, light generation occurs in the presence of luciferin, magnesium ions, oxygen, and ATP. For anthozoan luciferases, including *Renilla* luciferase, only oxygen is required along with the substrate coelenterazine. Resultant bioluminescence, if any, is then measured using a luminometer or any suitable radiant energy-measuring device.

Beetle luciferase substrates, e.g., luciferin, contain a carboxylic acid group that is necessary for the efficient production of light. However, a variety of enzymes do not utilize substrates having a carboxylic acid group near the reaction site (e.g. CYP2D6) making assay of these enzymes very difficult using substrates containing a carboxylic acid group. For in vitro assays/reactions, this problem can be overcome by esterifying the carboxylic acid group, thus neutralizing its charge, on the substrate. However, this increases the size of the substrate, and thus may prevent its entry to the active site of the enzyme of interest resulting in a compound that is an ineffective substrate for the enzyme of interest.

Even if the esterification of a substrate does produce a substrate which can be used effectively by an enzyme of interest in an in vitro assay, such a substrate may not work in cell-based assays, e.g., live cells, as esterases present in the cell rapidly cleave esters thereby releasing the carboxylic acid form of the substrate which, as mentioned above, may not be an acceptable form of substrate for the enzyme of interest.

In the present invention, a new form of substrate, i.e., a derivative of 2-cyano-6-substituted benzothiazole, is disclosed for use in cell-based assays for the detection or measurement of an enzyme(s) of interest, i.e. non-luciferase enzyme(s). The substrates in the present invention do not contain the carboxylic acid group normally found on known luciferin substrates, but instead are precursors of luciferin analogs that can be rapidly and quantitatively transformed to luciferins by addition of D-Cysteine. In this way, the substrates of the present invention are smaller in size than those of the corresponding luciferin analogs yet do not have the negatively charged group found in know luciferins. The present invention also provides methods of using the substrates of the present invention in cell-based assays to detect or measure non-luciferase enzymes of interest.

SUMMARY OF THE INVENTION

The invention provides methods for performing a cell-based assay for enzymes of interest using derivatives of 2-cyano-6-substituted benzothiazoles. In one aspect, the invention provides a method of detecting a non-luciferase enzyme in a cell comprising contacting cells with a substrate for the enzyme, the substrate being a derivative of a 2-cyano-6-substituted benzothiazole under conditions which allow for a reaction between the enzyme and the substrate; adding a luciferase reaction mixture to the contacted cells; and measuring bioluminescence. Conditions that allow for the reaction between various enzymes (e.g. cytochrome P450s, UDP glucuronosyl transferases, glutathione transferases, proteases) and substrate are present in cells cultured according to standard methods well known to those skilled in the art. However, it is understood that medias or buffered salt solutions in which the 2-cyano-6-substituted benzothiazoles are applied to cells are free of cysteine. Cysteine free application solutions are necessary to avoid cyclization of the derivatives in solution with cysteine prior to exposure to the enzymes of interest.

In another aspect, the invention provides a method of detecting a non-luciferase enzyme in a cell comprising contacting cells with a substrate for the non-luciferase enzyme, the substrate being a derivative of a 2-cyano-6-substituted benzothiazole, under conditions which allow for a reaction between the enzyme and the substrate, in a first reaction vessel to form an incubation mixture; transferring at least a portion of the incubation mixture to a second reaction vessel; adding a luciferase reaction mixture to the second reaction vessel; and measuring bioluminescence.

In one aspect, the invention provides a method of screening for modulators of a non-luciferase enzyme comprising contacting cells with a test compound; adding a substrate for the non-luciferase enzyme, the substrate being a derivative of a 2-cyano-6-substituted benzothiazole, under conditions which allow for a reaction between the substrate and the non-luciferase enzyme, to form a mixture; adding a luciferase reaction mixture to the mixture; and measuring bioluminescence.

In another aspect, the invention provides a method of detecting more than one non-luciferase enzyme in a cell comprising contacting cells with two bioluminogenic substrates, one of the substrates being a derivative of 2-cyano-6-substituted benzothiazole, under conditions which allow a reaction between the enzymes and substrates, in a first reaction vessel; transferring a portion of the incubation mixture to a second and third reaction vessel; adding to one of the reaction vessels a luciferase reaction mixture comprising D-cysteine and adding to the other reaction vessel a luciferase reaction mixture without D-cysteine; and measuring bioluminescence in both reaction vessels.

The use of luciferin precursor substrates as described in the present invention for the assay of non-luciferase enzymes in a cell-based assay, e.g., in live mammalian cells, or complex biological solutions is new and novel. It was thought that the use of such substrates in a cell-based assay or complex biological solution would fail due to any of a number of factors, including;

1. Transformation of the precursor substrate to luciferin by the L-cysteine present in the cell, thus producing an inactive form of the substrate, 2. Transformation of a substantial amount of the enzyme product to luciferin by the L-cysteine present in the cell, thus transforming the substrate into a form of luciferin not utilized by luciferase. Luciferases which utilize luciferin require the stereoisomeric form produced with D-cysteine.

3. Alteration of the precursor substrate to a new chemical form that would no longer be able to be converted to a suitable luciferin through reaction of the cyano group to some other chemical form either by direct interaction with a compound(s) present in the cell or through the action of one of the many enzymes present in the cell.

4. Trapping of the substrate in the membranes of the cell due to the lack of a charge from the carboxylate group normally found on luciferin, and 5. Discovery that the cyano group on the substrates for the present invention may cause a rapid lysis of the cell due to some toxic effect it may invoke on a cell.

BRIEF DESCRIPTION OF THE DRAWINGS

FIG. 32 illustrates the structures of PBI3019 and PBI3138.

FIG. 33 illustrates data for various derivatives.

DETAILED DESCRIPTION OF THE INVENTION

Definitions

Figure 1:
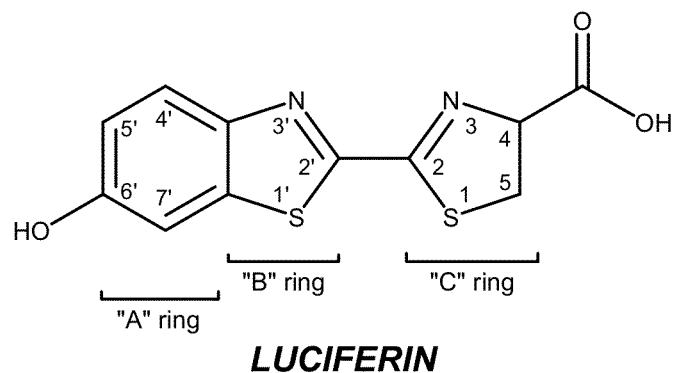
FIG. 1 illustrates the numbering of ring atoms in native firefly luciferin: the six membered "benzo" ring ("A ring"), five membered thiazole ring ("B ring"), and the five membered thiazolyl ring ("C ring").

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some aspects 1, 2, or 3; and in other aspects 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable substituents include, e.g., deuteron, alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, the suitable substituents can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O$^-$, —S(=O)$_2$OH, —S(=O)$_2$R, —OS(=O)$_2$OR, —S(=O)$_2$NR, —S(=O)R, —OP(=O) O$_2$RR, —P(=O)O$_2$RR —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S) NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

As used herein, the term "lower" refers to a carbon chain having no more than 4 carbon atoms.

The term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, $sp^2$ double bond). In one aspect, an alkenyl group can have from 2 to 10 carbon atoms, or 2 to 6 carbon atoms. In another aspect, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one aspect, the alkynyl group can have from 2 to 10 carbon atoms, or 2 to 6 carbon atoms. In another aspect, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one aspect, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one aspect, the haloalkyl can be substituted with 1, 2, 3, 4, or 5 halo groups. In another aspect, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one aspect the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In another aspect heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In one aspect, "heterocycle" includes a "carbocycle" as defined herein, wherein one or more (e.g., 1, 2, 3, or 4) carbon atoms have been replaced with a heteroatom (e.g., O, N, or S).

Examples of heterocycles, by way of example and not limitation, include, without limitation, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1, 2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one aspect, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted". The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The term "amino acid," includes a residue of a natural amino acid (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M., *Protecting Groups In Organic Synthesis*, 2$^{nd}$ edition, John Wiley & Sons, Inc., New York (1991) and references cited therein).

The term "peptide" describes a sequence of 2 to 35 amino acids (e.g., as defined herein above) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids or 2 to 5 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "saccharide" refers to a sugar or other carbohydrate, especially a simple sugar. The saccharide can be a $C_6$-polyhydroxy compound, typically $C_6$-pentahydroxy, and often a cyclic glycal. The term includes the known simple sugars and their derivatives, as well as polysaccharides with two or more monosaccharide residues. The saccharide can include protecting groups on the hydroxyl groups, as described above in the definition of amino acids. The hydroxyl groups of the saccharide can be replaced with one or more halo or amino groups. Additionally, one or more of the carbon atoms can be oxidized, e.g., to keto or carboxyl groups.

The term "interrupted" indicates that another group is inserted between two adjacent carbon atoms (and the hydrogen atoms to which they are attached (e.g., methyl ($CH_3$), methylene ($CH_2$) or methine (CH)) of a particular carbon chain being referred to in the expression using the term "interrupted", provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one ore more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

The term "luciferase," unless specified otherwise, refers to a naturally occurring or mutant luciferase. The luciferase, if naturally occurring, may be obtained easily by the skilled artisan from an organism. Luciferases which utilize luciferin as a substrate, luciferin-utilizing luciferases, are preferred. If the luciferase is one that occurs naturally or is a mutant, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding the same. Luciferases are available from Promega Corporation (Madison, Wis.). Preferred examples are firefly luciferases including those from *Photinus pyralis, Photuris pennsylvanica*, and stabilized mutant forms of the same.

The term "LDR" as used herein refers to a solution known as "Luciferin Detection Reagent". It is generated by dissolving a Luciferin Detection Reagent (Promega Corporation part no. V859) [0.6% Prionex®, 0.1 mg/ml Thermostable Ultra-Glo™ Recombinant Luciferase, 0.4 mM ATP, 2 U/ml Inorganic Pyrophosphatase, 0.2M PIPES pH 6.7, 12 mM MgSO4, 1 mM CDTA, 18 uM 2-(4-Aminophenyl)-6-methylbenzothiazole (APMBT), 2% Tergitol, 0.2% DTAB, 0.2% Mazu, and 20 U/ml Porcine Esterase] with a Reconstitution Buffer (Promega Corporation part no. V865).

The "cyano" group may be depicted as —CN or —C≡N or —≡N.

METHODS OF THE INVENTION

The invention provides methods for performing cell-based assays for enzymes of interest using derivatives of 2-cyano-6-hydroxybenzothiazole or 2-cyano-6-aminobenzothiazole (derivatives of "2-cyano-6-substituted benzothiazole" hereinafter). Generally, the cell-based assays are performed using 2-cyano-6-substituted benzothiazole derivatives having a particular enzyme recognition site for a desired non-luciferase enzyme coupled to the 2-cyano-6-substituted benzothiazole backbone (a substrate), e.g., coupled to the 6'-hydroxy site or a 6'-amino site. The cell is contacted with the substrate. The resulting mixture is then contacted with a luciferase reaction mixture and bioluminescence is measured. In one aspect, D-cysteine is added concurrently with the substrate. In another aspect, D-cysteine is added to the mixture prior to or concurrently with the luciferase reaction mixture. Alternatively, D-cysteine may be present in the luciferase reaction mixture. In some embodiments, D-cysteine may be added at more than one time.

While 2-cyano-6-hydroxybenzothiazole or 2-cyano-6-aminobenzothiazole do not react with luciferase to generate light, both compounds readily cyclize with D-cysteine to form 2-(6-hydroxybenzo[d]thiazol-2-yl)-2,5-dihydrothiazole-4-carboxylic acid (D-luciferin) or 2-(6-aminobenzo[d]thiazol-2-yl)-2,5-dihydrothiazole-4-carboxylic acid (aminoluciferin), respectively, which do generate light when reacted with luciferase, e.g., at thermostable firefly luciferase. The assays can be performed at a pH of 4-9 with 1-100 μM derivative. Numerous non-luciferase enzymes may be detected and/or their activity measured in a bioluminescent assay using these derivatives.

The luciferase reaction mixture comprises a luciferase, $Mg^{2+}$ and ATP. The luciferase reaction mixture may also include other components such as D-cysteine, detergents, esterases, salts, etc. An example luciferase reaction mixture would contain a thermostable firefly luciferase, $MgSO_4$, ATP, Tergitol NP-9, and Tricine.

The bioluminescence generated may be compared to a control. Suitable controls lack one or more of the necessary components or conditions for either the reaction between the substrate and the non-luciferase enzyme or the luciferase reaction. Such components or conditions include, but are not limited to, co-factors, enzyme, temperature, and inhibitors.

Also provided is a method to identify a modulator of a non-luciferase enzyme-mediated reaction. The method includes contacting a cell with one or more test compounds and a substrate for the non-luciferase enzyme, the substrate being a derivative of 2-cyano-6-substituted benzothiazole. The resulting mixture is then contacted with a luciferase reaction mixture. In one aspect, D-cysteine is added concurrently with the substrate. In another aspect, D-cysteine is added to the mixture prior to or concurrently with the luciferase reaction mixture. Alternatively, D-cysteine may be present in the luciferase reaction mixture. In some embodiments, D-cysteine may be added at more than one time.

In addition, the methods provided herein may be used, for example, to detect at least one molecule, e.g., an enzyme, an enzyme regulator, an enzyme substrate, an enzyme activator, a cofactors for an enzymatic reaction (e.g., ATP), an OH radical or one or more conditions, e.g., redox conditions. In one aspect, the methods according to the present invention provide a rapid method for detecting one or more molecules in a single sample.

In another aspect, the method includes quantifying the presence, amount or specific activity of a molecule such as an enzyme, substrate or cofactor in a bioluminogenic assay. The intensity of the bioluminogenic signal is a function of the presence or amount of the respective molecule. In one aspect, the method employs at least two different reactions. For example, the first reaction may be a non-luciferase enzyme-mediated reaction and the second reaction may be a luciferase-mediated reaction. Alternatively, the first reaction is a nonenzymatic reaction and the second reaction is a luciferase-mediated reaction.

For the bioluminogenic assays described herein which employ derivatives with a lower bioluminescent background, those assays can use lower (or higher) amounts of the derivative, and those derivatives may have improved reactivity, e.g., with a non-luciferase enzyme. In addition, for any of the bioluminogenic assays described herein, other reagents may be added to the reaction mixtures, including, but not limited to, those that inhibit or prevent inactivation of luciferase or otherwise extend or enhance bioluminescent signal.

In another aspect of the invention, test compounds can be screened and evaluated for their activities as substrates, cofactors, regulators (either inhibitors or activators) or inducers of an enzymatic or nonenzymatic reaction by using the 2-cyano-6-substituted benzothiazole derivatives. For example, a test compound may be determined to be regulator or a substrate of a reaction by contacting a reaction mixture with a derivative and the test compound, under conditions that would, in the absence of the test compound, yield bioluminescence, or a bioluminogenic product.

In one aspect of the invention, a method is provided to distinguish between a substrate and an inhibitor of a reaction. For example, the test compound is incubated with at least one enzyme under conditions which allow for metabolism of the test compound prior to providing a 2-cyano-6-substituted benzothiazole derivative under conditions that, in the absence of an inhibitor or substrate of the enzyme, would be suitable for interaction between the derivative and the enzyme. In one aspect, the product of that reaction can be converted to D-luciferin or D-aminoluciferin and, in the presence of luciferase, yields a light-emitting second reaction. The resulting light-emitting reaction is compared to the one obtained from contacting the enzyme with the compound and the derivative, under conditions that would, in the absence of an inhibitor of the enzyme, be suitable for interaction between the derivative and the enzyme. Metabolism of the compound by the enzyme reduces its concentration in the assay medium and may lead to an apparent loss of inhibitory activity compared to conditions without metabolism of the compound which would indicate it was a substrate for the enzyme. An inhibitory compound that was not metabolized would show equal potency, irrespective of the time of addition of the substrate.

In one aspect of the invention, the test compound is preferably contacted first with the enzyme for a first predetermined time period, e.g., 24-48 hours. Thereafter, the mixture is contacted with a 2-cyano-6-substituted benzothiazole derivative and bioluminescent enzyme, e.g., luciferase, simultaneously or contemporaneously, and the mixture is allowed to incubate for a second predetermined time period.

In another aspect of the invention, a cell-based method is provided for screening a test compound(s) to determine its effect on enzyme activity of a cell. The test compound(s), for example an inhibitor of the non-luciferase enzyme, an inducer for the non-luciferase enzyme, a substrate for the non-luciferase enzyme, and an activator of the non-luciferase enzyme, is contacted with a cell expressing the enzyme, either naturally or via recombinant expression, the 2-cyano-6-substituted benzothiazole derivative, and a bioluminescent enzyme, e.g., luciferase, or contacted with a cell expressing the enzyme and a bioluminescent enzyme, and the 2-cyano-6-substituted benzothiazole derivative, for a predetermined period of time. Thus, a cell that either transiently or stably expresses a recombinant enzyme such as a bioluminescent enzyme, e.g., luciferase, may be employed. Any conventional method for creating transient or stable transfected cells may be used, e.g. those described in Sambrook et al. Molecular Cloning: A Laboratory Manual. In one aspect, a 2-cyano-6-substituted benzothiazole derivative is contacted with and diffuses into a cell and, if the appropriate molecule is present, yields a product, which is a substrate for luciferase. If a luciferase is present in the cell, bioluminescence can be detected. Alternatively, in a cell which lacks luciferase, the product may pass out of the cell into the medium wherein a luciferase reaction mixture can be added to the medium. Thereafter, the activity resulting from the interaction of the cell with the compound can be determined by measuring bioluminescence of the reaction mixture relative to a control (e.g., minus a test compound) reaction mixture.

In another aspect of the invention, the test compound(s) is preferably contacted first with the cell for a predetermined time period. Thereafter, the cell is contacted with the 2-cyano-6-substituted benzothiazole derivative and luciferase, either simultaneously or contemporaneously, and the mixture allowed to incubate for a second predetermined time period. Non-luciferase enzyme activity can be determined by measuring the amount of bioluminescence generated from the reaction mixture relative to a control reaction mixture (e.g., minus test compound(s)). In another aspect of the invention, the test compound(s) is preferably contacted first with the cell for a predetermined time period. Thereafter, the exposed cell is then contacted with the 2-cyano-6-substituted benzothiazole derivative and incubated for a second predetermined time period. The cell is then contacted with luciferase to form a third mixture which is allowed to incubate for a third predetermined time period. Thereafter, the activity of the cell resulting from the interaction of the cell with the test compound(s) can be determined by measuring bioluminescence of the reaction mixture relative to a control reaction mixture (e.g., minus test compound(s)). A cell-based bioluminescence detection assay for molecules present in the cell medium, e.g., molecules which actively or via inactive mechanisms are present in the cell medium, can include adding a reaction mixture with the 2-cyano-6-substituted benzothiazole derivative to the cell medium or adding the cell medium to a reaction mixture with the 2-cyano-6-substituted benzothiazole derivative, and detecting bioluminescence.

In yet another aspect of the cell-based assay of the invention, the cells may be lysed prior to adding a luciferin reaction mixture. For animal cells, a buffer with 0.1-1.0% non-ionic detergents such as Triton X-100 or Tergitol is typically sufficient. Bacteria, plant, fungal or yeast cells are usually more difficult to lyse. Detergents, freeze/thaw cycles, hypotonic buffers, sonication, cavitation or combinations of these methods may be used. The method of lysis that produces a lysate that is compatible with luciferase or other enzyme activity, or the detection of other molecules or conditions is preferred.

The presence or activity of non-luciferase enzymes may be measured in cells grown in culture medium or in cells within animals, e.g., living animals. For research purposes, for measurements in cells in animals, a 2-cyano-6-substituted benzothiazole derivative may be administered to the animal, e.g., injected into the animal or added to an aqueous solution, e.g., water, or food consumed by the animal. Conversion of the derivative to a product that is a luciferase substrate may be detected by bioluminescence mediated by luciferase expressed in cells in the animal, e.g., whole animal imaging of a transgenic animal (e.g., mice, rats, and marmoset monkeys) by luciferase administered to the animal, e.g., injected into the animal, or by collecting physiological fluids, e.g., blood, plasma, urine, and the like, or tissue samples, and combining those with a luciferase reagent.

Assays which employ two reactions may be conducted simultaneously (one step) or sequentially (two step) to detect one or more factors including proteins (peptides or polypeptides), e.g., enzymes, substrates, cofactors, inhibitors or activators for enzymatic reactions, or conditions, e.g., redox conditions. A sequential reaction may be conducted in the same vessel, e.g., a well of a multiwell plate, or different vessels. For a two step assay, the first reaction mixture may contain all of the reagents or less than all of the reagents for a non-luciferase enzyme-mediated reaction, where when one of the reagents is absent, it is the one to be detected in a sample, e.g., a cell lysate.

For instance, a non-luciferase enzyme-mediated reaction is performed under conditions effective to convert a 2-cyano-6-substituted benzothiazole derivative that is a substrate for the non-luciferase to a product that can be converted to D-luciferin or D-aminoluciferin. Conditions that allow for the reaction between various enzymes (e.g. cytochrome P450s, UDP glucuronosyl transferases, glutathione transferases, proteases) and substrate are present in cells cultured according to standard methods well known to those skilled in the art. However, it is understood that media or buffered salt solutions in which the 2-cyano-6-substituted benzothiazoles are applied to cells are free of cysteine. Cysteine-free application solutions are necessary to avoid cyclization of the derivatives in solution with cysteine prior to exposure to the enzymes of interest.

The first reaction may be quenched at the time, or prior to addition, of a luciferase reaction mixture. For instance, a quencher, e.g., a detergent, of the first reaction may be present in the luciferase reaction mixture. The luciferase reaction mixture preferably substantially lacks a substrate for the luciferase, e.g., the only source of substrate for the luciferase is provided by a reaction between the non-luciferase enzyme and the derivative. When all the reagents for the first reaction are present in the first reaction mixture, the assay may be employed to identify moieties that alter the reaction, e.g., inhibitors or enhancers of the reaction. After performing the reactions, either simultaneously or sequentially, the presence or amount of one or more molecules, or one or more inhibitors or activators of the reaction(s) is/are detected or determined and/or to what extent and with what potency.

For a one step assay, a reaction mixture may contain reagents for two reactions, such as reagents for a non-luciferase enzyme-mediated reaction and a luciferase-mediated reaction or for a nonenzymatic reaction and a luciferase-mediated reaction, or a reaction mixture for a single reaction.

For assays which employ two reactions, the order of adding the molecules for the assays can vary. If initiated and conducted sequentially (whether in the same vessel or not), adjustments to reaction conditions, e.g., reagent concentration, temperatures or additional reagents, may be performed. For instance, a quenching agent or enhancing agent may be added between reactions (see, e.g., U.S. Pat. Nos. 5,744,320 (Sherf et al.) and 6,586,196 (Bronstein et al.), the disclosures of which are specifically incorporated by reference herein). In one aspect, the two or more reactions are carried out simultaneously in a single reaction mixture. Optionally, the assays are a homogeneous assay, e.g., the components are mixed prior to adding the mixture to the sample. Results may be read without additional transfer of reagents.

The assays of the present invention thus allow the detection of one or more molecules or conditions in a sample, e.g., a sample which includes eukaryotic isolated or lysed cells, e.g., yeast, avian, plant, insect or mammalian cells including but not limited to human, simian, murine, canine, bovine, equine, feline, ovine, caprine or swine cells, e.g., human or rat hepocytes (ex. HepG2 cells), or prokaryotic cells, or cells from two or more different organisms, or cell lysates or supernatants thereof, or a sample which includes a purified form of the molecule, e.g., purified non-luciferase enzyme which is useful to prepare a standard curve. In other aspects, the sample can be a tissue explant, such as liver slices, brain slices, skin, etc. The cells may not have been genetically modified via recombinant techniques (non-recombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule.

The present methods can be employed to detect a molecule for an enzyme-mediated reaction, a non-enzymatic-mediated reaction or condition. For instance, molecules or conditions to be detected by the method include but are not limited to enzymes, e.g., demethylases, oxidases (e.g., a MAO), deacetylases, deformylases, proteases (proteosome, calpain, beta-secretase, cathepsin, calpain, thrombin, granzyme B), phosphatases, kinases, peroxidases, transferases, e.g., GST or UGT, sulfotases, beta-lactamases, cytochrome P450 enzymes, esterase, e.g., acetylcholinesterase, dehydrogenase, substrates, inhibitors, co-factors, activators of enzyme mediated reactions, reactive oxygen species, reducing conditions and transcriptional regulators or regulators of gene transcription. The non-luciferase enzymes employed in the methods, either enzymes to be detected or enzymes which are useful to detect a substrate or cofactor, can be selected from any combination of enzymes including recombinant and endogenous (native) enzymes. In one aspect, the non-luciferase enzyme to be detected is an endogenous enzyme. In another aspect, the non-luciferase enzyme is a recombinant enzyme. Other combinations apparent to one of ordinary skill in the art can be used in the present assays and methods according to the teachings herein. The non-luciferase enzymes include but are not limited to proteases, phosphatases, peroxidases, sulfatases, peptidases, oxidases, dealkylases, deformylases, transferases, and glycosidases. The non-luciferase enzyme may be a hydrolase, oxidoreductase, lyase, transferase, e.g., glutathione S transferase or UDP glucuronosyltransferase, isomerase, ligase, synthase, or a deacetylase, e.g. histone deacetylase (HDAC). Of particular interest are classes of non-luciferase enzymes that have physiological significance. These enzymes include protein peptidases, esterases, protein phosphatases, glycosylases, proteases, dehydrogenases, oxidases, oxygenases, reductases, methylases, transferases and the like. Non-luciferase enzymes of interest include those involved in making or hydrolyzing esters, both organic and inorganic, glycosylating, and hydrolyzing amides. In any class, there may be further subdivisions.

In particular, non-luciferase enzymes that are useful in the present invention include any protein that exhibits enzymatic activity, e.g., lipases, phospholipases, sulphatases, ureases, peptidases, proteases and esterases, including acid phosphatases, glucosidases, glucuronidases, galactosidases, and carboxylesterases. In one aspect, the non-luciferase enzyme is a hydrolytic enzyme. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, and β-D-glucosiduronase.

In one aspect, the assay is useful to detect non-luciferase enzymes, including cytochrome P450 enzymes (CYP450) enzymes or monoamine oxidases (MAOs), N-acetyl transferases (NATs), flavin monoamine oxidases (FMOs), glutathione S transferases (GSTs), phosphatases, e.g., alkaline phosphatases (AP), sulfatases, or UDP-glucuronosyl transferase (UGT). For instance, the assay may be performed using a substrate for a reductase, such as a cytochrome P450 reductase, MAO, FMO, GST, dealkylase, deacetylase, deformylase, phosphatase, e.g., AP, sulfatase, beta-lactamase, alcohol dehydrogenase, protease, e.g., proteosome, cathepsin, calpain, beta secretase, thrombin, or granzyme, luciferase, or the assay may be used to detect reactive oxygen species (ROS), peroxidase, e.g., horseradish peroxidase (HRP), and/or redox conditions. In another aspect, the assay may be performed using a substrate having at least a B ring modification which is useful to detect dealkylases, GST or luciferase, redox conditions, or UGT enzymes, or modulation (e.g., inhibition, or activation) of their activity.

In one aspect, the assay is useful for detecting more than one non-luciferase enzyme in a sample. For instance, the assay may be performed to detect two different enzymes in an enzyme class, e.g., two cytochrome P450 enzymes, CYP1A2 and CYP3A4, in a single sample. In such an assay, two different bioluminogenic substrates are added to a sample, wherein one of the bioluminogenic substrates is a 2-cyano-6-substituted benzothiazole derivative for one of the enzymes, e.g., CYP1A2, while the other bioluminogenic substrate could be a derivative of D-luciferin or aminoluciferin, e.g., a luciferin acetal, for the other enzyme, e.g., CYP3A4. In another aspect, the assay may be performed to detect two different non-luciferase enzymes, e.g., a CYP450 enzyme and a UGT enzyme. In this assay, two different bioluminogenic substrates are added to a sample, wherein one of the bioluminogenic substrates is a 2-cyano-6-substituted benzothiazole derivative for one of the enzymes, e.g., CYP1A2, while the other bioluminogenic substrate could be a derivative of D-luciferin or aminoluciferin for the other enzyme, e.g., UGT. For these multiplex assays, bioluminescence is measured by transferring a portion of the reaction into two different reaction vessels. To one of the reaction vessels, a luciferase reaction mixture containing D-cysteine is added to allow detection of the non-luciferase enzyme detected using the 2-cyano-6-substituted benzothiazole derivative. To the other reaction vessel, a luciferase reaction mixture without D-cysteine is added to allow detection of the non-luciferase enzyme detected using the other bioluminogenic substrate. In addition, a test compound, e.g., drug, could be added to the sample. The multiplex cell-based assay of the present invention could then be used to determine the effect of the test compound on more than one non-luciferase enzymes, e.g., two different enzymes in an enzyme class, simultaneously.

With respect to the methods described above, some aspects provide a first mixture that includes a product produced by a reaction between the non-luciferase enzyme and the derivative, wherein the product, in the presence of cysteine, is a bioluminogenic substrate for a luciferase. The invention also provides reciprocal methods wherein a first mixture includes a product produced by a reaction between the non-luciferase enzyme and the derivative, wherein the product, in the presence of cysteine, is a not bioluminogenic substrate for a luciferase. For example, in various aspects, a non-luciferase enzyme can consume a luciferase pro-substrate (e.g., the derivative), rather than generate a luciferase substrate. By comparing the test reaction to a control, the method provides the ability to detect or determine enzyme activity, or to determine the activity of a modulator for enzyme activity.

Cytochrome P450 Assays

In one aspect, the present invention provides a cell-based assay for cytochrome P450 (CYP450). A bioluminescent detection method is used that couples a CYP450 reaction with a light generating firefly luciferase reaction. In one aspect, in a first enzymatic reaction, a CYP450 enzyme oxidizes a cyanobenzothiazole derivative to 2-cyano-6-hydroxybenzothiazole, a precursor of D-(−)-2-(6'-hydroxy-2'-benzothiazolyl)-2-thiazolin-4-carboxylic acid (D-luciferin) a light-generating substrate of firefly luciferase. The CYP450 reaction products are converted to D-luciferin in a non-enzymatic cyclization reaction with cysteine and detected in a second enzymatic reaction with firefly luciferase. Derivativizations are such that, without prior oxidation by a CYP450 enzyme, the cysteine reaction produces a luciferin derivative that cannot produce light with luciferase. Therefore, light output from the system depends on and is proportional to CYP450-dependent transformation of the cyanobenzothiazole derivative to the luciferin precursor 2-cyano-6-hydroxy-benzothiazole. A variation on this approach starts with 2-cyano-6-aminobenzothiazole derivatives that are converted to D-aminoluciferin, which is also a light generating substrate of firefly luciferase.

UDP glucuronosyl transfer enzymes (UGTs) can conjugate the reaction product of a CYP450 reaction, and thereby can interfere with the assay. Thus, an inhibitor for UGT may be included in the cell-based assay. Suitable inhibitors include salicylamide and diclofenac.

CYP450 activities may be measured in cultured cells, cell fractions (e.g., primarily microsomes, S9 cells and mitochondrial fractions), or semi-purified and purified preparations from either native or recombinant sources. CYP450s are particularly abundant in the liver so cultured hepatocytes are commonly assayed for CYP450 activities, and liver microsomes and liver S9 fractions are often used for cell-free assays. Recombinant expression systems may also be used to produce individual CYP450s enzymes. Additional sources include insect cell/baculovirus, E. coli and yeast expression systems. The liver is of particular interest because its resident CYP450 population plays a central role in the metabolism and elimination of drugs and other xenobiotics. CYP450 induction and inhibition is widely studied because of the central role they play in drug disposition and drug-drug interactions. CYP-dependent metabolism is slowed by inhibitors and accelerated by inducers.

A subset of the human CYP-450s that include CYP450-1A2, -2A6, -2B6, -2C8, -2C9, -2C19, -2D6, -2E1 and -3A4/5 is responsible for most drug metabolism in humans and compounds of interest are applied to cell-free assays for some or all of these to assess inhibition profiles. In the case where recombinant or purified CYP450s are used, the selectivity of the substrate is not an issue. In this case only a single CYP450 enzyme is present in the assay and other cross-reacting enzymes are not present to interfere. However, when liver microsomes or liver S9 fractions are used, selectivity is critical for studies that focus on a single CYP450 enzyme because many CYP450s are co-expressed in liver. With a cross-reactive substrate, the total activity observed from a liver fraction reflects the contributions of all cross-reacting CYP450s in the sample, thereby creating results that can be difficult or impossible to interpret. For this reason, it is desirable to have substrates with a high degree of selectivity for the individual CYP450 enzyme of interest.

A cell-based system is useful for measuring CYP450 induction because it is primarily initiated at the transcription level and cultured hepatocytes are often used as the preferred model. Not all CYP450 genes are inducible by chemicals or other environmental inputs. Those that are inducible include CYP1A2, -2C9, -2C19, -2B6 and CYP3A4, and, as is the case for inhibition studies with liver fractions, CYP450 selective substrates are needed for unambiguous characterization of CYP450-specific induction events.

UGT Assay

The present invention also provides a cell-based UDP glucuronosyl transferase (UGT) assay. In addition to CYP450 enzymes, certain cyanobenzothiazole derivatives are substrates for conjugation to glucuronic acid by UGT enzymes. For example, a cyanobenzothiazole derivative that is a precursor to an active substrate for firefly luciferase (i.e., prosubstrate) is provided as a UGT substrate. The cyclization reaction with cysteine converts these compounds to their luciferase-active forms, e.g. D-luciferin. In a reaction that lacks UGT enzyme activity, no conjugation will occur, and all the cyanobenzothiazole derivative is converted to the active form for luciferase and maximum light output is observed in a luciferase reaction. But, in a reaction with active UGT enzyme, some or all of the cyanobenzothiazole derivative is conjugated to glucuronic acid, and the cysteine cyclized form of the product is inactive with luciferase. Thus, the extent of light reduction compared to a UGT-inactive control can be correlated to UGT activity.

Multiplex Assays

The present invention also provides an assay for detecting more than one non-luciferase enzyme in a sample. For example, a sample containing cells is contacted with two bioluminogenic substrates, one of the substrates being a derivative of 2-cyano-6-substituted benzothiazole, under conditions which allow a reaction between the enzymes and substrates, in a first reaction vessel. A portion of the incubation mixture is then transferred to a second and third reaction vessel. To one of the reaction vessels, a luciferase reaction mixture containing D-cysteine is added. To the other reaction vessel, a luciferase reaction mixture without D-cysteine is added. Bioluminescence is measured in both reaction vessels. Such a multiplex assay can be used to detect two enzymes from an enzyme class, e.g., the CYP450 enzymes CYP1A2 and CYP3A4, or two different enzymes, e.g., a CYP450 enzyme and a UGT enzyme.

Derivatives of 2-Cyano-6-Substituted Benzothiazoles

Figure 2:
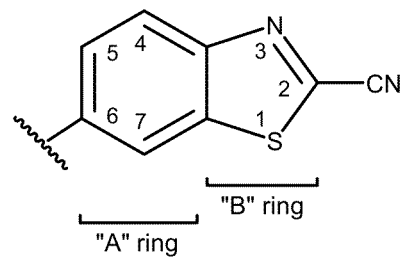
FIG. 2 illustrates the numbering of ring atoms of 2-cyano-6-substituted benzothiazole: the six membered "benzo" ring ("A ring"), and the five membered thiazole ring ("B ring") fused to the benzo ring.

Modifications of 2-cyano-6-substituted benzothiazole within the scope of the derivatives used in the present invention include one or more substitutions of a ring atom, one or more substitutions of a substituent (atom or group) attached to a ring atom, and/or addition of one or more atoms to the ring, e.g., expansion or addition of rings, or a combination thereof. Numbering for some of the ring atoms in 2-cyano-6-substituted benzothiazoles is shown in FIG. 2. 2-Cyano-6-hydroxybenzothiazole has two fused rings, a 6 membered ring having an OH group at position 6 (the "A ring" hereinafter), and a 5 membered ring (the "B ring" hereinafter) fused to the 6 membered ring, having a cyano group at the 2-position. All stereoisomers, e.g., enantiomers and diastereomers, are specifically contemplated herein. One diastereomer may display superior properties or activity compared with another. When required, separation of the racemic material can be achieved by HPLC using a chiral column or by a resolution using a resolving agent such as camphonic chloride as described by Thomas J. Tucker, et al., *J. Med. Chem.* 1994, 37, 2437-2444. A chiral compound may also be directly synthesized using a chiral catalyst or a chiral ligand, e.g. Mark A. Huffman, et al., *J. Org. Chem.* 1995, 60, 1590-1594.

The derivatives of the invention may have one or more modifications to one or more of the rings of 2-cyano-6-substituted benzothiazole and/or substituents attached to one or more of the rings of 2-cyano-6-substituted benzothiazole. Examples include 2-cyano-6-substituted benzothiazoles with a 6-OH, to provide a substrate for a luciferase or a non-luciferase enzyme, or wherein a 6-O, or 6-N atom has a substituent that is a substrate for a luciferase or a non-luciferase enzyme. Further examples of 2-cyano-6-substituted benzothiazoles include compounds of the formulas described herein. In other aspects, 2-cyano-benzothiazoles derivatives that are substituted at the 4-, 5-, or 7-position are provided and can be used in the methods of the invention.

For instance, a 2-cyano-6-hydroxybenzothiazole derivative with an A ring modification may have a substitution of a carbon atom in the A ring with another atom, an addition of a ring, a substitution of a substituent attached to a ring atom with a different atom or group, or any combination thereof. A 2-cyano-6-hydroxy-benzothiazole derivative with a B ring modification may have an addition to or substitution of an atom in the five membered ring, e.g., insertion of one or more atoms, thereby expanding the ring, for instance, to a six membered ring, substitution of N or S in the ring with a different atom, e.g., a C or O, substitution of a substituent atom or group attached to a ring atom, or any combination thereof. In one aspect, a derivative of the invention is one that is modified at more than one position, for instance, the derivative has two (or more) A ring modifications, two (or more) B ring modifications, or any combination thereof. In one aspect, a modification can include the addition of a substituent on one of the rings of 2-cyano-6-hydroxybenzothiazole, wherein the substituent is a substrate for a non-luciferase enzyme, or a linker and a substrate for the non-luciferase enzyme.

In one aspect, derivatives of the invention have the following structure: L-X-M, wherein L may be a substrate for an enzyme or another molecule that interacts with the enzyme; X may be O, NR wherein R is an optionally substituted alkyl group or a nitrogen protecting group, NH, or a linker, e.g., a self-cleavable linker which spontaneously cleaves to yield M after L has been removed from L-X-M; and M may be 2-cyano-benzothiazole, optionally substituted with one or more substituents, e.g., as described herein.

In one aspect, the derivative of 2-cyano-6-substituted benzothiazole can be a compound of formula I:

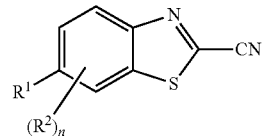

wherein $R^1$ is H, OH, $OR^x$ or $NR^xR^y$;

$R^2$ is $(C_1-C_3)$alkyl, trifluoromethyl, amino, nitro, or halo;

n is 0, 1, 2, or 3;

$R^x$ is (i) $(C_1-C_{10})$alkylaryl wherein the aryl is optionally substituted with one or more of the following halo, hydroxy, amino groups, peptides, or esters, or (ii) $(C_1-C_{10})$alkyl, wherein the alkyl is optionally substituted with alkoxy, hydroxy, halo, or amino; and $R^y$ is hydrogen or $(C_1-C_{10})$alkyl.

In other aspects, the derivative of 2-cyano-6-substituted benzothiazole can also be a compound of any one of formulas IA-XV described herein. In one aspect, the compound of formula I can be:

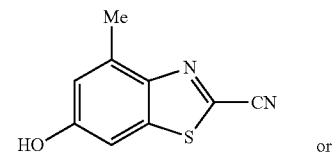

or

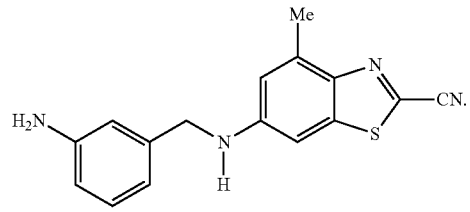

In other aspects, derivatives of 2-cyano-6-substituted benzothiazole can be a compound of any one of formulas I-XV described herein. In one aspect, the invention provides a compound of Formula IA:

(IA)

wherein
Y is N, N-oxide, N—($C_1$-$C_6$)alkyl, or CH;
X is S, O, CH=CH, N=CH, or CH=N;
Z and Z' are independently H, OR, NHR, or NRR;
$W^1$ and Z are both keto groups on ring A, and at least one of the dotted lines denoting optional double bonds in ring A is absent;
each of $K^1$, $K^2$, $K^3$, and $K^4$ are independently CH, N, N-oxide, or N—($C_1$-$C_6$)alkyl, and the dotted lines between $K^1$ and $K^2$, and $K^3$ and $K^4$, denote optional double bonds;
A' and B' are optional aromatic rings fused to ring A, only one of which is present in the compound, so as to form a fused tricyclic system; and
when B' is present, the group Z is present, and
when A' is present, the group Z is absent; and
the dotted line in ring B is an optional double bond;
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroarylsulfonyl, ($C_1$-$C_{20}$)alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, guanidino, or $M^+$, wherein M is an alkali metal;
or when Z or Z' is $NR^1R^1$, $R^1R^1$ together with the N to which they are attached forms a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$)cyclo alkyl, ($C_1$-$C_{20}$)alkoxy, ($C_1$-$C_{20}$)alkylcarbonyl, ($C_1$-$C_{20}$)alkylcarboxyl, halo, hydroxyl, —$COOR^x$, —$SO_2R^x$, —$SO_3R^x$, nitro, amino, ($C_1$-$C_{20}$)alkyl-S(O)—, ($C_1$-$C_{20}$)alkyl-$SO_2$—, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$)alkylthio, ($C_6$-$C_{30}$)aryl, ($C_6$-$C_{30}$)arylthio, trifluoromethyl, =O, heteroaryl, and heterocycle, and each substituent is optionally substituted with one to three R groups;
$R^x$ is H, ($C_1$-$C_6$)alkyl, or ($C_6$-$C_{30}$)aryl;
when Z or Z' comprises a nitrogen moiety, one or both of the hydrogens of the Z or Z' nitrogen moiety may be replaced by ($C_1$-$C_{20}$)alkyl or the group L, wherein L is an amino acid radical, a peptide radical having up to 20 amino acid moieties, or any other small molecule that is a substrate for a non-luciferase;
when Z is a hydroxyl group or a nitrogen moiety, H of the hydroxyl or nitrogen moiety may be replaced by $(HO)_2P$(O)—$OCH_2$—, sulfo, —$PO_3H_2$, or by a cephalosporanic acid attached to the group Z via a carbon chain of one to about 12 carbon atoms;
when Z or Z' is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds,
linker is attached to L' via an oxygen atom or an NH group at one terminus of the linker and the other terminus of the linker forms an ether, ester, or amide linkage with a group Z or Z';
when Z is OR, formula I is optionally a dimer connected at the two A rings via a linker comprising a ($C_1$-$C_{12}$)alkyl diradical that is optionally interrupted by one to four O atoms, N atoms, or an optionally substituted aryl, heteroaryl, or heterocycle group to form a bridge between the dimer of formula I, and the R group of each Z group connecting the dimer of formula I is replaced by the bridge;
$A^-$ is an anion, present when a quaternary nitrogen is present;
or a salt thereof.
In another aspect, the invention provides a compound of Formula IA, which is a compound of Formula IAA:

(IAA)

wherein
Y is N, N-oxide, N—($C_1$-$C_6$)alkyl, or CH;
X is S, O, CH=CH, N=CH, or CH=N;
Z is H, OR, NHR, or NRR;
$W^1$ is H, halo, hydroxyl, ($C_1$-$C_6$)alkyl, or ($C_1$-$C_6$)alkoxy;
the dotted line in ring B is an optional double bond;
each R is independently H, ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{12}$)alkoxy, ($C_6$-$C_{30}$)aryl, heteroaryl, heterocycle, ($C_1$-$C_{20}$)alkylsulfoxy, ($C_6$-$C_{30}$)arylsulfoxy, heteroarylsulfoxy, ($C_1$-$C_{20}$)alkylsulfonyl, ($C_6$-$C_{30}$)arylsulfonyl, heteroarylsulfonyl, ($C_1$-$C_{20}$)alkylsulfinyl, ($C_6$-$C_{30}$)arylsulfinyl, heteroarylsulfinyl, ($C_1$-$C_{20}$)alkoxycarbonyl, amino, NH($C_1$-$C_6$)alkyl, N(($C_1$-$C_6$)alkyl)$_2$, tri($C_1$-$C_{20}$)ammonium($C_1$-$C_{20}$)alkyl, heteroaryl($C_1$-$C_{20}$)alkyl, heteroaryl having quaternary nitrogen, heteroarylcarbonyl having quaternary nitrogen, ($C_6$-$C_{30}$)arylthio, ($C_1$-$C_{20}$)alkylphosphate, ($C_1$-$C_{20}$)alkylphosphonate, ($C_6$-$C_{30}$)arylphosphate, ($C_6$-$C_{30}$)arylphosphonate, phosphate, sulfate, saccharide, or $M^+$, wherein M is an alkali metal;
or when Z is $NR^1R^1$, $R^1R^1$ together with the N to which they are attached forms a heteroaryl or heterocycle group;
wherein any alkyl, alkenyl, alkynyl, cycloalkyl, alkoxy, amino, aryl, heteroaryl, or heterocycle group is optionally substituted with 1, 2, 3, 4, or 5 substituents selected from ($C_1$-$C_{20}$)alkyl, ($C_2$-$C_{20}$)alkenyl, ($C_2$-$C_{20}$)alkynyl, ($C_3$-$C_{20}$)cycloalkyl, ($C_1$-$C_{20}$)alkoxy, ($C_1$-$C_{20}$)alkylcarbonyl, ($C_1$-$C_{20}$)alkylcarboxyl, halo, hydroxyl, —$COOR^x$, —$SO_2R^x$, —$SO_3R^x$, nitro, amino, ($C_1$-$C_{20}$)alkyl-S(O)—, ($C_1$-$C_{20}$)alkyl-$SO_2$—, phosphate, ($C_1$-$C_{20}$)alkylphosphate, ($C_1$-$C_{20}$)alkylphosphonate, NH($C_1$-$C_6$)alkyl, NH($C_1$-$C_6$)alkynyl, N(($C_1$-$C_6$)alkyl)$_2$, N(($C_1$-$C_6$)alkynyl)$_2$, mercapto, ($C_1$-$C_{20}$)alkylthio, ($C_6$-$C_{30}$)aryl, ($C_6$-$C_{30}$)arylthio, trifluoromethyl, =O, heteroaryl, and heterocycle, and each substituent is optionally substituted with one to three R groups;

$R^x$ is H, $(C_1-C_6)$alkyl, or $(C_6-C_{30})$aryl;

$A^-$ is an anion, present when a quaternary nitrogen is present;

or a salt thereof.

In another aspect, the invention provides a compound of formula II:

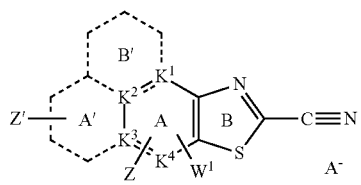

(II)

wherein

Z and Z' are independently $OR^1$, $NHR^1$, or $NR^1R^1$;

$W^1$ is H, halo, $(C_1-C_6)$alkyl, $(C_2-C_{20})$alkenyl, hydroxyl, or $(C_1-C_6)$alkoxy; or $W^1$ and Z are both keto groups on ring A, and at least one of the dotted lines denoting optional double bonds in ring A is absent;

each of $K^1$, $K^2$, $K^3$, and $K^4$ are independently CH, N, N-oxide, or N—$(C_1-C_6)$alkyl, and the dotted lines between $K^1$ and $K^2$, and $K^3$ and $K^4$, denote optional double bonds;

A' and B' are optional aromatic rings fused to ring A, only one of which is present in the compound, so as to form a fused tricyclic system; and when B' is present, the group Z is present, and when A' is present, the group Z is absent; and R is H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroaryl-sulfoxy, $(C_1-C_{20})$alkoxycarbonyl, amino, $NH(C_1-C_6)$alkyl, $N((C_1-C_6)$alkyl$)_2$, tri$(C_1-C_{20})$ammonium $(C_1-C_{20})$alkyl, heteroaryl$(C_1-C_{20})$alkyl, heteroaryl having quaternary nitrogen, heteroarylcarbonyl having quaternary nitrogen, saccharide, or $M^+$, wherein M is an alkali metal;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-SO$_2$, —SO$_3$$(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-SO$_2$, —SO$_3$$(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —COOR$^x$, —SO$_3$R$^x$, $(C_1-C_{20})$alkylthio, $(C_6-C_{30})$arylthio, $(C_1-C_{20})$alkyl-S(O)—, $(C_1-C_{20})$alkyl-SO$_2$—, nitro, amino, $NH(C_1-C_6)$alkyl, $NH(C_1-C_6)$alkynyl, $N((C_1-C_6)$alkyl$)_2$, or $N((C_1-C_6)$alkynyl$)_2$, mercapto, saccharide, or trifluoromethyl;

or when Z or Z' is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, nitro, amino, $NH(C_1-C_6)$alkyl, $NH(C_1-C_6)$alkynyl, $N((C_1-C_6)$alkyl$)_2$, $N((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

$R^x$ is H or $(C_1-C_6)$alkyl;

when Z or Z' comprises a nitrogen moiety, a hydrogen of the Z or Z' nitrogen moiety may be replaced by the group L, wherein L is an amino acid radical, a peptide radical having up to 20 amino acid moieties, or any other small molecule that is a substrate for a non-luciferase;

when Z is a hydroxyl group or a nitrogen moiety, H of the hydroxyl or nitrogen moiety may be replaced by $(HO)_2P(O)$—OCH$_2$—, sulfo, —PO$_3$H$_2$, or by a cephalosporanic acid attached to the group Z via a carbon chain of one to about 12 carbon atoms;

when Z or Z' is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z or Z';

when Z is $OR^1$, formula II is optionally a dimer connected at the two A rings via linker comprising a $(C_1-C_{12})$alkyl diradical that is optionally interrupted by one to four O atoms, N atoms, or an optionally substituted aryl, heteroaryl, or heterocycle group to form a bridge between the dimer of formula II, and the $R^1$ group of each Z group connecting the dimer of formula II is replaced by the bridge;

$A^-$ is an anion, present when a quaternary nitrogen is present;

or a salt thereof.

In yet another aspect, the invention provides a compound of formula II, which is a compound of formula IIA:

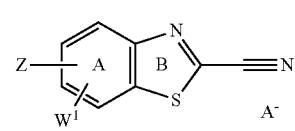

(IIA)

wherein

Z is $OR^1$, $NHR^1$, or $NR^1R^1$;

$W^1$ is H, halo, hydroxyl, $(C_1-C_6)$alkyl, or $(C_1-C_6)$alkoxy;

$R^1$ is $(C_6-C_{30})$aryl, heteroaryl, heterocycle, $(C_1-C_{20})$alkylthio, $(C_1-C_{20})$alkyl-S(O)—, $(C_1-C_{20})$alkyl-SO$_2$, —SO$_3$$(C_1-C_{20})$alkyl, saccharide, $(C_1-C_{20})$alkylphosphate, $(C_1-C_{20})$alkylphosphonate, $(C_6-C_{30})$arylthio, $(C_6-C_{30})$aryl-S(O)—, $(C_6-C_{30})$aryl-SO$_2$, —SO$_3$$(C_6-C_{30})$aryl, $(C_6-C_{30})$arylphosphate, $(C_6-C_{30})$arylphosphonate, or $R^1$ is $(C_1-C_{20})$alkyl substituted by $R^2$;

$R^2$ is $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, hydroxyl, —COOR$^x$, —SO$_3$R$^x$, $(C_1-C_{20})$alkylthio, $(C_6-C_{30})$arylthio, $(C_1-C_{20})$alkyl-S(O)—, $(C_1-C_{20})$alkyl-SO$_2$—, nitro, amino, NH $(C_1-C_6)$alkyl, $NH(C_1-C_6)$alkynyl, $N((C_1-C_6)$alkyl$)_2$, or $N((C_1-C_6)$alkynyl$)_2$, mercapto, saccharide, guanidino or trifluoromethyl;

or when Z is $NR^1R^1$, $R^1R^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, nitro, amino, NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H or $(C_1-C_6)$alkyl;

when Z is OR$^1$, formula IIA is optionally a dimer connected at the two A rings via linker comprising a $(C_1-C_{12})$ alkyl diradical that is optionally interrupted by one to four O atoms, N atoms, or an optionally substituted aryl, heteroaryl, or heterocycle group to form a bridge between the dimer of formula IIA, and the R$^1$ group of each Z group connecting the dimer of formula II is replaced by the bridge;

A$^-$ is an anion, present when a quaternary nitrogen is present;

or a salt thereof.

In one aspect, the invention provides a compound of formula III:

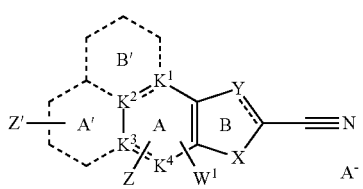

(III)

wherein

Y is N, N-oxide, N—$(C_1-C_6)$alkyl, or CH;

X is S, O, CH=CH, N=CH, or CH=N;

Z and Z' are independently H, OR, NHR, or NRR;

W$^1$ is H, halo, $(C_1-C_6)$alkyl, $(C_2-C_{20})$alkenyl, hydroxyl, or $(C_1-C_6)$alkoxy; or W$^1$ and Z are both keto groups on ring A, and at least one of the dotted lines denoting optional double bonds in ring A is absent;

each of K$^1$, K$^2$, K$^3$, and K$^4$ are independently CH, N, N-oxide, or N—$(C_1-C_6)$alkyl, and the dotted lines between K$^1$ and K$^2$, and K$^3$ and K$^4$, denote optional double bonds;

A' and B' are optional aromatic rings fused to ring A, only one of which is present in the compound, so as to form a fused tricyclic system; and when B' is present, the group Z is present, and when A' is present, the group Z is absent; and the dotted line in ring B is an optional double bond;

each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroaryl-sulfoxy, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino, NH$(C_1-C_6)$alkyl, N$((C_1-C_6)$alkyl$)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen, $(C_6-C_{30})$arylthio, $(C_1-C_{20})$alkylphosphate, $(C_1-C_{20})$alkylphosphonate, $(C_6-C_{30})$arylphosphate, $(C_6-C_{30})$arylphosphonate, phosphate, sulfate, saccharide, or M$^+$, wherein M is an alkali metal;

or when Z or Z' is NR$^1$R$^1$, R$^1$R$^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxyl, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, NH$(C_1-C_6)$alkyl, NH$(C_1-C_6)$alkynyl, N$((C_1-C_6)$alkyl$)_2$, N$((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H, $(C_1-C_6)$alkyl, or $(C_6-C_{30})$aryl;

when Z or Z' comprises a nitrogen moiety, one or both of the hydrogens of the Z or Z' nitrogen moiety may be replaced by $(C_1-C_{20})$alkyl or the group L, wherein L is an amino acid radical, a peptide radical having up to 20 amino acid moieties, or any other small molecule that is a substrate for a non-luciferase;

when Z is a hydroxyl group or a nitrogen moiety, H of the hydroxyl or nitrogen moiety may be replaced by (HO)$_2$P (O)—OCH$_2$—, sulfo, —PO$_3$H$_2$, or by a cephalosporanic acid attached to the group Z via a carbon chain of one to about 12 carbon atoms;

when Z or Z' is a hydroxyl group or a nitrogen moiety, one H of the hydroxyl or nitrogen moiety may be replaced by the group L'-linker, wherein L' is a group removable by an enzyme to free the linker, and linker is a carbon chain that can self-cleave, optionally interrupted by one or more nitrogen atoms, oxygen atoms, carbonyl groups, optionally substituted aromatic rings, or peptide bonds, linker is attached to L' via an oxygen atom or an NH group at one terminus of the linker and the other terminus of the linker forms an ether, ester, or amide linkage with a group Z or Z';

when Z is OR, formula III is optionally a dimer connected at the two A rings via a linker comprising a $(C_1-C_{12})$alkyl diradical that is optionally interrupted by one to four O atoms, N atoms, or an optionally substituted aryl, heteroaryl, or heterocycle group to form a bridge between the dimer of formula III, and the R group of each Z group connecting the dimer of formula III is replaced by the bridge;

A$^-$ is an anion, present when a quaternary nitrogen is present;

or a salt thereof.

In one aspect, the invention provides a compound of formula III, which is a compound of formula IIIA:

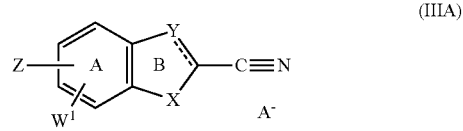

(IIIA)

wherein

Y is N, N-oxide, N—$(C_1-C_6)$alkyl, or CH;

X is S, O, CH=CH, N=CH, or CH=N;

Z is H, OR, NHR, or NRR;

$W^1$ is H, halo, hydroxyl, $(C_1-C_6)$alkyl, $(C_2-C_{10})$alkenyl, or $(C_1-C_6)$alkoxy;

the dotted line in ring B is an optional double bond;

each R is independently H, $(C_1-C_{20})$alkyl, $(C_2-C_{20})$alkenyl, $(C_2-C_{20})$alkynyl, $(C_3-C_{20})$cycloalkyl, $(C_1-C_{12})$alkoxy, $(C_6-C_{30})$aryl, heteroaryl, heterocycle, $(C_1-C_{20})$alkylsulfoxy, $(C_6-C_{30})$arylsulfoxy, heteroaryl-sulfoxy, $(C_1-C_{20})$alkylsulfonyl, $(C_6-C_{30})$arylsulfonyl, heteroarylsulfonyl, $(C_1-C_{20})$alkylsulfinyl, $(C_6-C_{30})$arylsulfinyl, heteroarylsulfinyl, $(C_1-C_{20})$alkoxycarbonyl, amino, $NH(C_1-C_6)$alkyl, $N((C_1-C_6)$alkyl$)_2$, tri$(C_1-C_{20})$ammonium$(C_1-C_{20})$alkyl, heteroaryl$(C_1-C_{20})$alkyl, heteroaryl having quaternary nitrogen, heteroarylcarbonyl having quaternary nitrogen, $(C_6-C_{30})$arylthio, $(C_1-C_{20})$alkylphosphate, $(C_1-C_{20})$alkylphosphonate, $(C_6-C_{30})$arylphosphate, $(C_6-C_{30})$arylphosphonate, phosphate, sulfate, saccharide, or M$^+$, wherein M is an alkali metal;

or when Z is NR$^1$R$^1$, R$^1$R$^1$ together with the N to which they are attached forms a heteroaryl or heterocycle group;

wherein any alkyl, alkenyl, alkynyl, cycloalkyl, alkoxy, amino, aryl, heteroaryl, or heterocycle group is optionally substituted with 1, 2, 3, 4, or 5 substituents selected from $(C_1-C_{20})$alkyl, $(C_2-C_{20})$alkenyl, $(C_2-C_{20})$alkynyl, $(C_3-C_{20})$cycloalkyl, $(C_1-C_{20})$alkoxy, $(C_1-C_{20})$alkylcarbonyl, $(C_1-C_{20})$alkylcarboxyl, halo, hydroxyl, —COOR$^x$, —SO$_2$R$^x$, —SO$_3$R$^x$, nitro, amino, $(C_1-C_{20})$alkyl-S(O)—, $(C_1-C_{20})$alkyl-SO$_2$—, phosphate, $(C_1-C_{20})$alkylphosphate, $(C_1-C_{20})$alkylphosphonate, $NH(C_1-C_6)$alkyl, $NH(C_1-C_6)$alkynyl, $N((C_1-C_6)$alkyl$)_2$, $N((C_1-C_6)$alkynyl$)_2$, mercapto, $(C_1-C_{20})$alkylthio, $(C_6-C_{30})$aryl, $(C_6-C_{30})$arylthio, trifluoromethyl, =O, heteroaryl, and heterocycle, and each substituent is optionally substituted with one to three R groups;

R$^x$ is H, $(C_1-C_6)$alkyl, or $(C_6-C_{30})$aryl;

when Z is OR, formula III is optionally a dimer connected at the two A rings via a linker comprising a $(C_1-C_{12})$alkyl diradical that is optionally interrupted by one to four O atoms, N atoms, an optionally substituted aryl, heteroaryl, or heterocycle group, or a combination thereof, to form a bridge between the dimer of formula III, and the R group of each Z group connecting the dimer of formula III is replaced by the bridge;

A$^-$ is an anion, present when a quaternary nitrogen is present;

or salt thereof.

In one aspect, the invention provides a compound of formula V:

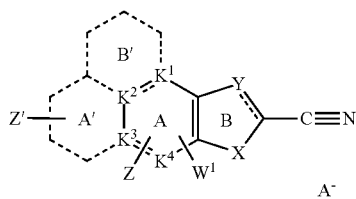

(V)

wherein

Y is N, N-oxide, N-lower alkyl, or CH;

X is S, CH=CH, or N=C,

Z and Z' are H, OR, NHR, or NRR;

W is H, halo, $C_{1-6}$alkyl, $C_{2-20}$alkenyl, hydroxyl, or $C_{1-6}$alkoxy; or W and Z on ring A are both keto groups;

each of K$^1$, K$^2$, K$^3$, and K$^4$ are independently CH, N, N-oxide, or N-lower alkyl;

R is H, $C_{1-20}$alkyl, substituted $C_{1-20}$alkyl, $C_{2-20}$alkenyl, substituted $C_{2-20}$alkenyl, halogenated $C_{2-20}$alkenyl, substituted halogenated $C_{2-20}$alkenyl, $C_{3-20}$alkynyl, substituted $C_{3-20}$alkynyl, $C_{2-20}$alkenylC$_{1-20}$alkyl, substituted $C_{2-20}$alkenylC$_{1-20}$alkyl, $C_{3-20}$alkynylC$_{2-20}$alkenyl, substituted $C_{3-20}$alkynylC$_{2-20}$alkenyl, $C_{3-20}$cycloalkyl, substituted $C_{3-20}$cycloalkyl, $C_{6-30}$aryl, heteroaryl, $C_{6-30}$arylC$_{1-20}$alkyl, substituted $C_{6-30}$aryl, substituted heteroaryl, substituted $C_{6-30}$arylC$_{1-20}$alkyl, alkylsulfoxyC$_{1-20}$alkyl, $C_{1-20}$alkoxycarbonyl, $C_{6-30}$arylC$_{1-20}$alkoxycarbonyl, $C_{6-30}$arylthio $C_{1-20}$alkyl, hydroxyC$_{1-20}$alkyl, triC$_{1-20}$ammoniumC$_{1-20}$alkyl, heteroarylC$_{1-20}$alkyl, substituted heteroarylC$_{1-20}$alkyl, heteroaryl having quaternary nitrogen, heteroarylcarbonyl having quaternary nitrogen, and N-methyl-tetrahydropyridinyl; and M$^+$ when Z" is oxygen, wherein M is an alkali metal; wherein the alkyl, cycloalkyl, alkenyl, and/or alkynyl groups may be optionally substituted by one more $C_{1-20}$alkyl, halo, hydroxyl, acetyl, amino, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, or trifluoromethyl groups, substituted $C_{6-30}$arylC$_{1-20}$alkyl carbonyl; and each group R is defined independently if more than one is present;

and wherein when Z is amino, one or both of the hydrogens may be replaced by $C_{1-20}$alkyl, or the group L, wherein L is an amino acid radical, a peptide radical having up to 20 amino acid moieties, or may be any other small molecule that is a substrate for a non-luciferase;

and wherein when Z is hydroxyl or amino, H may be replaced by (HO)$_2$P(O)—OCH$_2$—, sulfo, or —PO$_3$H$_2$, or by cephalosporanic acid attached to the group Z via a carbon chain of one or more carbon atoms; and when Z is hydroxyl or amino, H may be replaced by the group L'-linker, wherein L' is a group removable by an enzyme to free the linker, and the linker is a carbon chain that may optimally self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z; and when Z is hydroxyl, formula V includes a dimer connected at the two A rings via an —OCH$_2$O— bridge; and wherein A' and B' are optional aromatic rings fused to ring A, only one of which may be present at a time, so as to form a fused tricyclic system; and when B' is present, the group Z is present, and when A' is present, the group Z is absent; and wherein one carbon of ring A may be replaced by an N-oxide moiety;

the dotted line in ring B is an optional double bond;

if X is N=C, ring C is attached at the carbon atom of the N=C moiety; and

A$^-$ is an anion, present when a quaternary nitrogen is present; or a salt thereof.

Further derivatives herein have the general formula VII:

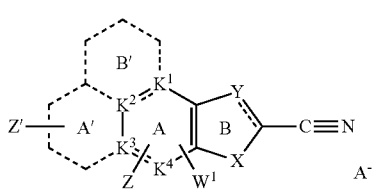

(VII)

wherein
Y is N-oxide, N-lower alkyl, or CH;
X is S or CH=CH; or
Y is N and X is N=C or CH=CH;
Z and Z' are H, OR, NHR, or NRR; or
Z is a cyclic dietherified dihydroxyborane group attached to ring A via the boron atom;
W is H, halo, $C_{1-6}$alkyl, $C_{2-20}$alkenyl, hydroxyl, or $C_{1-6}$alkoxy;
each of $K^1$, $K^2$, $K^3$, and $K^4$ are independently CH, N, N-oxide, or N-lower alkyl;
R is H, $C_{1-20}$alkyl, substituted $C_{1-20}$alkyl, $C_{2-20}$alkenyl, substituted $C_{2-20}$alkenyl, halogenated $C_{2-20}$alkenyl, substituted halogenated $C_{2-20}$alkenyl, $C_{2-20}$alkenyl$C_{1-20}$alkyl, substituted $C_{2-20}$alkenyl$C_{1-20}$alkyl, $C_{3-20}$alkynyl, substituted $C_{3-20}$alkynyl, $C_{3-20}$alkynyl$C_{2-20}$alkenyl, substituted $C_{3-20}$alkynyl$C_{2-20}$alkenyl, $C_{3-20}$cycloalkyl, substituted $C_{3-20}$cycloalkyl, $C_{6-30}$aryl, heteroaryl, $C_{6-30}$aryl$C_{1-20}$alkyl, substituted $C_{6-30}$aryl, substituted heteroaryl, substituted $C_{6-30}$aryl$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl$C_{1-20}$alkyl, substituted heteroaryl$C_{1-20}$alkyl, heteroaryl having quaternary nitrogen, heteroarylcarbonyl having quaternary nitrogen, N-methyl-tetrahydropyridinyl, pentafluorophenylsulphonyl, and $M^+$ when Z" is oxygen, wherein M is an alkali metal; wherein the alkyl, cycloalkyl, alkenyl, and/or alkynyl groups may be optionally substituted by one more $C_{1-20}$alkyl, halo, hydroxyl, acetyl, amino, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio,
$C_{6-30}$arylthio, or trifluoromethyl groups; and each group R is defined independently if more than one is present;
and wherein
when Z is amino, one or both of the hydrogens may be replaced by $C_{1-20}$alkyl, or the group L, wherein
L is an amino acid radical, a peptide radical having up to 20 amino acid moieties, or may be any other small molecule that is a substrate for a non-luciferase;
and wherein
when Z is hydroxyl or amino, H may be replaced by $(HO)_2P(O)-OCH_2-$, sulfo, or
$-PO_3H_2$, or by a cephalosporanic acid attached to the group Z via a carbon chain of one or more carbon atoms; and
when Z is hydroxyl or amino, H may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted)aromatic rings, or peptide bonds, and
linker is attached to L' via an oxygen atom or an NH group at one terminus of the linker and the other terminus of the linker forms an ether, ester, or amide linkage with the group Z; and
when Z is hydroxyl, formula VII includes a dimer connected at the two A rings via an $-OCH_2O-$ bridge; and wherein
A' and B' are optional aromatic rings fused to ring A, only one of which may be present at a time, so as to form a fused tricyclic system; and
when B' is present, the group Z is present, and
when A' is present, the group Z is absent; and
wherein
one carbon of ring A may be replaced by an N-oxide moiety;
the dotted line in ring B is an optional double bond;
if X is N=C, ring C can optionally be attached at the carbon atom of the N=C moiety; and
$A^-$ is an anion, present when a quaternary nitrogen is present; or a salt thereof.
Other derivatives include a compound of formula VIII:

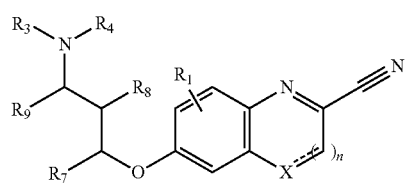

(VIII)

wherein
n=0 or 1 and when
n=0, then X=S, and ---- is a single bond; or when
n=1, then X=CH, and ---- is a double bond;
$R_1$=H, F, or OH;
$R_3$ and $R_4$ are independently H, methyl, ethyl, propyl, allyl, imidazolinylmethyl, or
$R_3$ and $R_4$ together with the nitrogen atom to which they are attached form a piperidino, pyrrolidino, azetidino, or aziridino ring;
$R_7$ is H or methyl;
$R_8$ is H, methyl, hydroxyl, or acetyl; and
$R_9$ is H or methyl. Compounds of formula VIII may be useful as MAO substrates.
Yet other derivatives include a compound of formula IX:

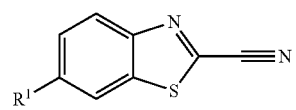

(IX)

wherein $R^1$ is H, OR, NH—C(O)—O-benzyl, or NH—O-isobutyl; and R is lower alkyl, benzyl, 2,4,6-trimethylbenzyl, phenylpiperazinobenzyl, o-trifluoromethylbenzyl, or 3-picolinyl. Such derivatives may be useful as P450 substrates.
Also provided is a compound of formula X:

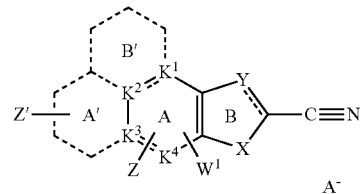

(X)

wherein
Y is N, N-oxide, N-lower alkyl, or CH;
X is S, CH=CH, or N=C,
Z and Z' are independently H, OR, NHR, or NRR;

$W^1$ is H, halo, $C_{1-6}$alkyl, $C_{2-20}$alkenyl, hydroxyl, or $C_{1-6}$alkoxy; or $W^1$ and Z are both keto groups on ring A, and the dotted lines in ring A are absent;

each of $K^1$, $K^2$, $K^3$, and $K^4$ are independently CH, N, N-oxide, or N-lower alkyl, and the dotted lines between $K^1$ and $K^2$, and $K^3$ and $K^4$, denote optional double bonds;

R is H, amino, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, $C_{6-30}$aryl$C_{1-20}$alkyl, $C_{1-12}$alkoxy, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl-sulfoxy, heteroaryl$C_{1-20}$alkyl, heteroaryl having quaternary nitrogen, heteroarylcarbonyl having quaternary nitrogen, N-methyl-tetrahydropyridinyl;

wherein any alkyl, alkenyl, alkynyl, cycloalkyl, alkoxy, aryl, or heteroaryl groups of R can be optionally substituted by one or more, e.g., 1, 2, 3, 4, or 5, $C_{1-20}$alkyl, halo, hydroxyl, acetyl, —COOR$^1$, —SO$_3$R$^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, trifluoromethyl, $C_{1-20}$alkylcarboxyl, $C_{6-30}$aryl, substituted $C_{6-30}$aryl, $C_{6-30}$aryl$C_{1-20}$alkoxyl, heterocycle $C_{1-20}$alkyl, substituted $C_{6-30}$aryl$C_{1-20}$alkoxyl, $C_{6-30}$aryl$C_{1-20}$alkyl carbonyl, substituted $C_{6-30}$aryl$C_{1-20}$alkyl carbonyl or additional unsubstituted R groups; and wherein each group R is defined independently if more than one is present;

wherein heterocycle $C_{1-20}$alkyl is optionally substituted with one or more, e.g., 1, 2, 3, 4, or 5, R groups;

$R^1$ is hydrogen or $C_{1-6}$alkyl;

and wherein when Z is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a non-luciferase;

and wherein when Z is hydroxyl or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms; and when Z or Z' is hydroxyl or amino, one H of the hydroxyl or amino may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z, Z', or Z"—R; and when Z is OR, formula X can optionally be a dimer connected at the two A rings via a CH$_2$ or CH$_2$—C$_6$H$_4$—CH$_2$ bridge, and the R group of each Z group connecting the dimer of formula X is replaced by the bridge; and wherein A' and B' are optional aromatic rings fused to ring A, only one of which may be present at a time, so as to form a fused tricyclic system; and when B' is present, the group Z is present, and when A' is present, the group Z is absent; and wherein one carbon of ring A may be replaced by an N-oxide moiety;

the dotted line in ring B is an optional double bond;

if X is N=C, ring C can optionally be attached at the carbon atom of the N=C moiety; and A$^-$ is an anion, present when a quaternary nitrogen is present; or a salt thereof.

Further provided is a compound of formula XI:

(XI)

wherein

Y is N-oxide, N-lower alkyl, or CH;

X is S or CH=CH; or

Y is N and X is N=C or CH=CH;

Z and Z' are H, OR, NHR, or NRR; or

Z is a cyclic dietherified dihydroxyborane group attached to ring A via the boron atom;

$W^1$ is H, halo, $C_{1-6}$alkyl, $C_{2-20}$alkenyl, hydroxyl, or $C_{1-6}$alkoxy;

each of $K^1$, $K^2$, $K^3$, and $K^4$ are independently CH, N, N-oxide, or N-lower alkyl, and the dotted lines between $K^1$ and $K^2$, and $K^3$ and $K^4$, denote optional double bonds;

R is H, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, $C_{6-30}$aryl$C_{1-20}$alkyl, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl-sulfoxy, heteroaryl$C_{1-20}$alkyl, heteroaryl having quaternary nitrogen, heteroarylcarbonyl having quaternary nitrogen, N-methyl-tetrahydropyridinyl;

wherein the alkyl, alkenyl, alkynyl, cycloalkyl, aryl, and heteroaryl groups of R can be optionally substituted by one or more, e.g., 1, 2, 3, 4, or 5, $C_{1-20}$alkyl, halo, hydroxyl, acetyl, —COOR$^1$, —SO$_3$R$^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, trifluoromethyl, substituted $C_{6-30}$aryl, $C_{1-20}$alkylcarboxyl, substituted $C_{6-30}$aryl, substituted$C_{6-30}$aryl$C_{1-20}$alkoxyl, substituted $C_{6-30}$aryl$C_{1-20}$alkyl carbonyl or additional unsubstituted R group; and each group R is defined independently if more than one is present;

$R^1$ is hydrogen or $C_{1-6}$alkyl;

and wherein when Z is amino, one or both of the hydrogens of the amino group may be replaced by $C_{1-20}$alkyl, or the group L, wherein L is an amino acid radical, a peptide radical having up to 20 amino acid moieties, or may be any other small molecule that is a substrate for a non-luciferase;

and wherein when Z or Z' is hydroxyl or amino, H of the hydroxyl or amino may be replaced by (HO)$_2$P(O)—OCH$_2$—, sulfo, —PO$_3$H$_2$, or by a cephalosporanic acid attached to the group Z via a carbon chain of one or more carbon atoms; and when Z is hydroxyl or amino, one H of the hydroxyl or amino may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z or Z—R; and when Z is hydroxyl, formula XI includes a dimer connected at the two A rings via an —$OCH_2O$— bridge; and
wherein A' and B' are optional aromatic rings fused to ring A, only one of which may be present at a time, so as to form a fused tricyclic system; and when B' is present, the group Z is present, and when A' is present, the group Z is absent; and wherein the dotted line in ring B is an optional double bond;

if X is N=C, ring C can optionally be attached at the carbon atom of the N=C moiety; and $A^-$ is an anion, present when a quaternary nitrogen is present; or a salt thereof.

Also provided is a compound of formula XII:

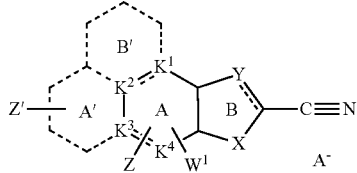

(XII)

wherein

Y is N, N-oxide, N-lower alkyl, or CH;

X is S, CH=CH, or N=C,

Z and Z' are independently H, OR, NHR, or NRR;

$W^1$ is H, halo, $C_{1-6}$alkyl, $C_{2-20}$alkenyl, hydroxyl, or $C_{1-6}$alkoxy; or $W^1$ and Z are both keto groups on ring A, and the dotted lines in ring A are absent;

each of $K^1$, $K^2$, $K^3$, and $K^4$ are independently CH, N, N-oxide, or N-lower alkyl, and the dotted lines between $K^1$ and $K^2$, and $K^3$ and $K^4$, denote optional double bonds;

R is H, $C_{1-20}$alkyl, $C_{2-20}$alkenyl, halogenated $C_{2-20}$alkenyl, $C_{3-20}$alkynyl, $C_{2-20}$alkenyl$C_{1-20}$alkyl, $C_{3-20}$alkynyl$C_{2-20}$alkenyl, $C_{3-20}$cycloalkyl, $C_{6-30}$aryl, heteroaryl, heterocyclic, substituted heterocyclic, $C_{6-30}$aryl$C_{1-20}$alkyl, $C_{1-20}$alkylsulfoxy, $C_{6-30}$arylsulfoxy, $C_{6-30}$arylsulfoxy$C_{1-20}$alkyl, $C_{1-20}$alkylsulfoxy$C_{1-20}$alkyl, $C_{1-20}$alkoxycarbonyl, $C_{6-30}$aryl$C_{1-20}$alkoxycarbonyl, $C_{6-30}$arylthio$C_{1-20}$alkyl, hydroxy$C_{1-20}$alkyl, tri$C_{1-20}$ammonium$C_{1-20}$alkyl, heteroaryl-sulfoxy, heteroaryl$C_{1-20}$alkyl, heteroaryl having quaternary nitrogen, heteroarylcarbonyl having quaternary nitrogen, N-methyl-tetrahydropyridinyl;

wherein the alkyl, alkenyl, alkynyl, cycloalkyl, aryl, and heteroaryl groups of R can be optionally substituted by one or more, e.g., 1, 2, 3, 4, or 5, $C_{1-20}$alkyl, halo, hydroxyl, acetyl, —$COOR^1$, —$SO_3R^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, trifluoromethyl, $C_{1-20}$alkylcarboxyl, $C_{6-30}$aryl, substituted $C_{6-30}$aryl, $C_{6-30}$aryl$C_{1-20}$alkoxyl, substituted $C_{6-30}$aryl$C_{1-20}$alkoxyl, $C_{6-30}$aryl$C_{1-20}$alkyl carbonyl, substituted $C_{6-30}$aryl$C_{1-20}$alkyl carbonyl or additional unsubstituted R groups; and wherein each group R is defined independently if more than one is present;

wherein substituted aryl groups are substituted with one or alkyl, alkenyl, alkynyl, cycloalkyl, aryl, heterocyclic, substituted heterocyclic, and heteroaryl groups of R can be optionally substituted by one or more $C_{1-20}$alkyl, $C_{6-10}$aryl, halo, hydroxyl, acetyl, —$COOR^1$, amino, nitro, lower alkylamino, lower alkynylamino, imidazolinylmethylamino, di-lower alkylamino, di-lower alkynylamino, piperidino, pyrrolidino, azetidino, aziridino, di-imidazolinylmethylamino, mercapto, $C_{1-20}$alkylthio, $C_{6-30}$arylthio, or trifluoromethyl groups;

$R^1$ is hydrogen or $C_{1-6}$alkyl;

and wherein when Z is amino, one or both of the hydrogens of the amino group may be replaced by $C_{1-20}$alkyl, or the group L, wherein L is an amino acid radical, a peptide radical having up to 20 amino acid moieties, or any other small molecule that is a substrate for a non-luciferase;

and wherein when Z is hydroxyl or amino, H may be replaced by $(HO)_2P(O)$—$OCH_2$—, sulfo, or —$PO_3H_2$, or by a cephalosporanic acid attached to the group Z via a carbon chain of one or more carbon atoms; with the proviso that when ring B is a thiazole ring, the sulfo or the —$PO_3H_2$ group is attached to the hydroxyl oxygen via a lower alkylene chain; and when Z or Z' is hydroxyl or amino, one H may be replaced by the group L'-linker, wherein L' is a group removable by an enzyme to free the linker, and linker is carbon chain that can self-cleave, optionally interrupted by one or more nitrogen atoms, oxygen atoms, carbonyl groups, (substituted) aromatic rings, or peptide bonds, and linker is attached to L' via an oxygen atom or an NH group at one terminus of the linker and the other terminus of the linker forms an ether, ester, or amide linkage with the group Z or Z'—R; and when Z is hydroxyl, formula XII includes a dimer connected at the two A rings via an —$OCH_2O$— bridge; and
wherein A' and B' are optional aromatic rings fused to ring A, only one of which may be present at a time, so as to form a fused tricyclic system; and when B' is present, the group Z is present, and when A' is present, the group Z is absent; and wherein the dotted line in ring B is an optional double bond;

if X is N=C, ring C can optionally be attached at the carbon atom of the N=C moiety; and $A^-$ is an anion, present when a quaternary nitrogen is present; or a salt thereof.

Also provided is a compound of formula XV:

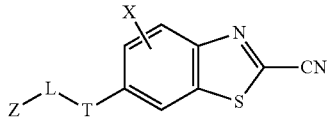

(XV)

wherein

Z is hydrogen or a protecting group;

L is a linker as described herein below, for example, an amino acid or a chain of 2-10 amino acids;

T is O or NH; and

X is hydrogen or fluorine, with the proviso that if X=H then at least one of the amino acids is R,N,D,C,Q,E,H,K,S,T,W, or Y.

In various aspects, Z can be a protecting group for a heteroatom, for example, a nitrogen or oxygen protecting group. Examples of protecting groups are discussed above. In certain specific aspects, the protecting groups can be Cbz, Boc, acetyl, or succinyl groups.

In certain aspects, the compound of formula XV can be the compound
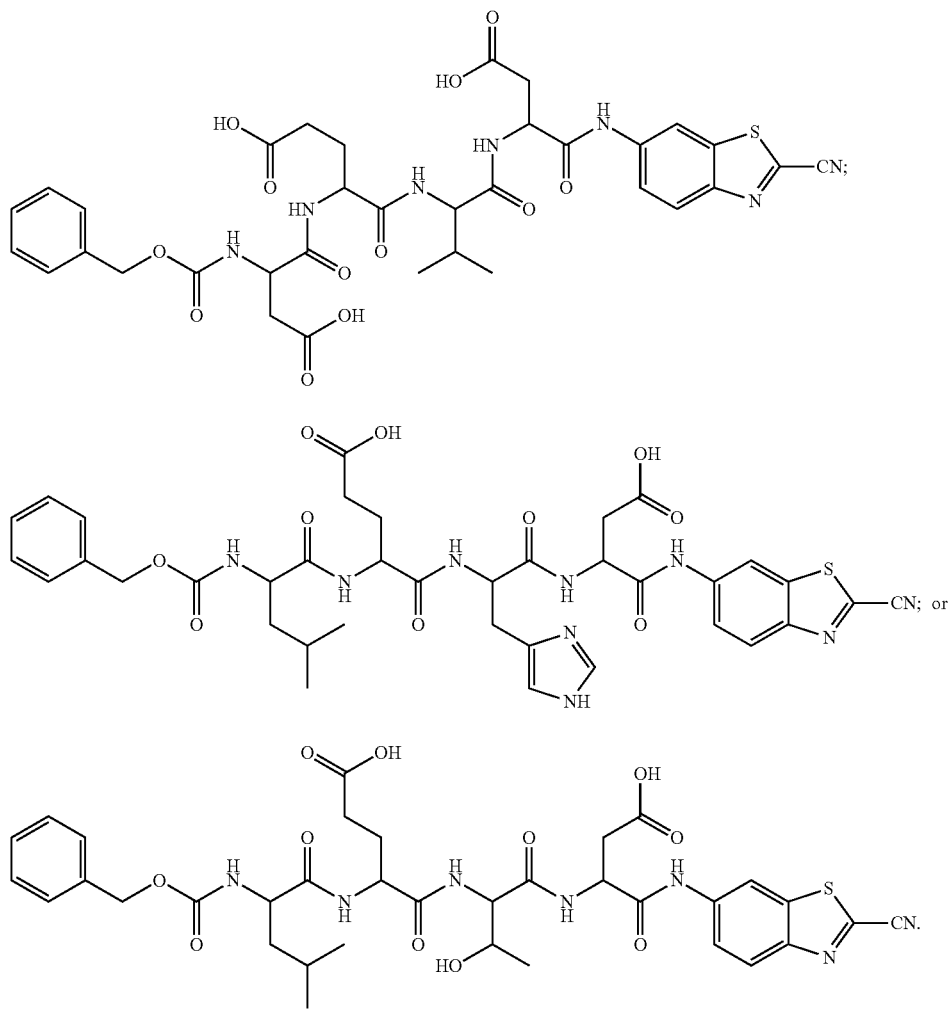
Other examples of compounds of the formulas above include the following structures:
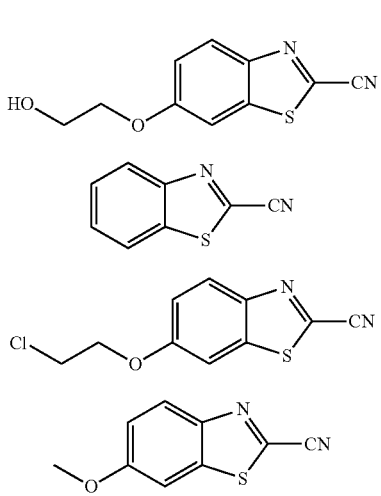
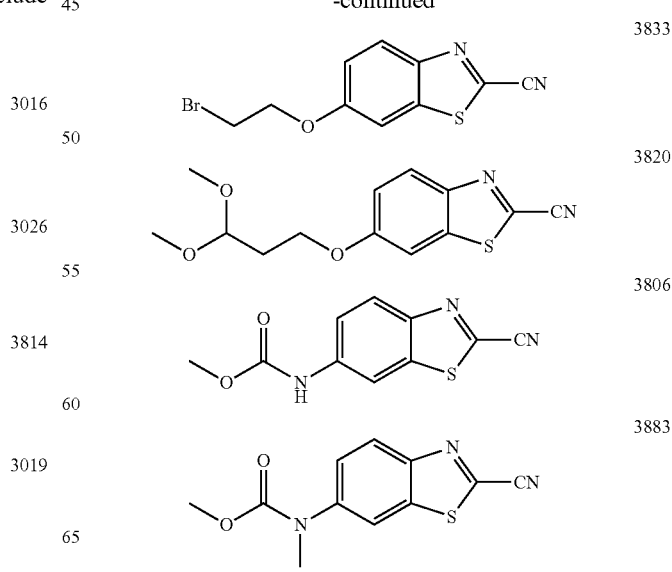

-continued

| | |
|---|---|
| 3821 | 3024 |
| 3835 | 3891 |
| 3866 | 3907 |
| 3868 | 3828 |
| 3138 | 3017 |
| 3165 | 3018 |
| 3819 | 3021 |
| 3823 | 3020 |
| 3023 | |
| 3022 | 3851 |

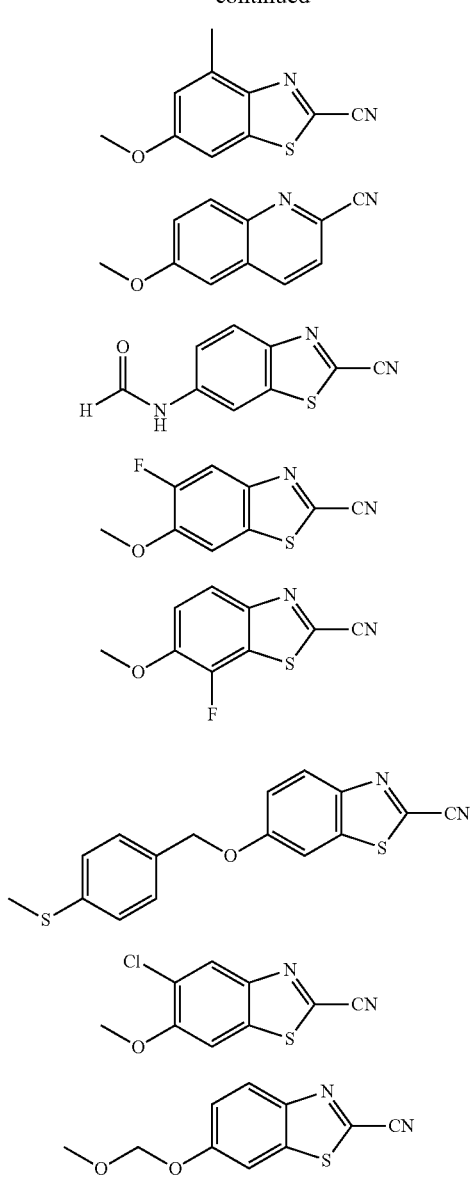

Alkyl or aryl groups of these compounds can be additionally or alternatively substituted with one or more (e.g., 1, 2, 3, 4, 5, or 6) substituents, as described above, and/or, for example, as described in the definition of the term 'substituted'.

For CYP450s, useful substrates include, but are not limited to, 3019, 3016, 3026, 3814, and 3820. For UGT, useful substrates include, but are not limited to, 3138 (commercial) and 3165.

Linkers

A linker strategy may be employed for the A ring modified 2-amino-6-hydroxy-benzothiazole, to introduce a substrate for an enzyme of interest such as a deacetylase, deformylase, demethylase or other enzyme that can remove the L group of formula I (a substrate for that enzyme) to free the linker, yielding a product that in the presence of D-cysteine substrate of luciferase, where the remaining linker may optionally be removed by a nonenzymatic reaction.

Linkers can be alkyl or alkoxy chains, such as $(C_1-C_6)$alkyl or $(C_1-C_6)$alkoxy groups. The chain can have one or more electron withdrawing group substituents R, such as an aldehyde, acetyl, sulfoxide, sulfone, nitro, cyano group, or a combination thereof. Other linkers include trimethyl lock, quinine methide and diketopiperazine linkers, and their derivatives. A trimethyl lock linker can be illustrated as follows:

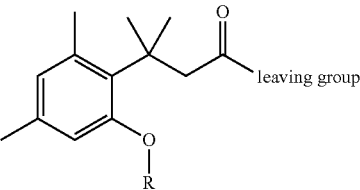

wherein R is as defined for any one of the Roman numeral formulas described herein, for example, formulas I-III, V, VII-IX, XI-XII, and XV, which is a group removable by an enzyme, e.g., an enzyme that is being assayed; the trimethyl lock linker replaces a hydrogen atom of one of the groups Z or Z'—R; and 'leaving group' is the remainder of the structure of formula I-III, V, VII-IX, XI-XII, and XV. See Wang et al., *J. Org. Chem.*, 62:1363 (1997) and Chandran et al., *J. Am. Chem. Soc.*, 127:1652 (2005) for the use of trimethyl lock linkers.

A quinine methide linker can be illustrated as follows:

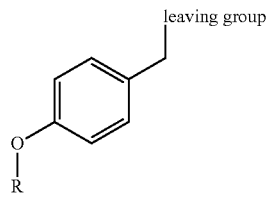

wherein R is as defined for any one of formulas I-III, V, VII-IX, XI-XII, and XV which is a group removable by an enzyme, e.g., an enzyme that is being assayed; the quinine methide linker replaces a hydrogen atom of one of the groups Z or Z'—R; and 'leaving group' is the remainder of the structure of formula I-III, V, VII-IX, XI-XII, and XV. See Greenwald et al., *J. Med. Chem.*, 42:3657 (1999) and Greenwald et al., *Bioconjugate Chem.*, 14:395 (2003) for the use of quinine methide linkers.

A diketopiperazine linker can be illustrated as follows:

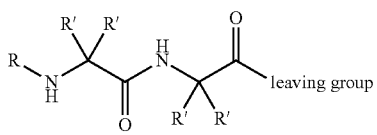

wherein R is as defined for any one of formulas I-III, V, VII-IX, XI-XII, and XV which is a group removable by an enzyme, e.g., an enzyme that is being assayed; each R' of the diketopiperazine linker is independently H or an alkyl chain optionally interrupted by O, S, or NH, preferably a methyl group; the diketopiperazine linker replaces a hydrogen atom of one of the groups Z or Z'—R; and 'leaving group' is the remainder of the structure of formula I-III, V, VII-IX, XI-XII, and XV. See Wei et al., *Bioorg. Med. Chem. Lett.*, 10: 1073 (2000) for the use of diketopiperazine linkers.

Other linker containing derivatives include:

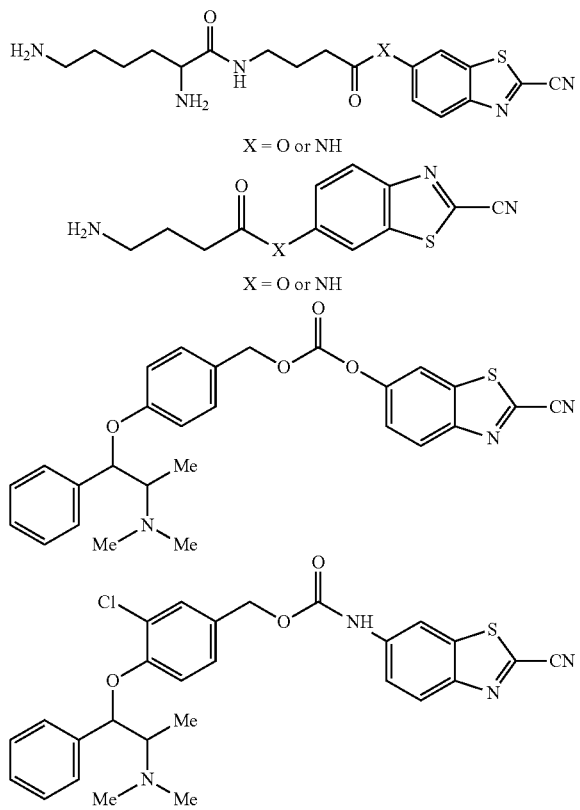

General Synthetic Methods

Preparation of the compounds of formulas I-XV can be prepared from the corresponding 2-halobenzothiazole, or may be prepared according to known techniques in the art of organic synthesis. Many 2,6-disubstituted benzothiazoles are commercially available, and/or can be prepared as described in the art. Information regarding general synthetic methods that may be used to prepare the compounds described herein may be found in Greg T. Hermanson, Bioconjugate Techniques, Academic Press, San Diego, Calif. (1996); March's Advanced Organic Chemistry Reactions, Mechanisms, and Structure, 5th Ed. by Michael B. Smith and Jerry March, John Wiley & Sons, Publishers; and Wuts et al. (1999), Protective Groups in Organic Synthesis, 3rd Ed., John Wiley & Sons, Publishers. Synthesis may be performed as described in: White et al. 1963. J. Amer. Chem. Society 85:337-43 and Beneteau et al. 1997. Synthetic Communications 27(13): 2275-2280, both of which are incorporated by reference herein.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

General Introduction to Examples 1-7

The invention includes a method of determining activity of the uridine 5'-diphospho-glucuronosyltransferase (UDP-glucuronosyltransferase or UGT) family enzymes in vitro. Briefly, UGT enzymes from overexpressed insect microsomes (Supersomes™, BD Gentest™) or animal tissue microsomes (Xenotech, BD Gentest™) were incubated with a cyanobenzothiazole substrate of the invention and the cofactor UDP-glucuronic acid (UDPGA) at 37° C. in buffer at physiological pH containing $MgCl_2$ and alamethicin (typically, 50 mM TES, pH 7.5, 8 mM $MgCl_2$, 4 mM UDPGA (Sigma) and 25 μg/mL alamethicin (Sigma)). Following the UGT enzyme reaction, an equal volume of P450-Glo Luciferin Detection Reagent (LDR) (Promega) containing 15-30 mM D-cysteine-$HCl.H_2O$ (Sigma) was added and the plate was mixed and incubated at room temperature, typically for 20-30 minutes. P450-Glo Luciferin Detection Reagent contains a luciferase reaction mixture that includes a recombinant firefly luciferase, ATP and $Mg^{2+}$. It can be prepared by dissolving a vial of Promega Luciferin Detection Reagent (Promega Part #V859B) with a vial of Promega P450-Glo Buffer (Promega Part #V865B).

During this incubation, the cysteine reacts with the cyanobenzathiozole substrate to yield a D-luciferin derivative. The presence of the luciferin derivative formed from the unmodified substrate results in light output in the presence of the P450-Glo LDR, while any substrate that was glucuronidated by UGT does not initiate light output. Therefore, activity of the UGT enzyme can be measured by analyzing the difference (lower or no output) in relative light units (RLU) of a sample in which glucuronidation occurs compared to a sample that was run under the same conditions with no added UDPGA cofactor.

Example 1

Detection of UDP Glucuronosyltransferase (UGT) Activity with Compounds 3138, 3478, and 3165

In this example, a series of 12 recombinant UGTs expressed in insect microsomes (Supersomes™, BD Gentest™), as well as the control microsomes not expressing the UGT enzyme, were incubated with compound 3138, compound 3478, or compound 3165 as substrates, with or without the UDPGA co-factor.

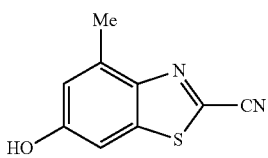

3138

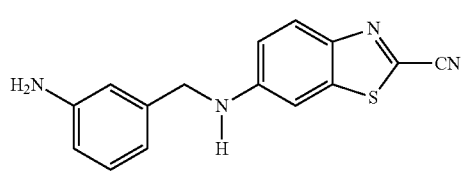

3165

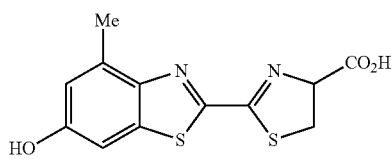

3478

Figure 3:
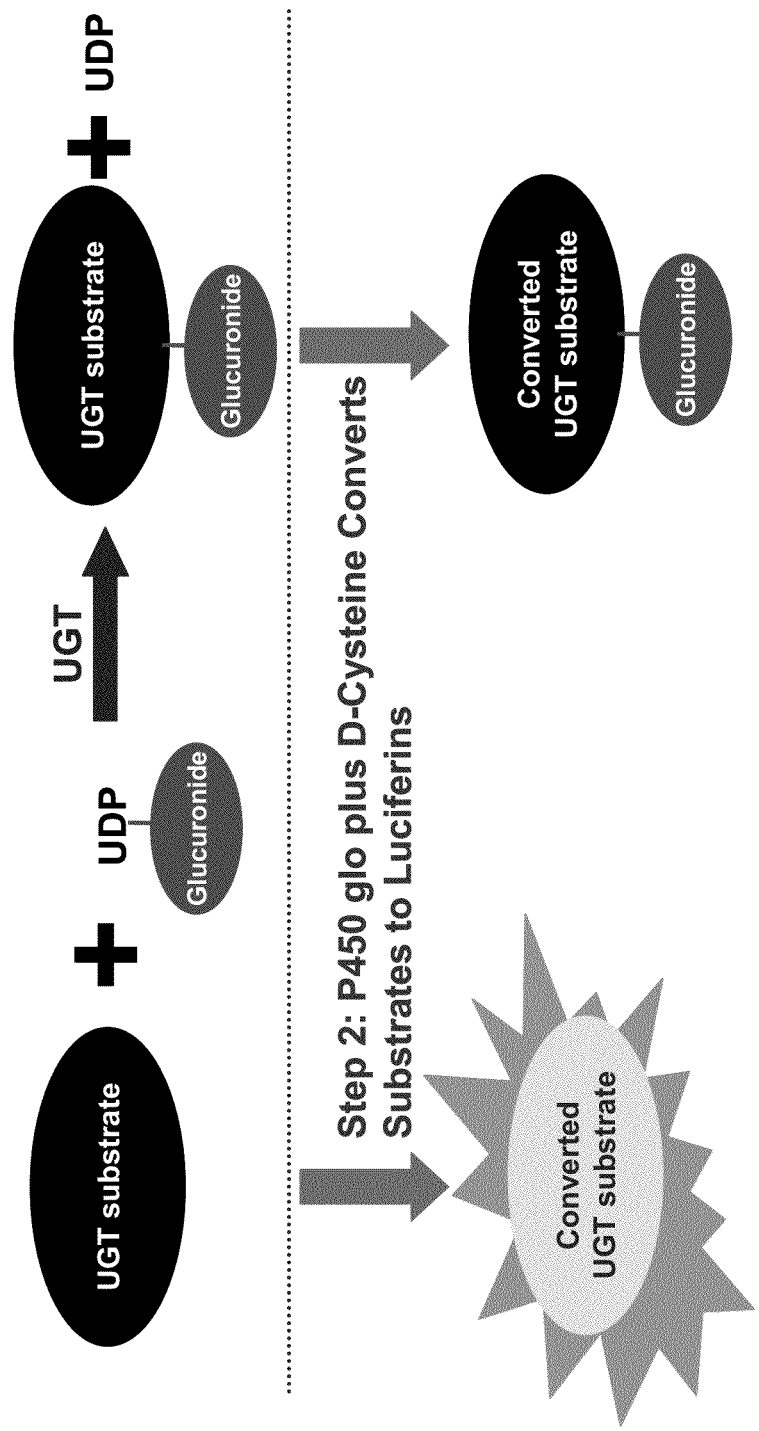
FIG. 3 is a schematic illustration of detecting UDP Glucuronosyltransferase (UGT) activity, according to an aspect of the invention.

After addition of a luciferin detection reagent (LDR) containing D-cysteine, both the substrate and the product were converted to D-luciferins (compound 3478 is already a luciferin derivative before addition of the LDR). Only the unglucuronidated substrate produced light, as shown in FIG. 3, which uses compound 3138 as an example, and any substrate glucuronidated by the enzyme does not produce light, resulting in a drop in relative light units (RLU) for that sample.

Reactions were assembled in a white, 96-well plate. Each well contained 20 µL of reaction mixture comprised of 100 mM TES, pH 7.5, 16 mM $MgCl_2$, 50 µg/mL alamethicin (Sigma), 60 µM compound 3138 or compound 3478, and 0.4 mg/mL of control or recombinant UGT membranes. The reactions were initiated by addition of 20 µL of water or 8 mM triammonium UDPGA (Sigma) to each well. The plate was mixed, sealed, and incubated in a 37° C. water bath for 2 hours. After the incubation, 40 µL P450-Glo LDR (Promega) with 20 mM D-cysteine-HCl.$H_2O$ (Sigma) was added to each well, the plate was mixed and allowed to incubate at room temperature for 20 minutes. After the incubation was completed, the plate was read on a Veritas™ luminometer (Turner BioSystems, Inc.; Sunnyvale, Calif.).

For each isozyme, the bioluminescence from the replicates containing UDPGA were subtracted from the average bioluminescence of the replicates without UDPGA. The average Δ RLU value obtained and the standard deviation of the replicates were then divided by the average bioluminescence for samples without UDPGA to obtain the % utilization for each isozyme. The % utilization obtained from the control microsomes was then subtracted from each isozyme to give the background corrected utilization data for those isozymes.

Figure 4:
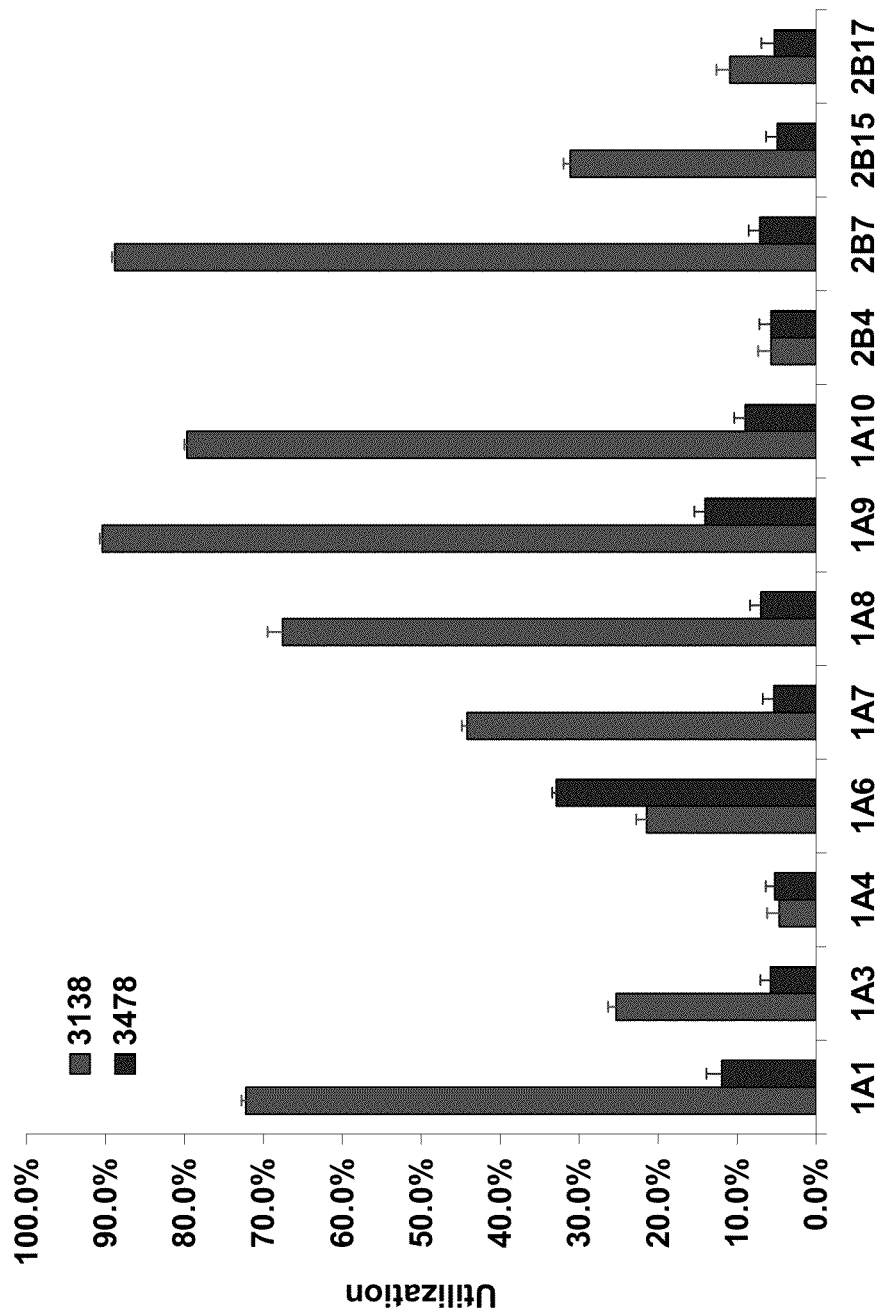
FIG. 4 illustrates the activity data for 12 UGT isozymes, with respect to the utilization of compounds 3138 and 3478, according to an aspect of the invention.
Figure 5:
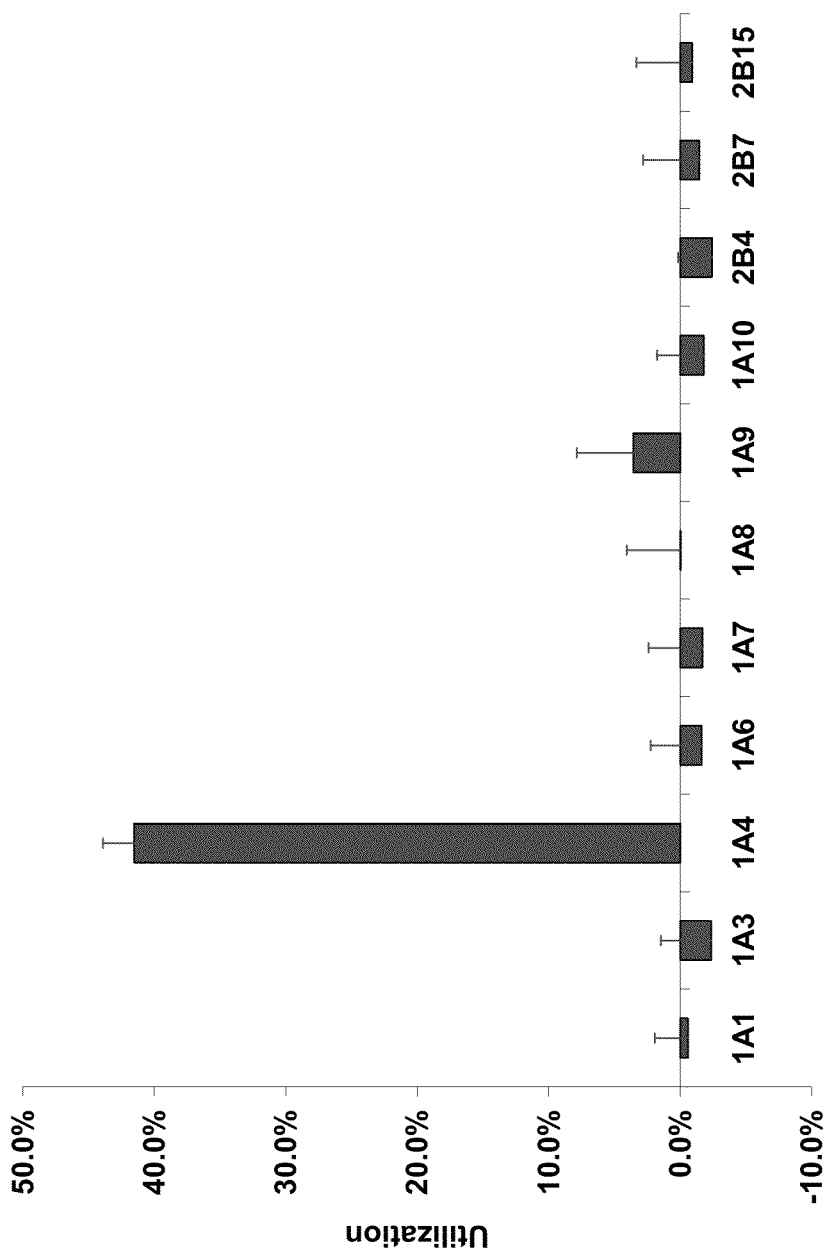
FIG. 5 illustrates the activity data for 12 UGT isozymes, with respect to the utilization of compound 3165, according to an aspect of the invention.

Activity data for these 12 isozymes are shown in FIGS. 4 and 5. The major UGT isozymes 1A1, 1A8, 1A9, 1A10, and 2B7 all utilized over 50% of compound 3138 during the 2 hour incubation. These same isozymes utilized 15% or less of the compound 3478, the luciferin analog of compound 3138, demonstrating the need to use a pre-luciferin to measure these enzymes. Although compound 3138 utilization was less for UGT 1A3, 1A6, 1A7, 2B15, and 2B17, there were still detectable levels of utilization above background. The utilization of compound 3138 by these enzymes could be further optimized by modulating reaction time, concentration of microsomal enzyme, and/or concentration of compound 3138. Of this second set with isozymes and PBI 3478, only UGT 1A6 was able to utilize compound 3478 to any appreciable extent. UGT 1A4 and 2B4 did not utilize either compound 3138 or 3478 to an appreciable extent as substrates. Compound 3165 was only utilized by UGT 1A4, and to a lesser extent, UGT 1A9 (FIG. 5).

Example 2

Utilization of Compounds 3138 and 3165 by Mammalian Microsomes

The ability of endogenously expressed UGT isozymes to utilize compounds 3138 and 3165 as substrates was determined in a similar manner to the assays with recombinant microsomes (Example 1). With compound 3138, reactions were incubated for 15 minutes at 37° C. in 50 mM TES, pH 7.5, 8 mM $MgCl_2$, 25 µg/mL alamethicin, 0.1 mg/mL mammalian microsomes or 0.2 mg/mL recombinant Supersomes, and 50 µM compound 3138, plus or minus 4 mM UDPGA (test reaction and control, respectively). With compound 3165, reactions were incubated for 2 hours at 37° C. in 50 mM TES, pH 7.5, 8 mM $MgCl_2$, 25 µg/mL alamethicin, 0.2 mg/mL mammalian microsomes or recombinant Supersomes, and 50 µM compound 3165, plus or minus 4 mM UDPGA (test reaction and control, respectively). Tissue microsomes were obtained from Xenotech LLC or BD Gentest. Addition of P450-Glo LDR plus cysteine and data analysis was performed in the same manner as for the recombinant Supersome panel screen (Example 1 above).

Figure 6:
FIG. 6 illustrates utilization of compounds 3138 by mammalian microsomes.

Utilization of compound 3138 was rapid as the reaction had to be cut short at 15 minutes in order to see the differences between the different tissue microsomes and animal microsomes. All tissue microsomes tested utilized much more of compound 3138 than the control 1A1 Supersomes (FIG. 6). This result is not unexpected as the concentration of UGT 1A1 in Supersomes, although derived from cells overexpressing the protein, is not likely higher than the additive concentration of all isozymes capable of utilizing compound 3138 in the tissue microsome samples. In addition, recent reports indicate that UGT isozymes may have more than additive activity when expressed together in a single membrane.

Figure 7:
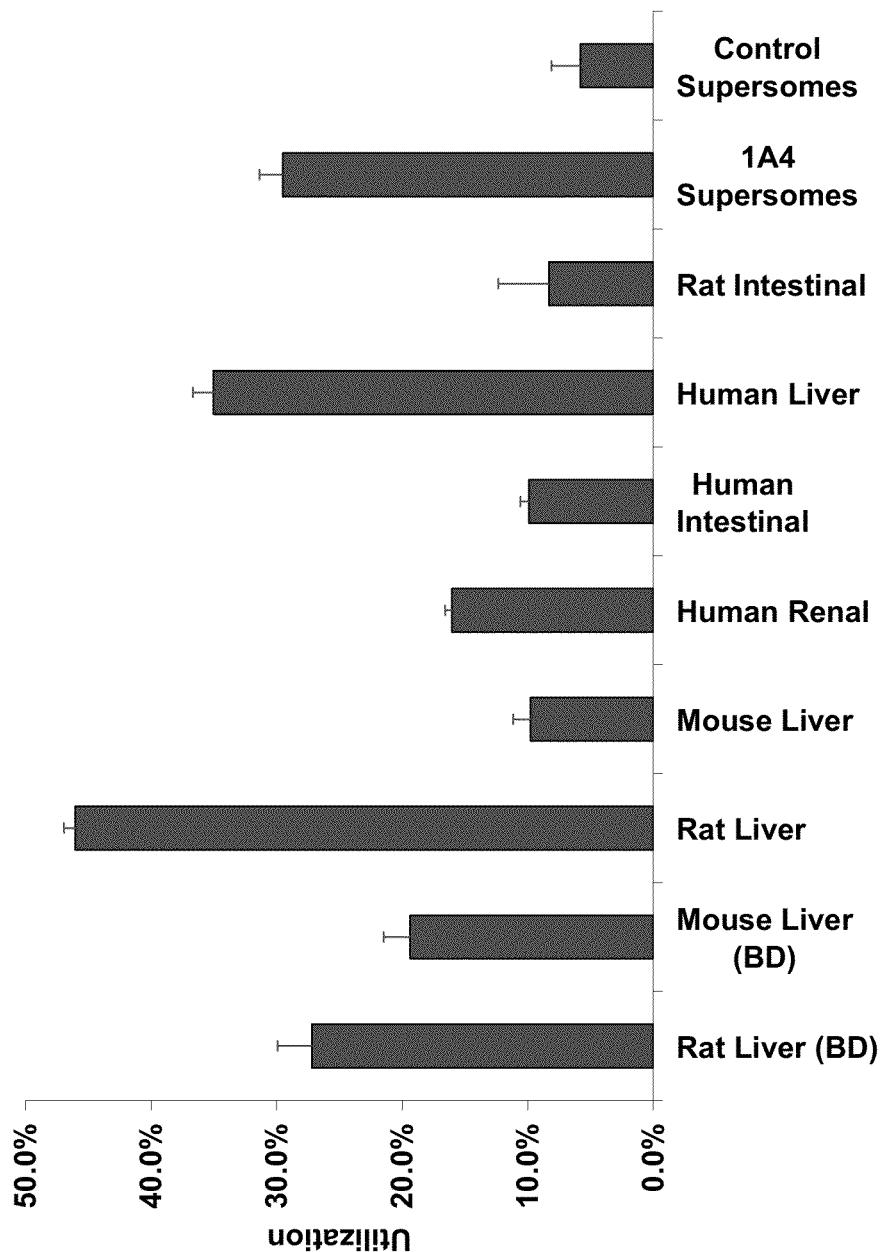
FIG. 7 illustrates utilization of compounds 3165 by mammalian microsomes.

Utilization of compound 3165 was much slower, consistent with its use by mainly one isozyme (UGT 1A4, or similar activities from rats or mice) (FIG. 7). Accordingly, reactions were incubated for 2 hours. Activity was much higher for human liver microsomes than either human renal or human intestinal microsomes, consistent with reports that expression of UGT 1A4 is higher in liver than in extra-hepatic tissues. Activity was also seen for both rat and mouse liver microsomes.

Example 3

Measuring Inhibition of Recombinant UGT Isozymes by Ritonavir with Compounds 3138 and 3165

It was reported in the literature that the HIV protease inhibitor ritonavir inhibits UGT 1A1 and 1A4, but has little effect on UGT 2B7. To test this observation in the current system, compound 3138 was used to detect UGT 1A1 and 2B7 in UGT 1A1 and 2B7 Supersomes and compound 3165 was used to detect UGT 1A4 in UGT 1A4 Supersomes. Reactions with compound 3138 were carried out in 50 mM TES, pH 7.5, 8 mM $MgCl_2$, 25 µg/mL alamethicin, 0.2 mg/mL Supersomes, 50 µM compound 3138, and 0-162 µM ritonavir (AK Scientific), plus or minus 5 mM UDPGA. After 2 hours at 37° C., 10 µL of 50 mM D-cysteine-HCl.$H_2O$ diluted in 200 mM HEPES, pH 8.0 was added to each 40 µL UGT reaction. After 10 minute incubations, 50 µL P450-Glo LDR (Promega) was added to each well, and bioluminescence was measured. Reactions with compound 3165 were incubated in a similar manner using 25 µM 3165, except reactions were only incubated at 37° C. for 70 minutes with concentrations of ritonavir up to 40 µM.

Figure 8:
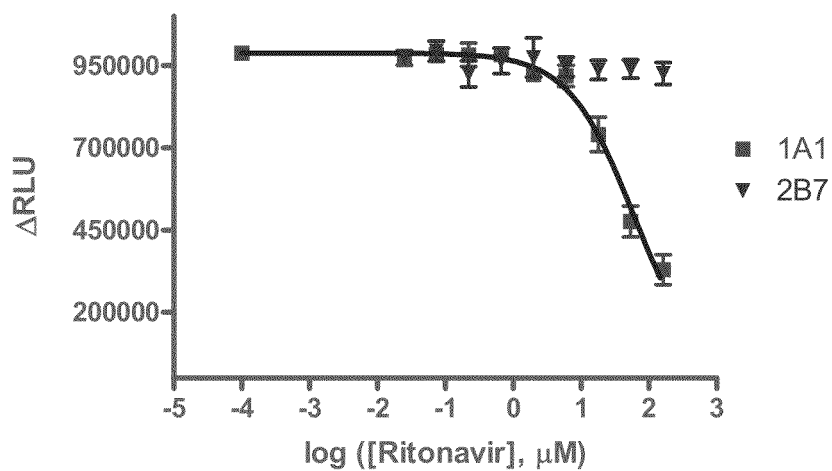
FIG. 8 illustrates inhibition of various UGT isozymes by ritonavir using compound 3138 by a method described herein.
Figure 9:
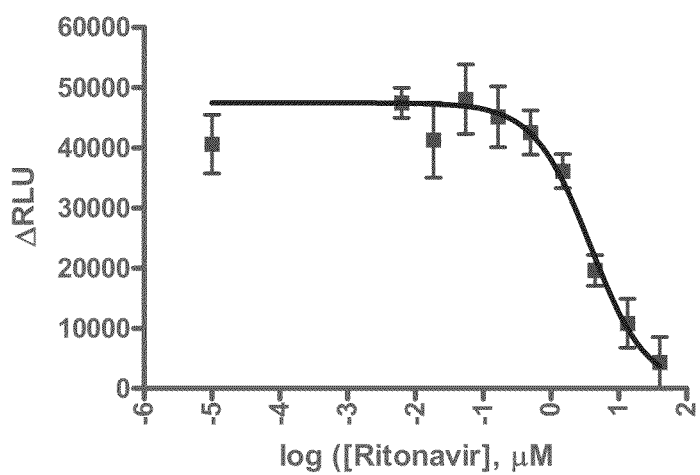
FIG. 9 illustrates inhibition of various UGT isozymes by ritonavir using compound 3165 by a method described herein.

Results with compounds 3138 and 3165 are shown in FIGS. 8 and 9, respectively. Ritonavir inhibits UGT 1A1 and UGT 1A4, but not UGT 2B7, which is in agreement with the literature. Measurements indicated $IC_{50}$ values of 60 µM for UGT 1A1 and 4 µM for UGT 1A4. This result shows the ability of the assay system to identify inhibitors of specific UGT isozymes using recombinant Supersomes.

Example 4

Inhibition of Recombinant UGT Isozymes and UGT Activities in Human Liver Microsomes with Diclofenac Diclofenac is a non-steroidal anti-inflammatory drug (NSAID) that is a known substrate for many of the UGT enzymes and is also reported to inhibit UGT 1A1, 1A3, 1A6, 1A7, 1A8, 1A9, 1A10, 2B7, 2B15, and 2B17. Its broad inhibitory activity against most UGT isozymes makes it an ideal candidate to investigate inhibition of UGT activities in both recombinant UGT preparations and human liver microsomes (HLM).

To assess the ability of diclofenac to inhibit recombinant UGTs, reactions were set up using UGT 1A1 and 2B7 Supersomes. These reactions contained 50 mM TES, pH 7.5, 8 mM $MgCl_2$, 25 µg/mL alamethicin, 0.1 mg/mL Supersomes™, and 20 µM compound 3138, plus or minus 4 mM UDPGA. The titration was performed over a concentration of 0-10 mM diclofenac. After 90 minutes at 37° C., 40 µL of P450-Glo LDR plus 20 mM D-cysteine was added to each 40 µL reaction and mixed. After 20 minutes at room temperature, bioluminescence was measured on a luminometer.

To assess the ability of diclofenac to inhibit UGT activity in HLM, reactions were set up as follows. All reactions contained 50 mM TES, pH 7.5, 8 mM $MgCl_2$, 25 µg/mL alamethicin, 0.1 mg/mL HLM, and 50 µM compound 3138, plus or minus 4 mM UDPGA. The titration was performed over a concentration of 0-3.6 mM diclofenac. After 15 minutes at 37° C., 40 µL of P450-Glo LDR plus 20 mM D-cysteine was added to each 40 µL reaction and mixed. After 20 minutes at room temperature, bioluminescence was measured on a luminometer.

Figure 10:
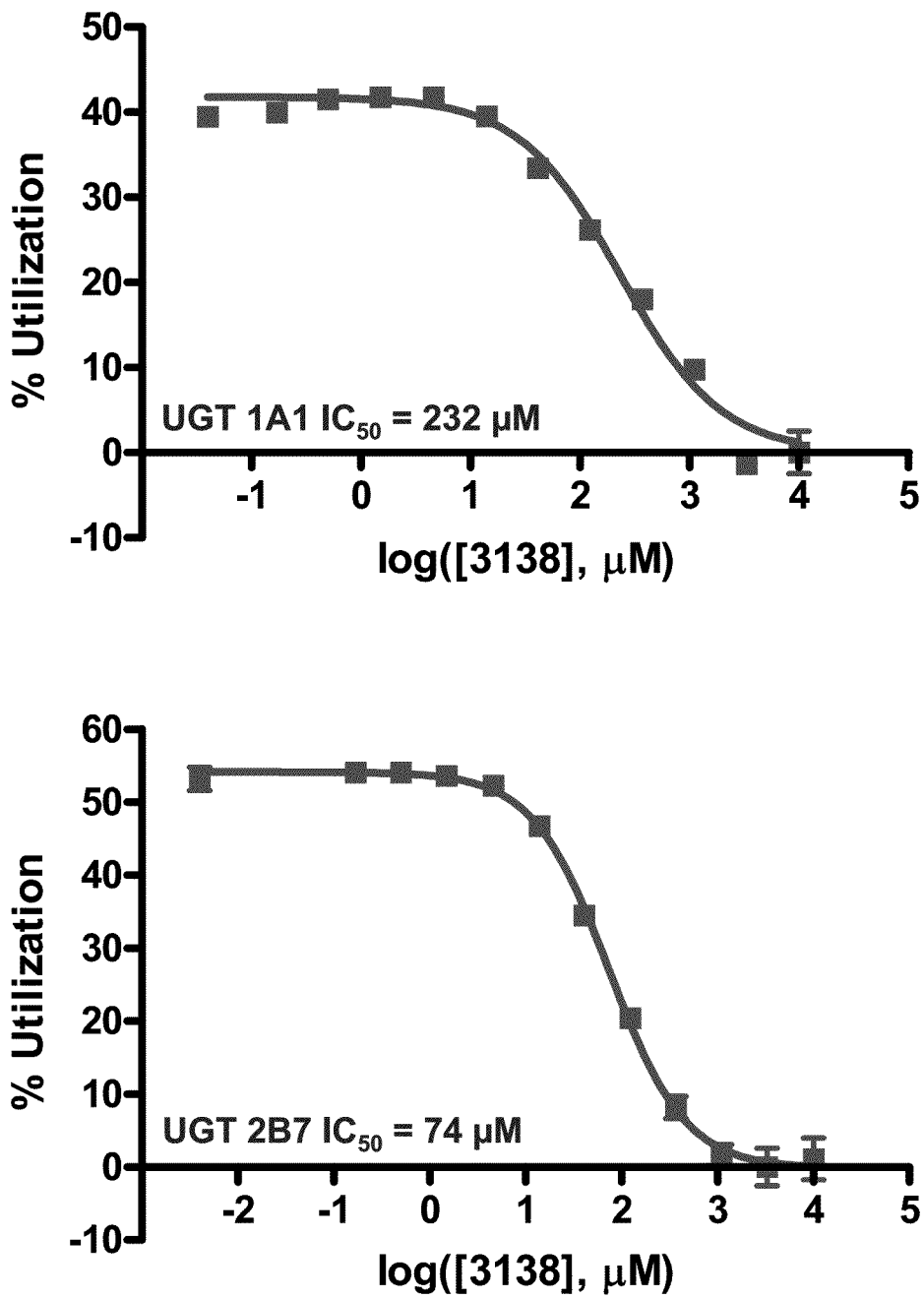
FIG. 10 illustrates diclofenac inhibition curves for UGT 1A1 (top) and UGT 2B7 (bottom) with the respective IC50 values, according to an aspect of the invention.
Figure 11:
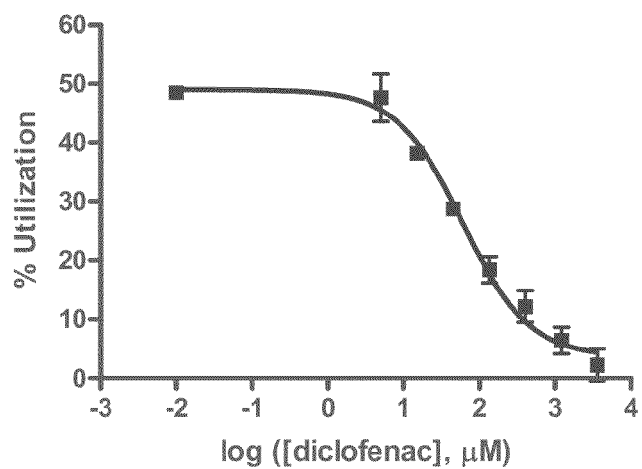
FIG. 11 illustrates inhibition of HLM utilization of compound 3138 by diclofenac with an $IC_{50}$ of 60 µM, according to an aspect of the invention.

The titration curves are shown in FIG. 10 (for recombinant Supersomes) and 11 (for HLM). Diclofenac inhibited UGT 1A1 activity with an $IC_{50}$ of 232 µM and UGT 2B7 activity with an $IC_{50}$ of 74 µM. This is consistent with literature reports that UGT 2B7 is inhibited more potently than UGT 1A1 by diclofenac when using 4-methyl-umbelliferone as the substrate (see Uchaipichat et al. *Drug Metab. Disp.* (2004). 32:4, 413-423). Diclofenac inhibited HLM utilization of compound 3138 with an $IC_{50}$ of 60 µM. This example shows the utility of the assay for screening for inhibition using both recombinant UGT Supersome preparations and the more native human liver microsome environment.

Example 5

Inhibition of UGT Activities in Human Liver Microsomes

Many compounds are known to modulate the activity of specific UGT isozymes. Several of these were tested in the assay system described herein to measure their ability to inhibit UGT activity in human liver microsomes (HLM) as measured using compound 3138. The inhibitor compounds, as well as a listing of isozymes currently reported in the literature to be modulated by the compound, are show in the table below.

| Compound | Isozymes Modulated |
|---|---|
| Sulfinpyrazone | 1A1, 1A7, 1A8, 1A9, 1A10, others to a lesser extent |
| Quinidine | 2B7 and 2B15, others to a lesser extent |
| 1-Naphthol | 1A1, 1A4, 1A6, 1A9 |
| Scopoletin | 1A3, 1A8, 1A9, 1A10, 2B17 |
| Androsterone | 1A1, 1A3, 1A4, 1A9, 1A10, 2B4, 2B7, 2B15 |
| Umbelliferne | Substrate of most isozymes |
| 7-hydroxy-4-trifluoromethyl coumarin | Substrate for 1A1, 1A3, 1A6, 1A9, 2B7 |
| Ritonavir | 1A1, 1A3, 1A4 |
| Lopinavir | 1A1, 1A3, 1A4 |
| Diclofenac | Inhibits most isozymes |
| Valproate | 2B7 and 2B15, some others to a lesser extent |

To assess the ability of these compounds to inhibit UGT activity in HLM, reactions were set up as follows. All reactions contained 50 mM TES, pH 7.5, 8 mM $MgCl_2$, 25 µg/mL alamethicin, 0.05 mg/mL HLM, and 50 µM compound 3138, plus or minus 4 mM UDPGA. Ritonavir and lopinavir were used at a final concentration of 0.25 mM. Sulfinpyrazone, quinidine, and androsterone were used at a final concentration of 0.5 mM. 1-Naphthol, scopoletin, umbelliferne, and 7-hydroxy-4-trifluoromethyl coumarin were used at a final concentration of 1 mM. Diclofenac was used at a final concentration of 5 mM. Valproate was used at a final concentration of 10 mM. All reactions were compared to their corresponding vehicle control sample containing either water, DMSO, or ethanol. After 15 min at 37° C., 40 µL of P450-Glo LDR plus 20 mM D-cysteine was added to each 40 µL reaction and mixed. After 20 minutes at room temperature, bioluminescence was measured on a luminometer.

Figure 13:
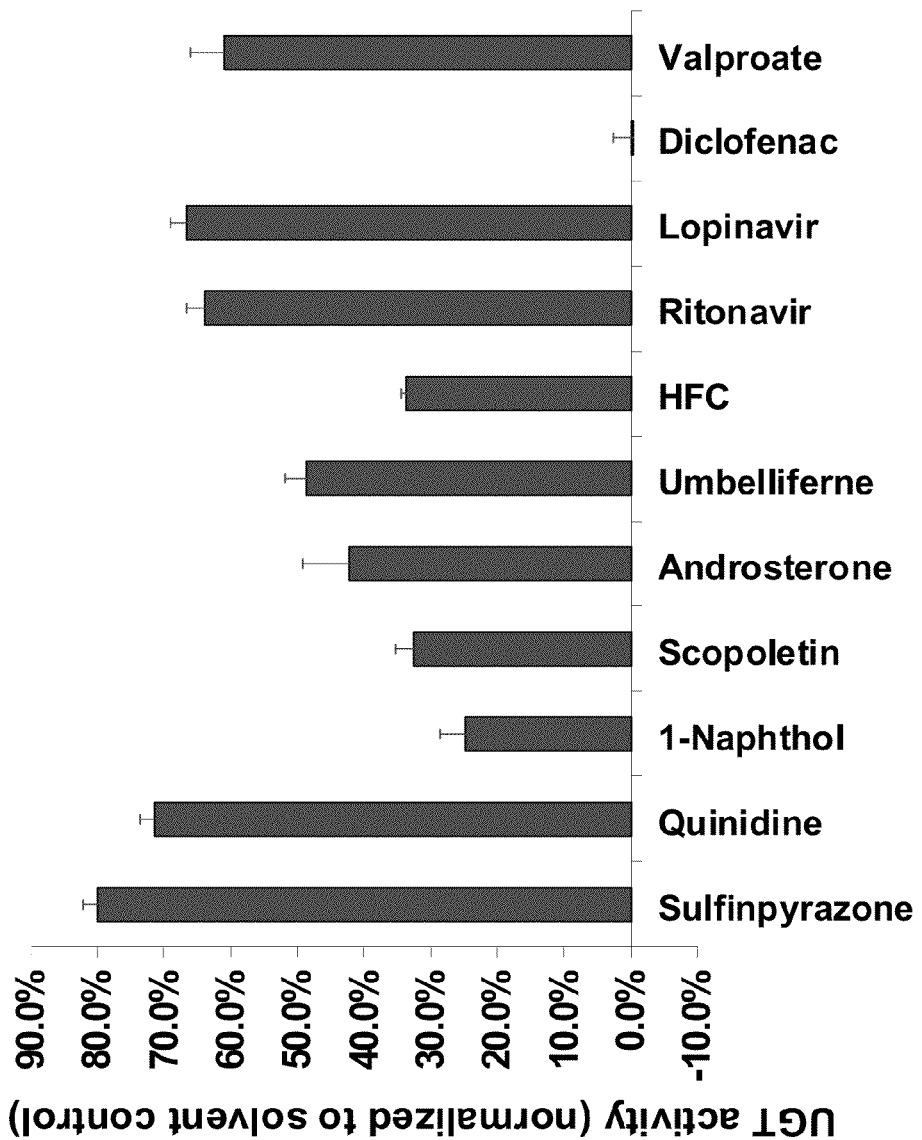
FIG. 13 illustrates inhibition of UGT activity in HLM by various compounds, according to an aspect of the invention.
Figure 14:
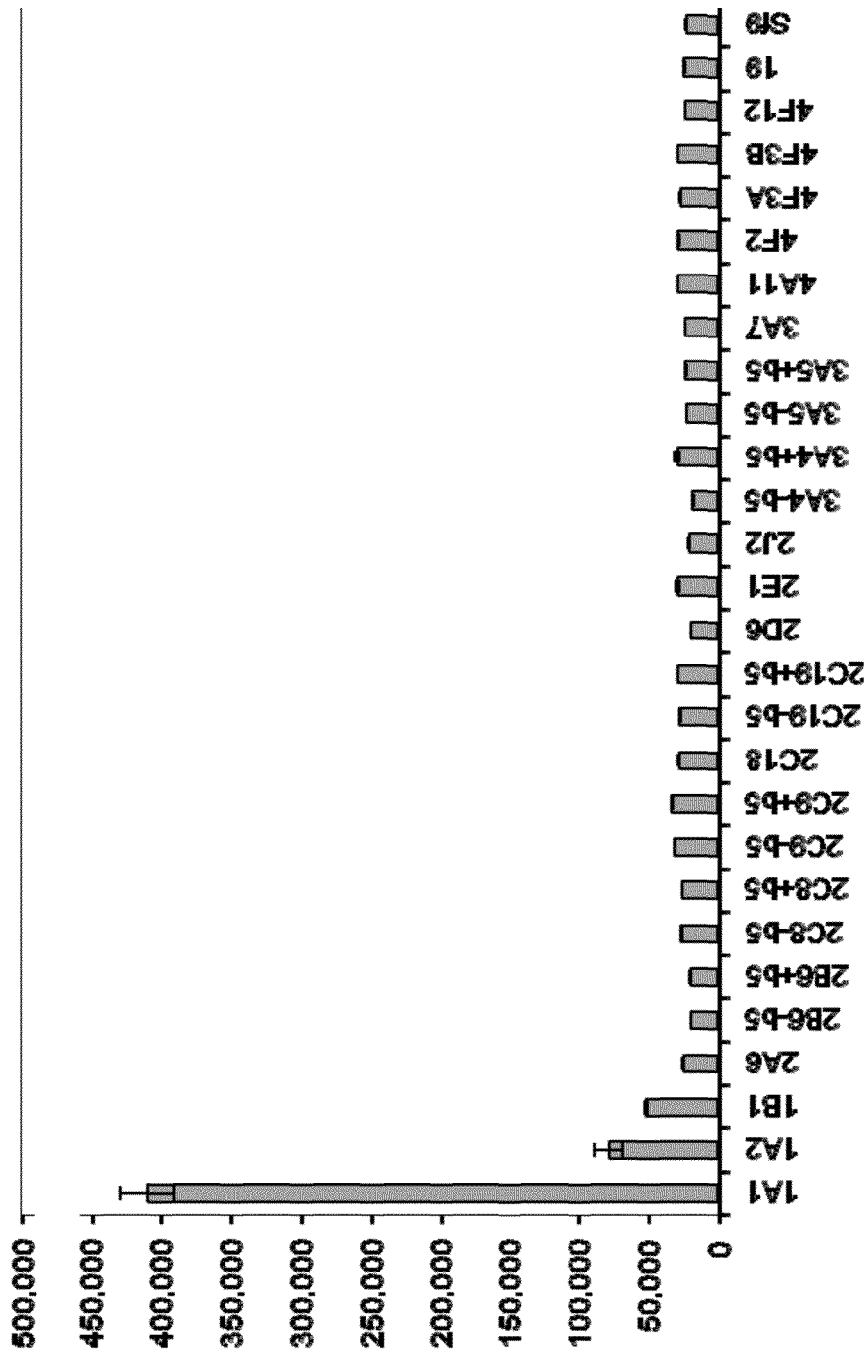
FIGS. 14-25 illustrate the selective detection of CYP450 enzyme activity as light output (recorded by a Veritas™ luminometer), as described by Example 9, for benzothiazole derivative compounds 3016, 3019, 3026, 3806, 3814, 3820, 3821, 3833, 3835, 3866, and 3868, according to an aspect of the invention. The Y-axis indicates relative light units (RLU).
Figure 15:
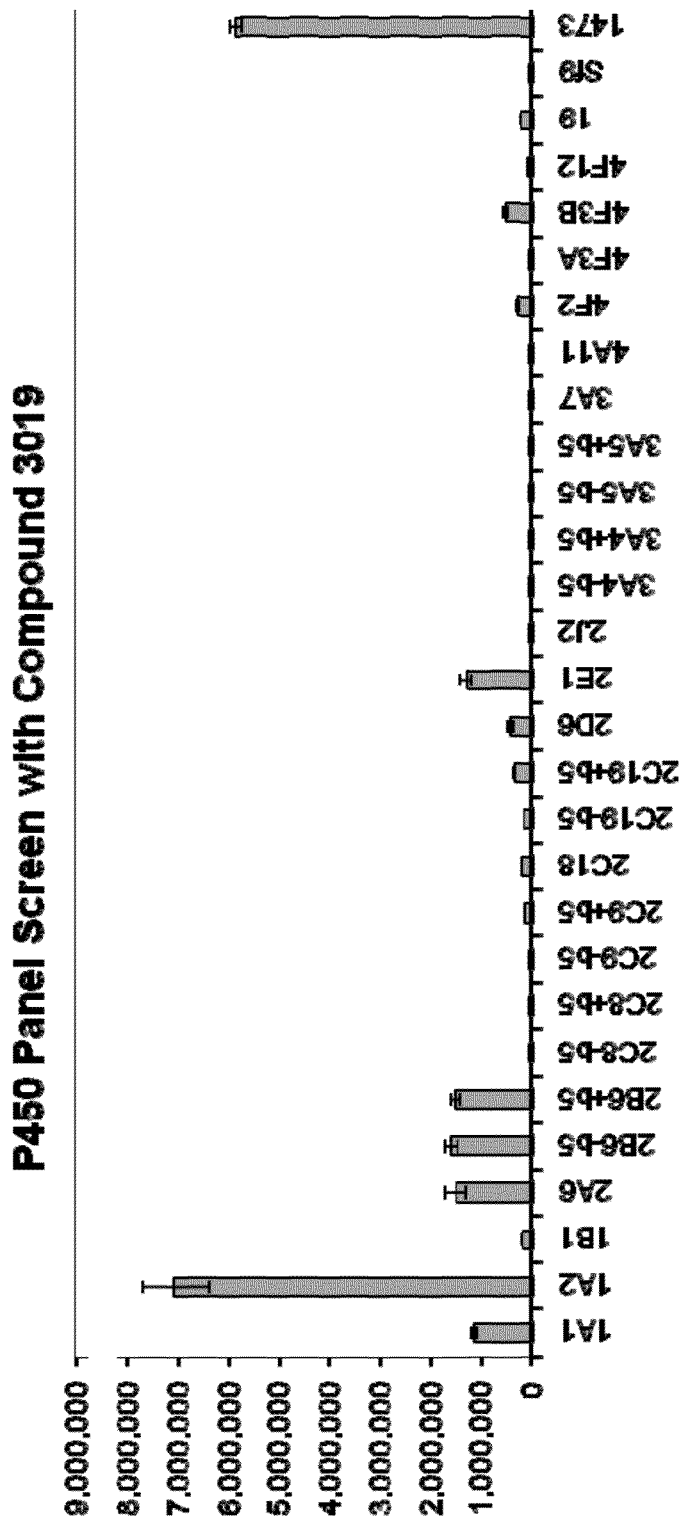
Figure 16:
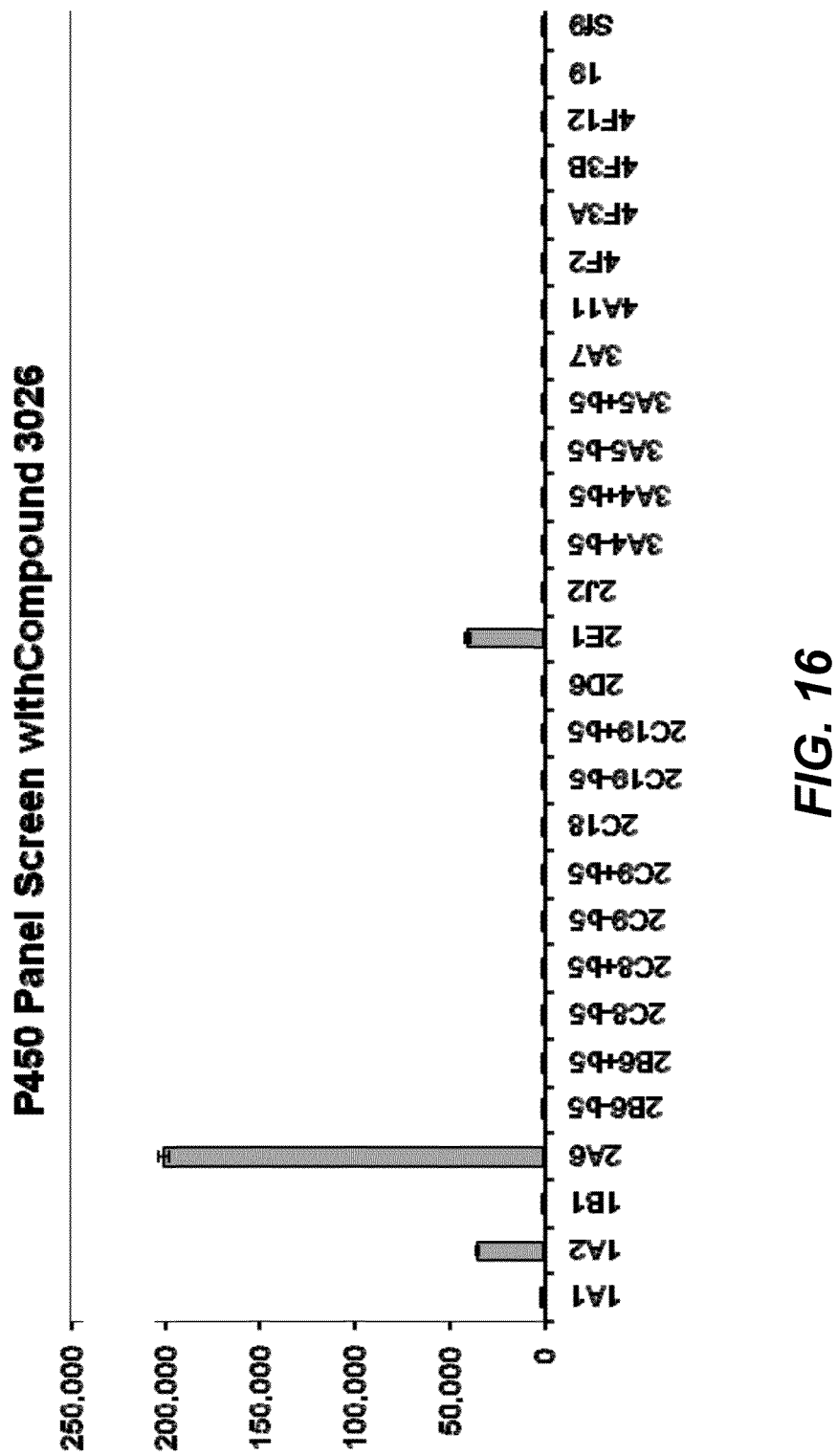
Figure 17:
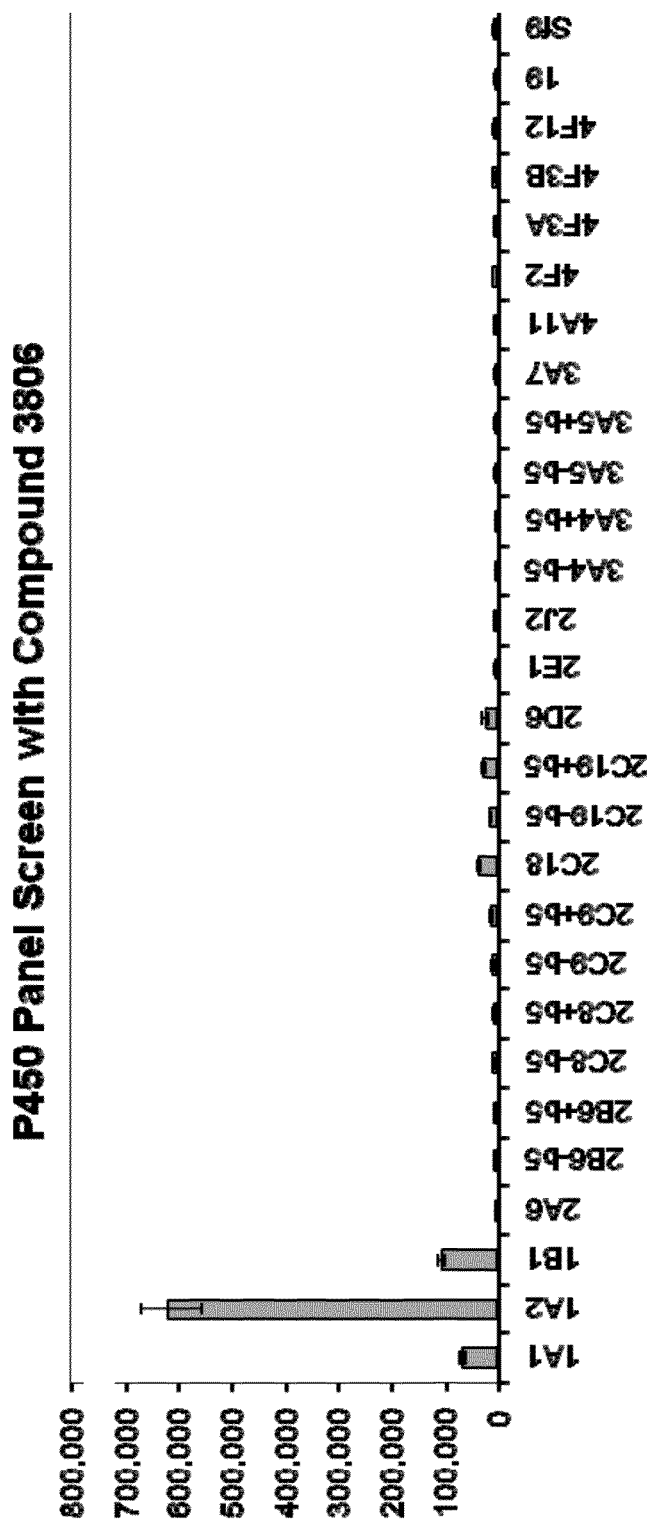
Figure 18:
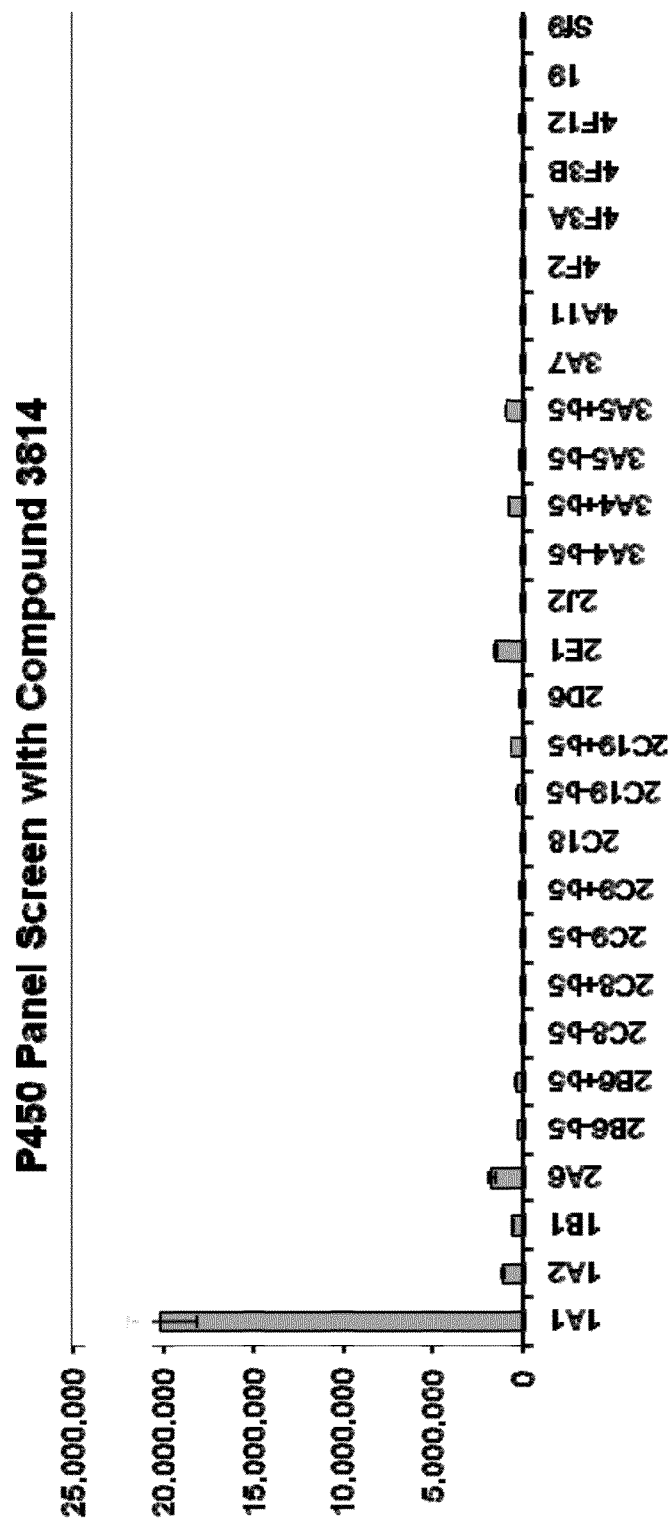
Figure 19:
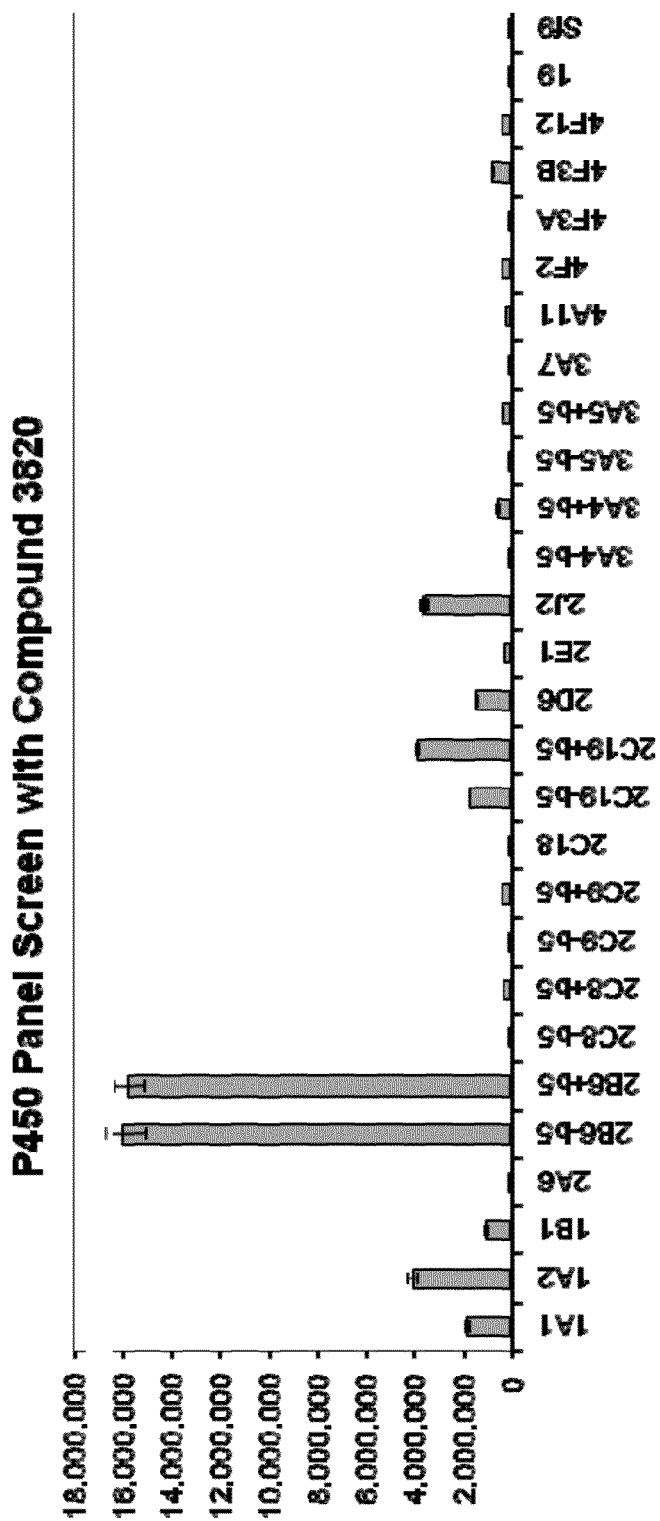
Figure 20:
Figure 21:
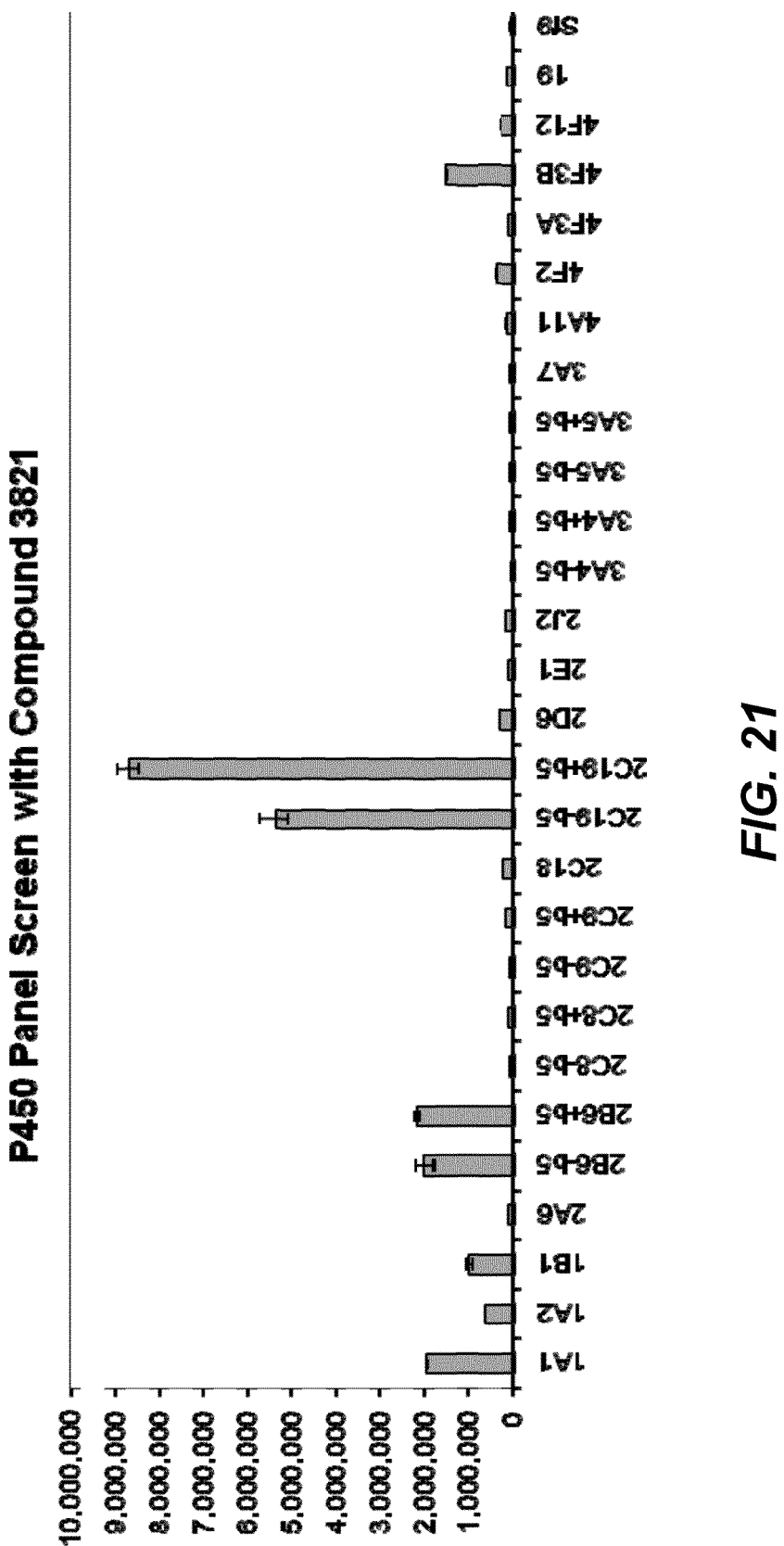
Figure 22:
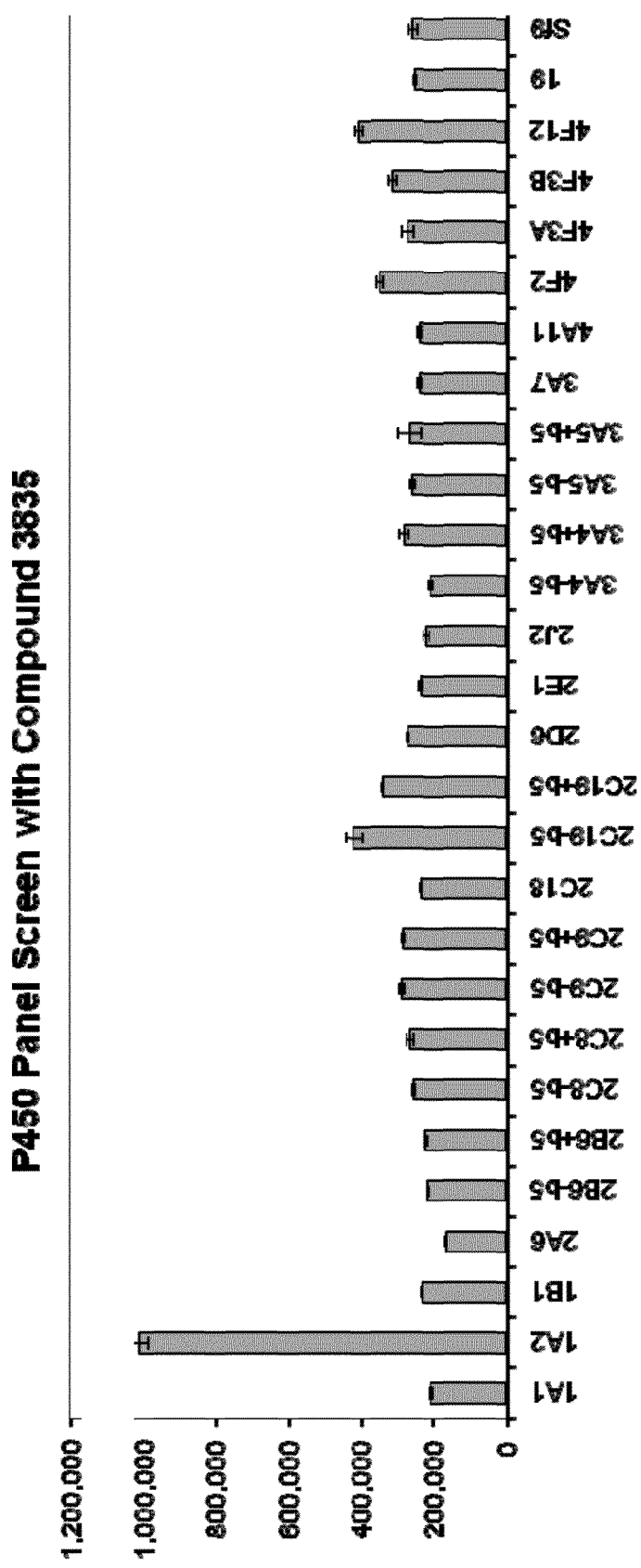
Figure 23:
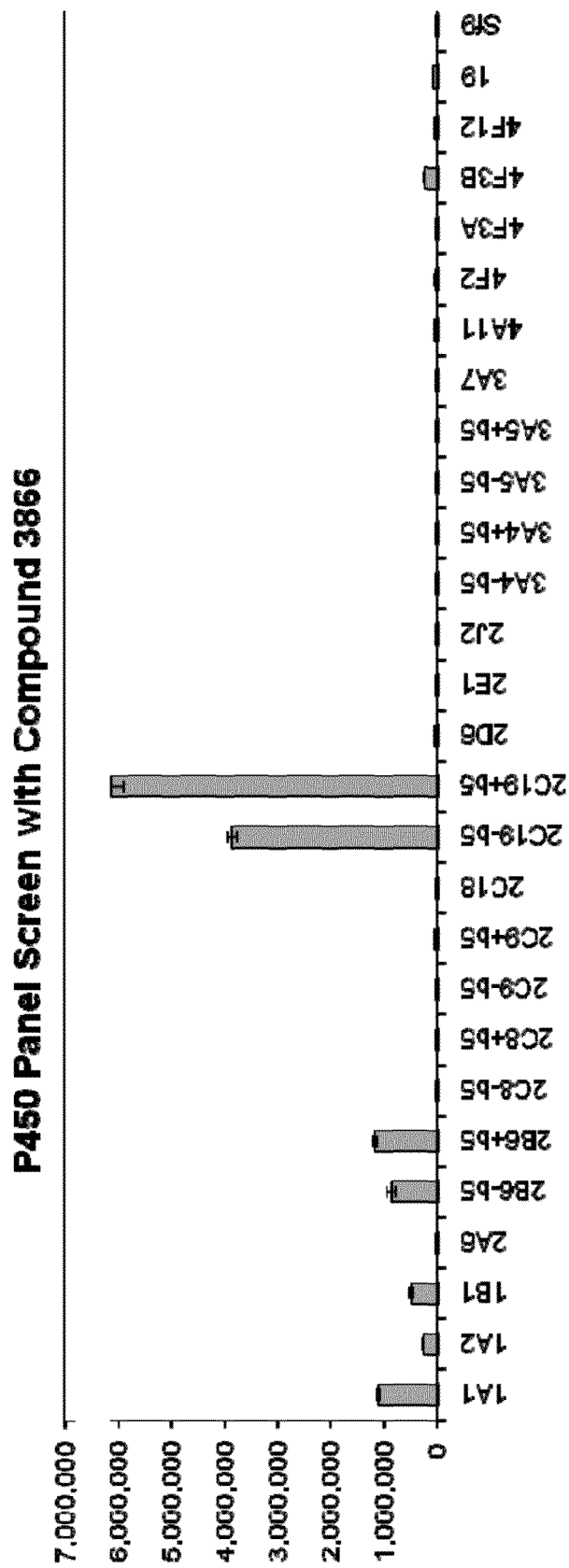
Figure 24:
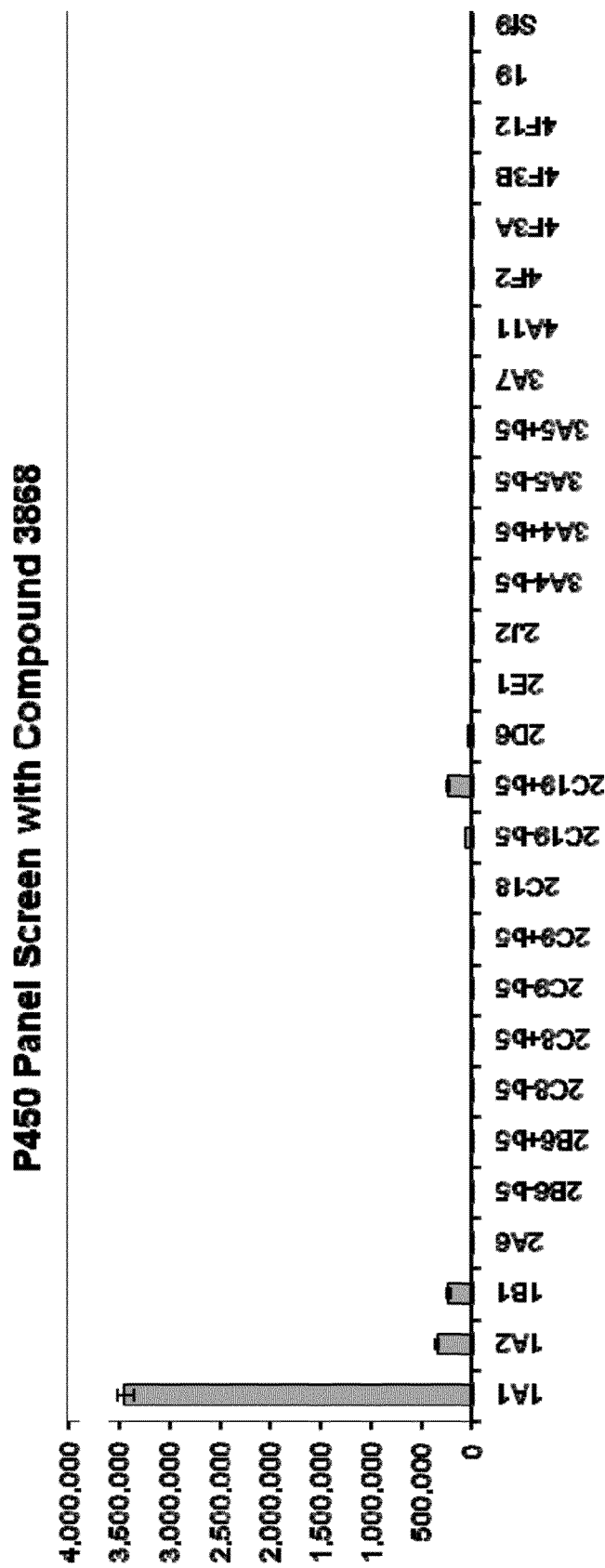
Figure 25:
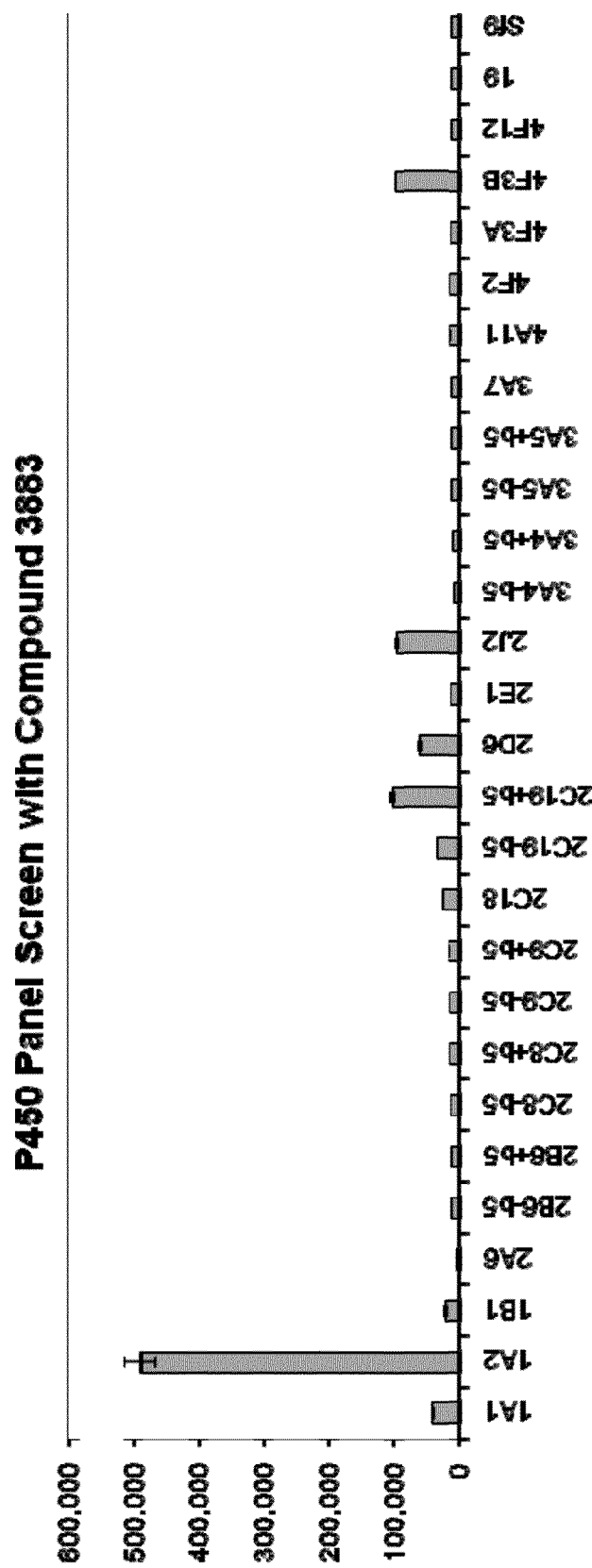

The compounds inhibited UGT activity in HLM to various degrees (FIG. 13). This example shows the utility of the assay for screening for a variety of UGT inhibitors in the more native human liver microsome environment.

Example 6

Determination of Assay Variability Using UGT 1A1 and 2B7

Assay variability was determined using the activity data and standard deviations of 12 separate no UDPGA and plus UDPGA samples. All reactions contained 50 mM TES, pH 7.5, 8 mM $MgCl_2$, 25 µg/mL alamethicin, 0.2 mg/mL UGT 1A1 or 2B7 Supersomes™, and 30 µM compound 3138, plus or minus 5 mM UDPGA. After 120 min at 37° C., 40 µL of P450-Glo LDR plus 20 mM D-cysteine was added to each 40 µL reaction and mixed. After 20 minutes at room temperature, bioluminescence was measured on a luminometer.

Figure 12:
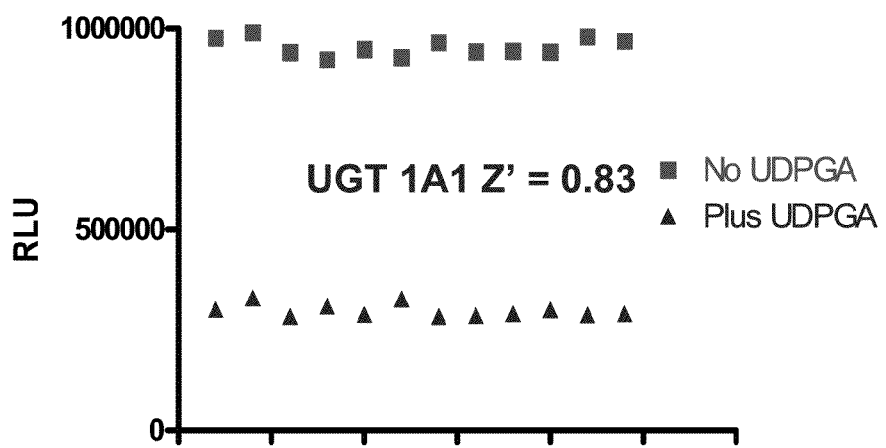
FIG. 12 illustrates data for UGT 1A1 for determining assay variability, according to an aspect of the invention.

Data for UGT 1A1 is shown in FIG. 12. Z' values were calculated using the equation outlined below.

$$Z' = 1 - \frac{(3 * stdev_{noUDPGA} + 3 * stdev_{plusUDPGA})}{(RLU_{noUDPGA} - RLU_{plusUDPGA})}$$

Robust assay systems typically display Z' values of 0.5 or higher. The calculated Z' value for UGT 1A1 was 0.83. The calculated Z' value for UGT 2B7 under the same conditions was 0.67.

Example 7

Utilization of Benzothiazoles by GST Isozymes

Compound 934-37 was dissolved in DMSO to produce a solution approximately 1 mg/mL. This solution was diluted 1:100 (v/v) into 50 mM HEPES buffer pH 7.5 to produce a substrate solution (approximately 10 μg/ml). Twenty μL of this solution was placed in 10 wells of a 96 well, white luminometer plate (Promega part Z3291), 20 μL of a 1:3.1 dilution of the substrate (approximately 3.2 μg/ml) was placed into another 10 wells in the luminometer plate.

D-Cysteine, 4 mg (Sigma Chemical Corp.; C8005-1g, 017K1034) was dissolved into 1 mL of 50 mM HEPES buffer pH 7.5, then 4 μL added to 4 of the wells containing the substrate solution and 4 of the wells with diluted substrate solution to convert compound 934-37 to the corresponding luciferin derivative. The structures of these compounds are shown below.

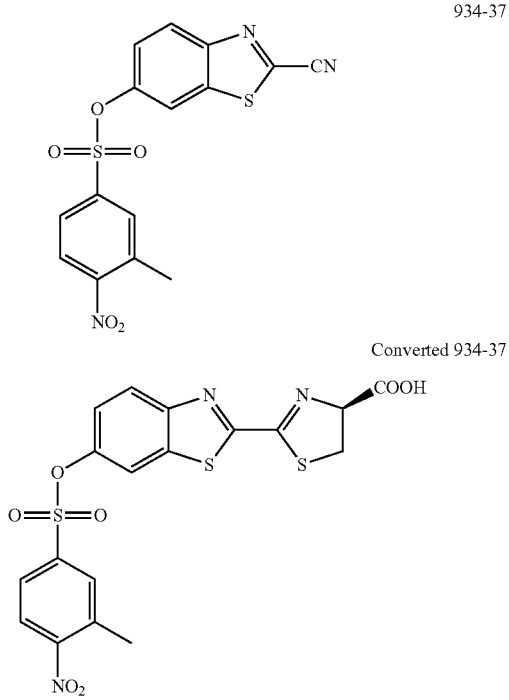

A sample of glutathione S-transferase isoenzyme A1-1 (GST A1-1) (1.2 mg/mL) and 100 μL of 100 mM glutathione in water was diluted into 5 mL of 50 mM HEPES pH 7.5, then 25 μL added to the plate as follows: 2 wells with unconverted, concentrated compound 934-37; 2 wells with concentrated and converted compound 934-37; 2 wells with unconverted, diluted compound 934-37; and 2 of the wells with converted, diluted compound 934-37.

A sample of GST M1-1 (1.2 mg/mL) and 100 μL of 100 mM glutathione was diluted into 5 mL of 50 mM HEPES pH 7.5, then 25 μL added to: two of the wells with unconverted, concentrated compound 934-37; 2 wells with concentrated and converted compound 934-37; and two of the wells with unconverted, diluted compound 934-37 and 2 of the wells with converted, diluted compound 934-37.

Glutathione (100 μL of 100 mM glutathione) had been diluted to 5 mL with 50 mM HEPES buffer pH 7.5, then 25 μL added to the remaining wells of converted and unconverted compound 934-37 in concentrated and diluted solution.

After 55 minutes at room temperature, 4 μL of the D-cysteine solution above was added to all wells that had not received cysteine before, then 50 μL of P450-Glo LDR was added. The plate was then placed into a GloMax luminometer (Promega Corp.), and the bioluminescence measured after 15 minutes of incubation. The values obtained were averaged, and the average value of the bioluminescence produced from the wells with no enzyme were then subtracted from the average of the bioluminescence produced in the wells with enzyme. The results are presented in the table below.

| Reaction | GST A1-1 | GST M1-1 |
| --- | --- | --- |
| Concentrated, untransformed substrate | 164,400 RLU | 41,212 RLU |
| Diluted, untransformed substrate | 195,021 RLU | 30,428 RLU |
| Concentrated, transformed substrate | 6,410 RLU | 315,759 RLU |
| Diluted, transformed substrate | 6,462 RLU | 213,920 RLU |

These data clearly show that GST A1-1 utilizes the substrate to a much faster rate in its untransformed state and essentially loses the ability to convert the material once it is converted to a luciferin derivative by addition of D-Cys. However GST M1-1 shows much less ability to utilize the material in its unconverted state but utilizes the converted form of the substrate very well. This difference in utilization of the converted and unconverted forms can be used to determine if a sample contains one or both of these isozymes.

Example 8

Synthesis Of N-Peptidyl-6-Amino-2-Cyanobenzothiazoles

Protected N-peptidyl-6-amino-2-cyanobenzothiazoles can be prepared as described in U.S. Pat. No. 7,384,758 (O'Brien et al.). Deprotected derivatives can be prepared as follows.

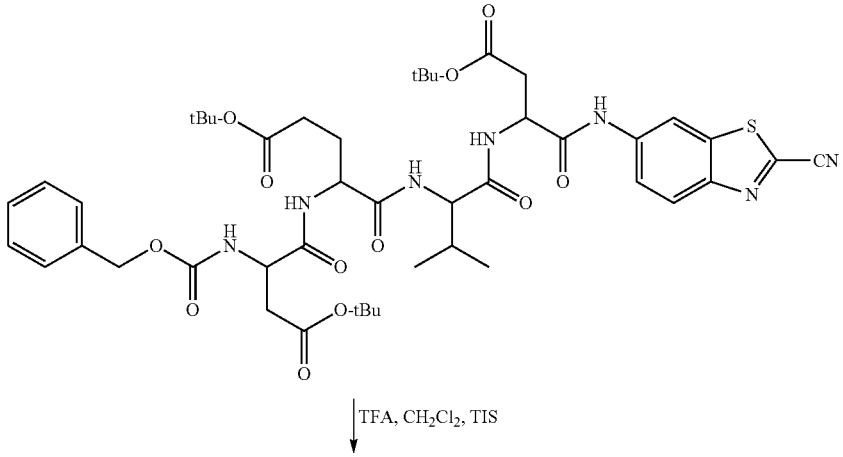

-continued

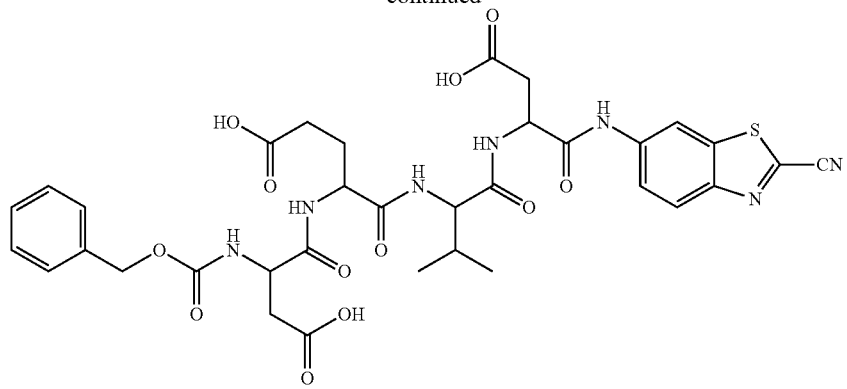

To an anhydrous solution of trifluoroacetic acid/dichloromethane/triisopropyl silane (50/50/2) is added the t-butyl protected N-peptidyl-6-amino-2-cyanobenzothiazole (U.S. Pat. No. 7,384,758). After 2 h, evaporate the solution to a syrup. Precipitate with diethyl ether. Wash solid twice with ethyl ether. Dry under vacuum. Purify on reverse-phase HPLC eluting with 20 mM NH4OAc. Combine appropriate fractions and lyophilize to provide the de-tBu-protected compound. Removal of the Cbz group can be achieved under hydrogenation conditions (e.g., hydrogen gas in the presence of Pd/C)

Example 9

Cytochrome P450 Enzyme Panel Screen: Utilization of Benzothiazoles by Cytochrome P450 Enzymes Several cyanobenzothiazole derivatives were synthesized and screened against a panel of recombinant CYP450 enzymes expressed in an insect cell/baculovirus expression system. All the CYP450s were co-expressed with the requisite co-factor P450 reductase. Some also were co-expressed with cytochrome b5 to enhance activity. Stock solutions of the benzothiazole compounds 3016, 3019, 3026, 3806, 3814, 3820, 3821, 3833, 3835, 3866, and 3868, 3823, 3023, 3828, 3017, 3018, 3020, 3021, 3022, 3024, 3815, 3817, 3822, 3824, 3825, 3826, 3827, 3829, 3830, 3851, 3852, 3891, 3907 were made at 50 mM in DMSO. One picomole of each CYP450 enzyme (20 nM final concentration in the reactions) (Supersomes™, BD Bioscience) was incubated with 50 μM of each of the compounds in a 50 μL reaction in $KPO_4$ buffer pH 7.4 (25 mM $KPO_4$ for CYP450-2C9, 50 mM $KPO_4$ for CYP450-2B6, -2C8, -2C19, -4F2, -4F3A and -4F3B, 100 mM $KPO_4$ for CYP450-1A1, -1A2, -1B1, -2D6, -2E1, -3A5, -3A7, -2J2, -4F12, -19 and minus P450 control, 200 mM $KPO_4$ for CYP450-3A4) or 100 mM Tris-HCl, pH 7.5 (for CYP450-2A6, -2C18 and -4A11). Reactions were initiated by adding an NADPH regenerating system (final concentrations: 1.3 mM $NADP^+$, 3.3 mM glucose-6-phosphate, 3.3 mM $MgCl_2$, 0.4 U/mL glucose-6-phosphate dehydrogenase and 0.05 mM sodium citrate). Reactions were incubated for 30 minutes at 37° C. After incubation, 50 μL of P450-Glo™ LDR (Promega Corp.) supplemented with 6.6 mM D-cysteine was added to each reaction, incubated at room temperature for 20 minutes, and bioluminescence measured on a Veritas luminometer. Some of the compounds were also re-screened using lower concentrations of the compounds. The lower concentrations of the CYP450 enzymes allowed the identification of conditions for more restricted cross-reactivity profiles for the compounds (e.g. compound 3019). The data shown in the table of FIG. 33 demonstrates that the benzothiazole compounds can be used to detect CYP450 enzyme activity as bioluminescence in the present invention. Each compound was active with one or more CYP450 enzymes, and the profile of CYP450 activity varied across the panel of enzymes depending on the compound structure. The bioluminescence specific to a given CYP450 enzyme can be due to oxidation of the benzothiazole compound by the P450 enzyme to yield 6-hydroxybenzo[d]thiazole-2-carbonitrile (a benzothiazole derivative). The 6-hydroxybenzo-[d]thiazole-2-carbonitrile can then react with D-cysteine to form a D-luciferin derivative that in turns reacts with luciferase in the luciferin detection reagent to generate light in proportion to the amount of D-luciferin present.

Example 10

Figure 26:
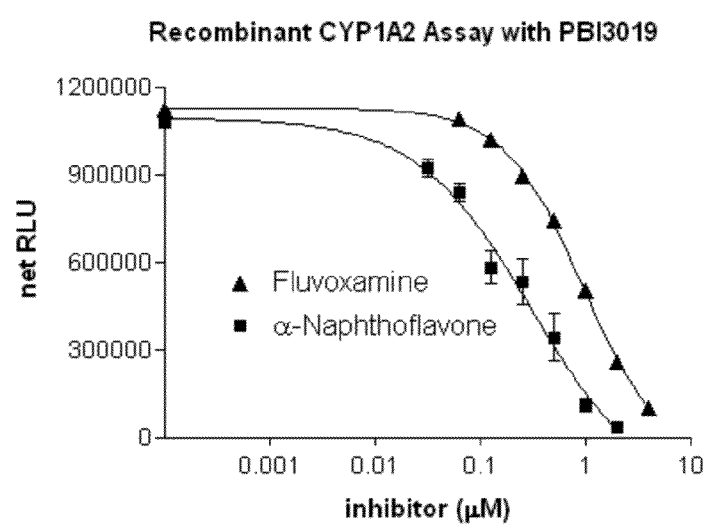
FIG. 26 illustrates the dose dependent inhibition of compound 3019 CYP1A2 activity by α-naphthoflavone and fluvoxamine.
Figure 27:
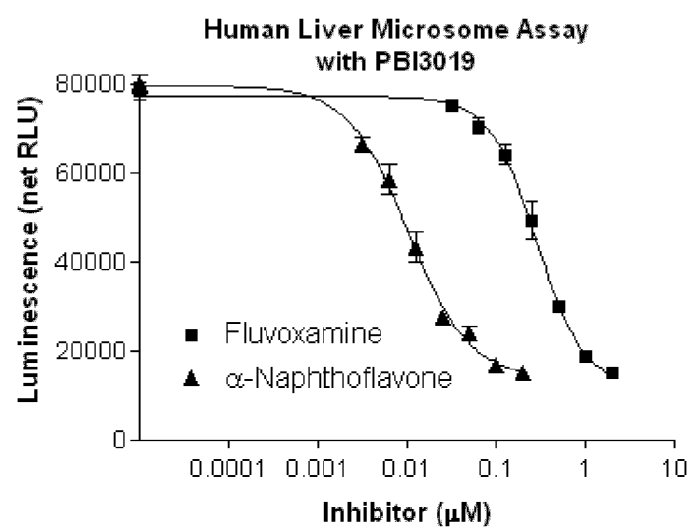
FIG. 27 illustrates the sensitivity of a compound 3019 human liver microsome reaction to inhibition by α-naphthoflavone and fluvoxamine.

Human recombinant CYP450 1A2 and human liver microsomes (BD Biosciences) were incubated with compound 3019 for 10 minutes at 37° C. in 50 μl reaction volume with 100 mM $KPO_4$ pH 7.4 and with doses of α-naphthoflavone and fluvoxamine. For the recombinant CYP1A2 assay, 0.5 pmole of CYP450 1A2 and 6 μM of compound 3019 were used. For the human liver microsomes (HLM) assay, 1 μg of HLM and 3 μM compound 3019 were used. Equal volumes of P450-Glo LDR with 6.6 mM D-Cysteine was added into the CYP450 reactions. After 20 minutes of incubation at the room temperature, the bioluminescence was measured on a luminometer. α-naphthoflavone and fluvoxamine, known CYP450 1A2 inhibitors, caused dose-dependent inhibition of the recombinant CYP450 1A2 activity (FIG. 26). There was substantial activity with compound 3019 in human liver microsomes (HLMs), and this activity was also sensitive to inhibition by α-naphthoflavone and fluvoxamine (FIG. 27). While the initial CYP450 enzyme panel screen and the recombinant CYP450 1A2 inhibition assays show that compound 3019 is indeed a CYP450 1A2 substrate that can also be used to detect CYP1A2 inhibition, the effect of CYP450 1A2 selective inhibitors on HLM activity confirms that compound 3019 shows a substantial degree of CYP450 1A2 selectivity in the a complex mixture of different CYP450 enzymes.

Example 11

Human cryopreserved hepatocytes (Celsis lot RTM) were thawed and seeded in hepatocyte culture medium in wells of a collagen-coated, 96-well culture plate at ~80,000 cells per well and kept at 37° C. in standard cell culture incubator with 5% $CO_2$. The cells were then treated for 48 hours with 100 µM omeprazole, 25 µM rifampicin, 1 mM phenobarbital or vehicle control (0.1% dimethylsulfoxide) dissolved in hepatocytes culture medium (FIG. 28, n=3 for each treatment, mean values and standard deviations are shown). Cells were then rinsed twice with Krebs-Henseleit (KH) buffer and incubated for 1 hour with 6 µM compound 3019, 3 mM salicylamide and 0.3% dimethylsulfoxide in 100 µl KH buffer. The plate was then removed from the incubator and 100 µl of P450-Glo LDR with esterase either with 6.6 mM D-cysteine (left graph) or without D-cysteine (right graph), was added to each well to produce a lysate. 100 µl of the lysate was transferred from each well of the culture plate to a well of a white, 96-well luminometer plate (Costar). After 20 minutes at room temperature (~21° C.), bioluminescence was measured on plate reading luminometer (Veritas).

The samples without D-cysteine were included in order to gain insight into the impact of native cysteine present inside the cells. Endogenous cysteine is present in cells as L-cysteine, and cyclization with L-cysteine would produce L-luciferin, which is generally considered to be an inhibitor rather than an effective substrate for firefly luciferase (D-luciferin is the main active form of substrate for firefly luciferase). Although the presence of endogenous L-cysteine might have been expected to interfere with the assay, the assay results indicate that this, to the extent of undermining the assay, did not occur as robust basal and induced signals were observed.

Figure 28:
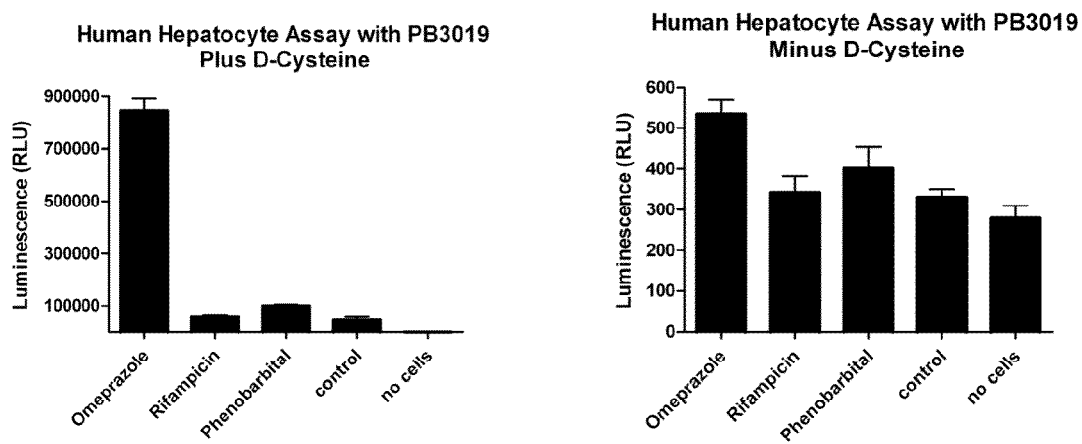
FIG. 28 illustrates the light output from the human hepatocyte assays with compound 3019.

Results from samples containing cells and no D-cysteine, the only source of L-cysteine in this system, were similar to the no cells background control. This indicates that conversion of L-luciferin to D-luciferin did not contribute significantly to the total signals observed in plus D-cysteine samples (FIG. 28).

Example 12

Non-Lytic Cell-Based Assay with Human Hepatocytes

Human cryopreserved hepatocytes (Celsis lot RTM) were thawed and seeded in hepatocyte culture medium in wells of a collagen-coated, 96-well culture plate at ~70,000 cells per well and kept at 37° C. in standard cell culture incubator with 5% $CO_2$. The cells were then treated for 48 hours with 100 µM omeprazole or vehicle control (0.1% dimethylsulfoxide) dissolved in hepatocytes culture medium (n=3 for each treatment, mean values and standard deviations are shown). Cells were then rinsed twice with Krebs-Henseleit (KH) buffer, then incubated for 1 hour with 3 µM compound 3019, 3 mM salicylamide and 0.3% dimethylsulfoxide in 100 µl KH buffer. 50 µl of the KH incubation buffer was then removed from each well and transferred to a well of a white, 96-well luminometer plate (Costar) where it was also combined with 50 µl of P450-Glo LDR containing 6.6 mM D-cysteine. After 20 minutes at room temperature (~21° C.), bioluminescence was measured on a plate reading luminometer (Veritas).

Figure 29:
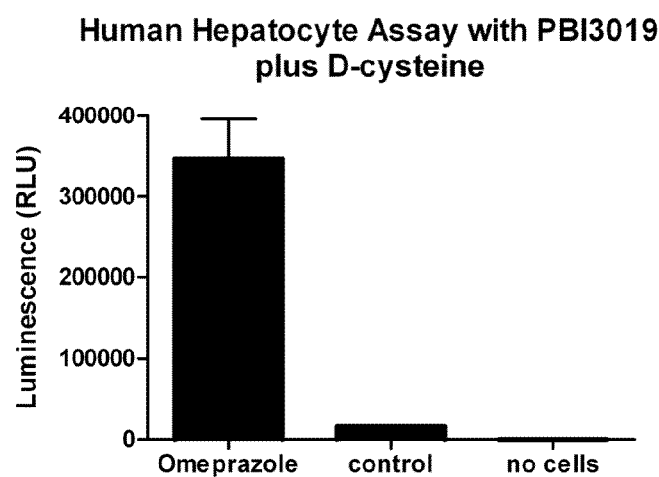
FIG. 29 illustrates the light output from the non-lytic human hepatocyte assay with compound 3019.

The results shown in FIG. 29 indicate that the compound 3019 entered the cell, and the CYP450 reaction product and unreacted compound 3019 exit the cells. As seen in FIG. 29, a basal signal was observed from cells that received vehicle only treatment and that signal was significantly increased from cells treated with the CYP1A2 inducer omeprazole.

Example 13

Non-Lytic Assay with Rat Hepatocytes

Following the non-lytic approach described in Example 13, cryopreserved rat hepatocytes (Xenotech lot R1000) were thawed and seeded in hepatocyte culture medium in wells of a collagen-coated 96-well culture plate at ~50,000 cells per well and kept at 37° C. in standard cell culture incubator with 5% $CO_2$. The cells were then treated for 48 hours with 10 nM 2,3,7,8-tetrachlorodibenzo-p-dioxin (TCDD) or vehicle control (0.006% dimethylsulfoxide) dissolved in hepatocytes culture medium (n=3 for each treatment, mean values and standard deviations are shown). Cells were then rinsed twice with Krebs-Henseleit (KH) buffer, then incubated for 1 hour with 3 µM compound 3019, 3 mM salicylamide and 0.3% dimethylsulfoxide in 100 microliter KH buffer. 50 µl of the KH incubation buffer was then removed from each well and transferred to a well of a white 96-well luminometer plate (Costar) where it was also combined with 50 µl of luciferase reaction mixture (as described above) containing 6.6 mM D-cysteine. After 20 minutes at room temperature (~21° C.), bioluminescence was measured on a plate reading luminometer (Veritas).

Figure 30:
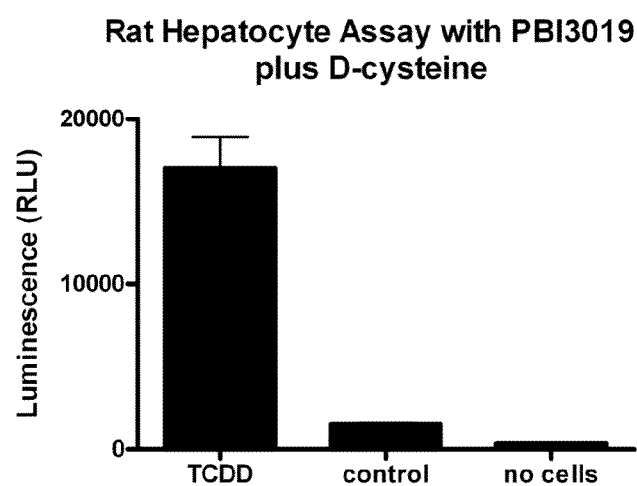
FIG. 30 illustrates the light output from the non-lytic rat hepatocyte assay with compound 3019.

Like with human hepatocytes, the results shown in FIG. 30 show a significant basal signal was observed that was significantly increased by the CYP450 1A2 inducer 2,3,7,8-tetrachlorodibenzo-p-dioxin (TCDD). TCDD is a dioxin derivative that induces genes through a mechanism that involves its binding to the aryl hydrocarbon nuclear receptor. The CYP450 1A class of genes are among the group that are responsive to this pathway and, given other evidence presented here pointing to the CYP1A2 selectivity of the compound 3019, the signal increase caused by TCDD is consistent with rat CYP1A2 gene induction.

Example 14

Figure 31:
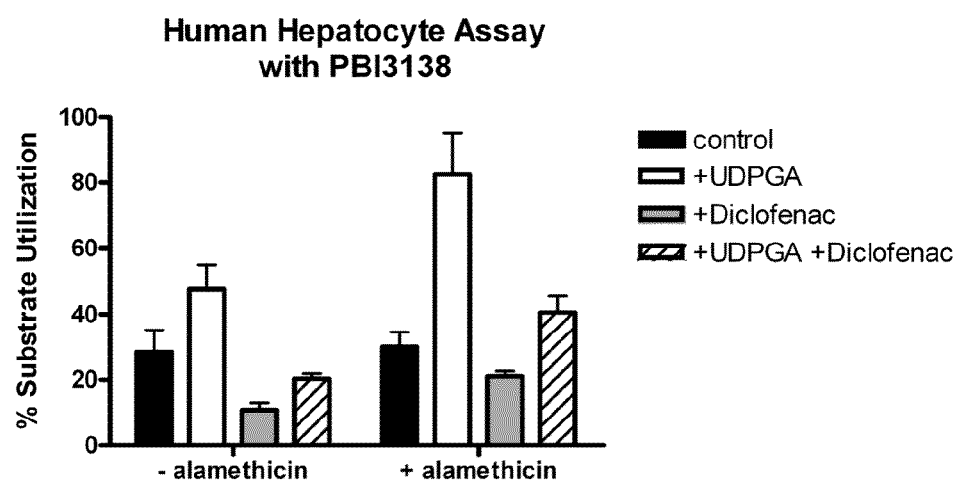
FIG. 31 illustrates substrate utilization in a human hepatocyte assay with compound 3138.

Cryopreserved human hepatocytes (ADMET Technologies lot #H2063-P10) were thawed, resuspended in Krebs-Henseleit (KH) buffer, and dispensed at ~60,000 cells per well (50 µl of the suspension) in white 96-well luminometer plates. 50 microliters of 50 mM TES buffer containing 100 µM compound 3138 (shown in FIG. 32) alone (control) or in combination with 8 mM uridine 5'-diphospho-glucuronic acid (UDPGA), 4 mM diclofenac or UDPGA and diclofenac was then added and allowed to incubate for 15-20 minutes at 37° C. 100 µl of P450-Glo LDR containing 20 mM D-cysteine was then added. After 20 minutes at room temperature (~21° C.), bioluminescence was measured on a plate reading luminometer. Results are shown in FIG. 31, "% substrate utilization" reflects the decrease in bioluminescence observed relative to cell free controls (e.g. 20% utilization refers to a 20% decrease in light output compared to the corresponding no-cells control). Values are means and standard deviation where n=3 for control, +UDPGA, and +diclofenac; and n=2 for +UDPGA +diclofenac.

Conversion of the PBI 3138 was seen upon incubation of the intact hepatocytes. Addition of UDPGA increased this conversion in the presence of the cell permeabilizing agent Alamethacin. This conversion was inhibited by the presence of diclofenac, as was to be expected for a conversion catalyzed by a UGT isozymes (as discussed above). This inhibition was also seen even if additional UDPGA was added in the presence of Alamethacin. These results indicate that addition of PBI 3138 to these cells did result in conversion of the PBI 3138 to a modified compound as was seen with microsomes.

Example 15

The following example demonstrates the ability to multiplex the bioluminescent assay of the present invention, i.e., a bioluminescent assay using a derivative of 2-cyano-6-substituted benzothiazole for a non-luciferase enzyme of interest, with another bioluminescent assay, e.g., a bioluminescent assay using a derivative of D-luciferin or aminoluciferin for a non-luciferase enzyme of interest. In this example, two different P450 enzymes, CYP1A2 and CYP3A4, were detected in a single sample. For detection of CYP1A2, the 2-cyano-6-substituted benzothiazole derivative compound 3019 was used with bioluminescence detected using LDR containing D-cysteine. For detection of CYP3A4, the luciferin acetal derivative, Luciferin-IPA (Luc-IPA), was used with bioluminescence detected using LDR without D-cysteine. This multiplex assay allows for the identification of CYP1A2 and/or CYP3A4 activities from a single incubation using two different bioluminogenic substrates in a cell-based assay.

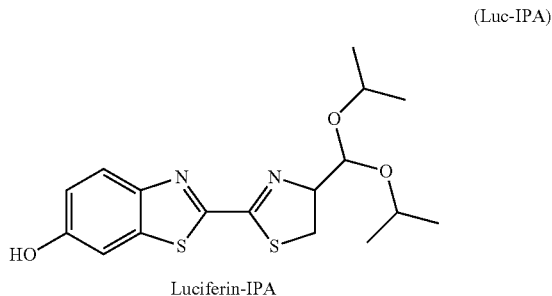 [SMILES: CC(C)OC(OC(C)C)C1CSC(c2nc3ccc(O)cc3s2)=N1]

(Luc-IPA)

Luciferin-IPA

Human cryopreserved hepatocytes (Celsis In Vitro Technologies) were thawed and seeded in hepatocyte culture medium in wells of a collagen-coated, 96-well culture plate at ~50,000 cells per well and kept at 37° C. in standard cell culture incubator with 5% $CO_2$. The cells were then treated for 48 hours with 100 µM omeprazole, 25 µM rifampicin, or vehicle control (0.1% DMSO) dissolved in hepatocytes culture medium (n=6 for each treatment, mean values and standard deviations are shown). Cells were then rinsed twice with Krebs-Henseleit (KH) buffer and incubated for 1 hour with 6 µM compound 3019, 3 mM salicylamide and a total of 0.3% DMSO in 100 µl KH buffer, 3 µM Luc-IPA, 3 mM salicylamide and a total of 0.3% DMSO in 100 µl KH buffer, or 6 µM compound 3019, 3 µM Luc-IPA, 3 mM salicylamide and a total of 0.3% DMSO in 100 µl KH buffer. The plate was then removed from the incubator. Fifty µl from each intact cell supernatant was transferred to two-set wells of a white, 96-well luminometer plate (Costar). To one set of wells, 50 µl of LDR with 4 mM D-cysteine was added, while 50 µl of LDR without D-cysteine was added to the other set. After 20 minutes at room temperature (~21° C.), bioluminescence was measured on plate reading luminometer (Veritas).

Figure 34A:
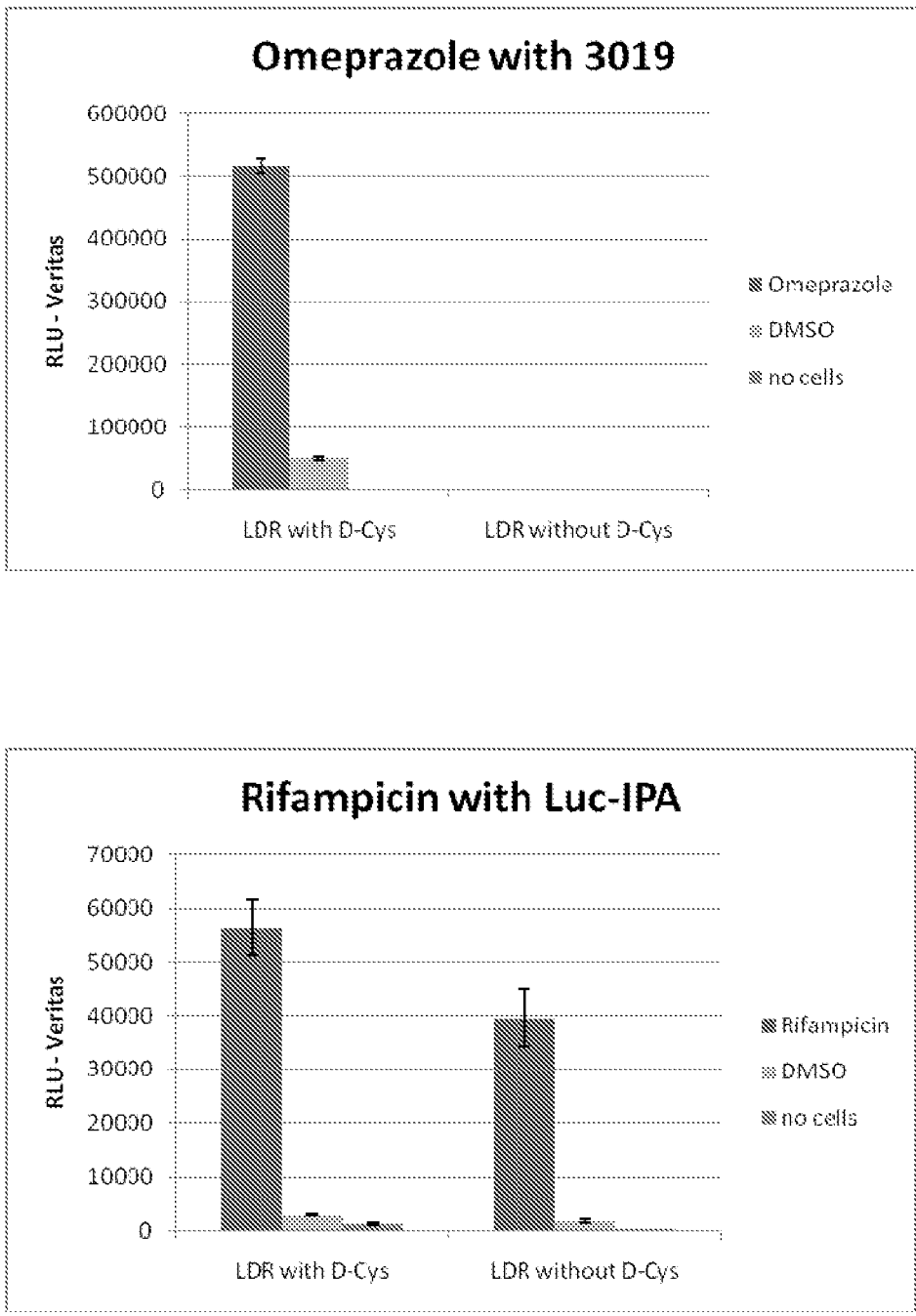
FIG. 34 illustrates data from an assay wherein two different non-luciferase enzymes, CYP1A2 and CYP3A4, are detected from a single sample.
Figure 34B:
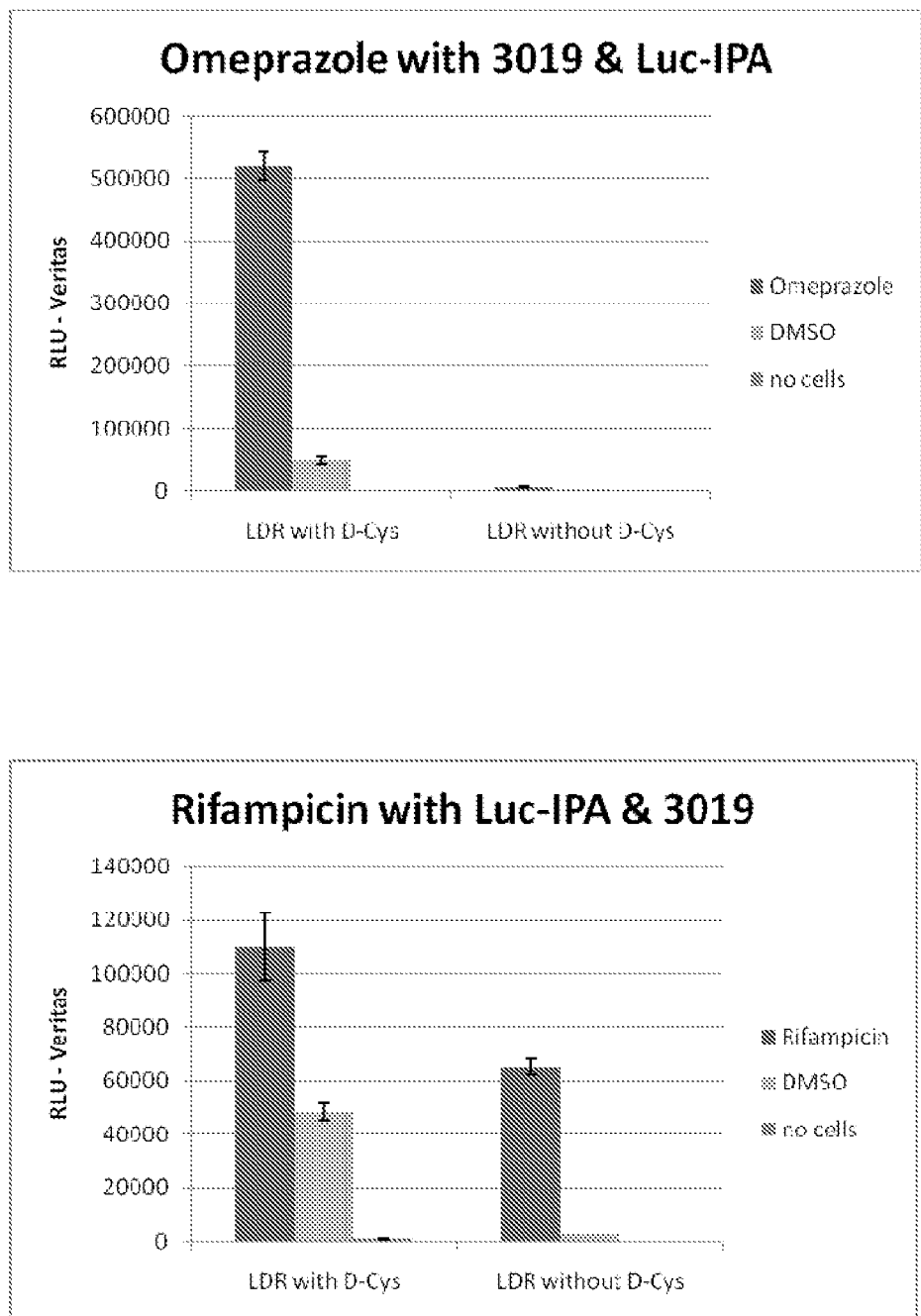

As seen in FIG. 34a-d, the method of the present invention can be performed in the presence of two bioluminescent substrates at the same time wherein one of the substrates is a derivative of 2-cyano-6-substituted benzothiazole. Omeprazole induces CYP1A and is an aryl hydrocarbon receptor (AHR) agonist. Rifampicin induces CYP3A/2C and is an PXR agonist. The "No cells" control provides a background for the substrate. FIG. 34A demonstrates induction of CYP1A2 activity by omeprazole detected using compound 3019. FIG. 34B demonstrates the induction of CYP3A4 activity by rifampicin detected using the substrate Luciferin-IPA. FIG. 34C demonstrates the induction of CYP1A2 activity by omeprazole detected using compound 3019 in the presence of the CYP3A4 substrate, Luciferin-IPA. FIG. 34D demonstrates the induction of CYP3A4 by rifampicin detected using the substrate Luciferin-IPA in the presence of CYP1A2 substrate, compound 3019.

All publications, patents, and patent documents are incorporated by reference herein, as though individually incorporated by reference. The invention has been described with reference to various specific and preferred aspects and techniques. However, it should be understood that many variations and modifications may be made while remaining within the spirit and scope of the invention.

What is claimed is:

1. An in vitro method of detecting a non-luciferase enzyme in a cell comprising:
    (a) contacting cells with a substrate for the non-luciferase enzyme, the substrate being a derivative of a 2-cyano-6-substituted benzothiazole under conditions which allow for a reaction between the enzyme and the substrate;
    (b) adding a luciferase reaction mixture to the contacted cells, wherein the luciferase reaction mixture comprises D-cysteine and a firefly luciferase; and
    (c) measuring bioluminescence.

2. The method of claim 1, wherein the derivative is a compound of formula (I)

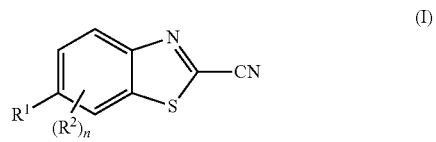

(I)

wherein
$R^1$ is H, OH, $OR^x$ or $NR^xR^y$;
$R^2$ is ($C_1$-$C_3$)alkyl, trifluoromethyl, amino, nitro, or halo;
n is 0, 1, 2, or 3;
$R^x$ is (i) ($C_1$-$C_{10}$)alkylaryl wherein the aryl is optionally substituted with one to five groups selected from the group consisting of halo, hydroxy, amino groups, amino acids, peptides and esters, or (ii) ($C_1$-$C_{10}$)alkyl, wherein the alkyl is optionally substituted with one to five groups selected from the group consisting of alkoxy, hydroxy, halo, and amino; and
$R^y$ is hydrogen or ($C_1$-$C_{10}$)alkyl.

3. The method of claim 1, wherein the derivative is selected from the group consisting of:

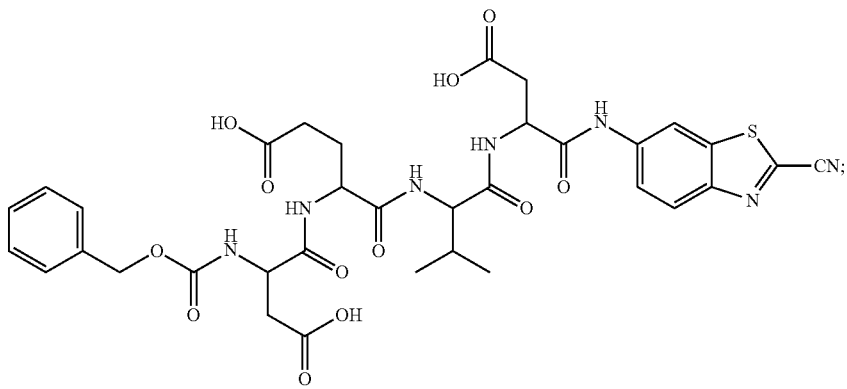

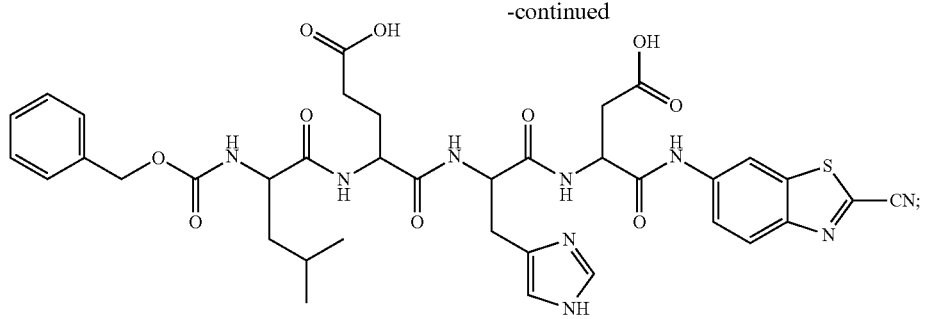
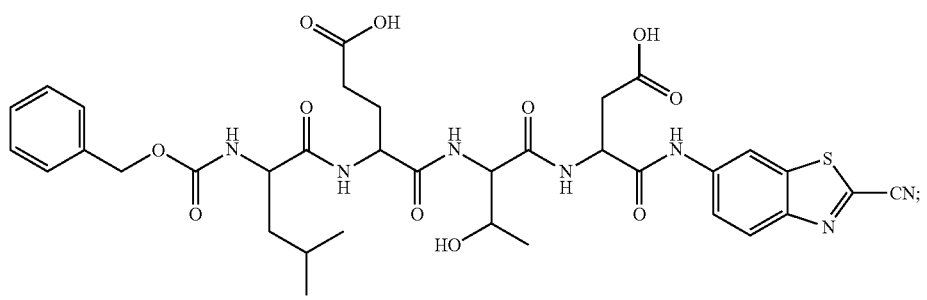
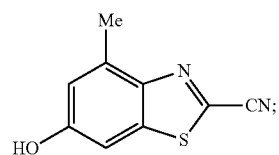
3138
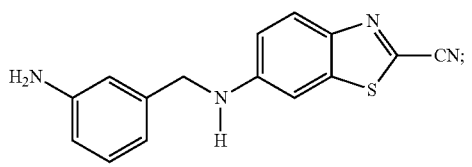
3165
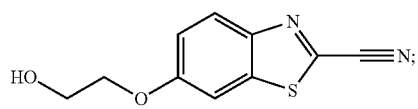
3016
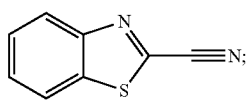
3026
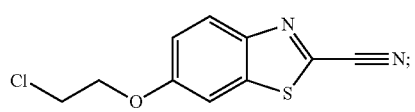
3814
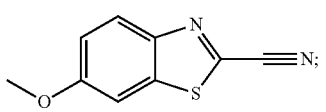
3138
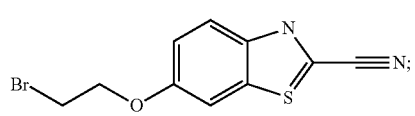
3833
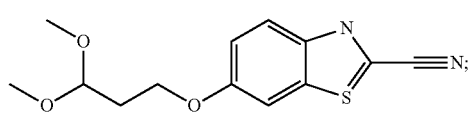
3820
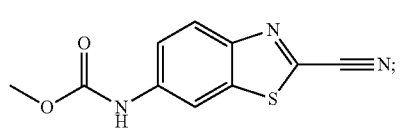
3806
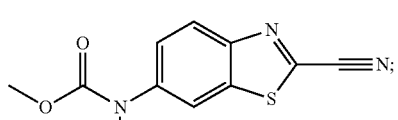
3883
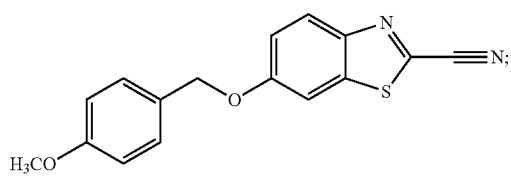
3821
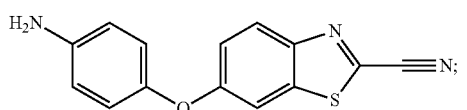
3835

-continued
3866 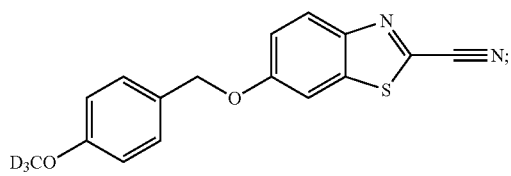
3868 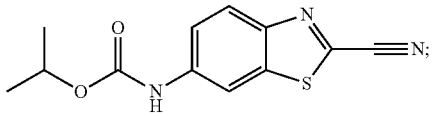
3819 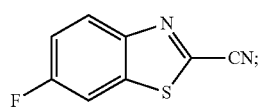
3823 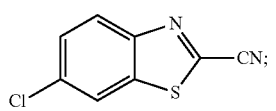
3023 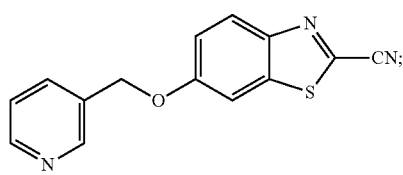
3022 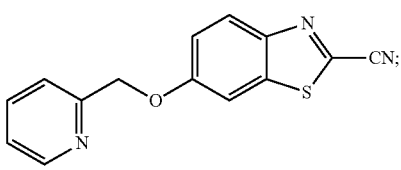
3024 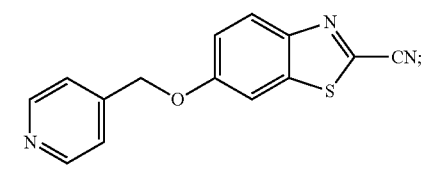
3891 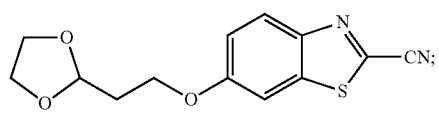
3907 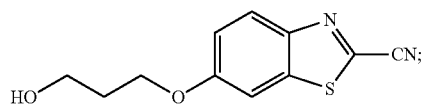
3828 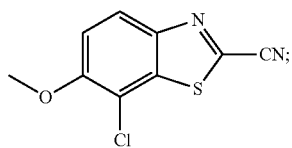
3017 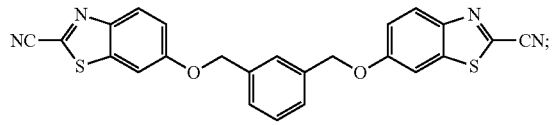
3018 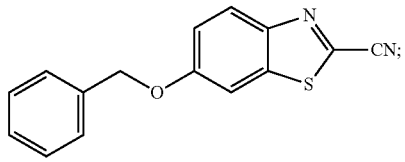
3021 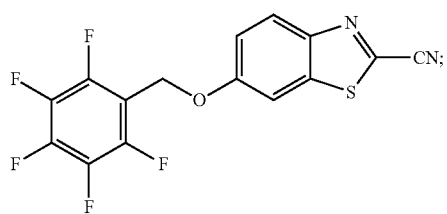
3020 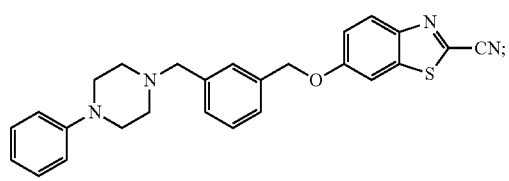

-continued

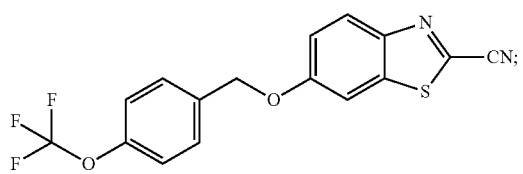
3851

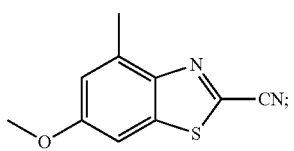
3815

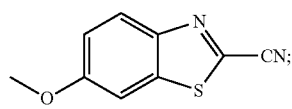
3817

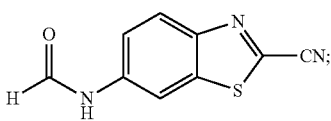
3822

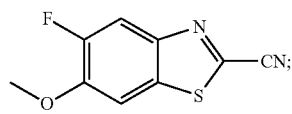
3825

3830

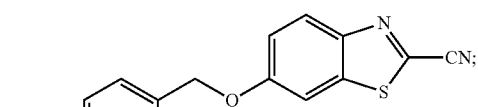
3826

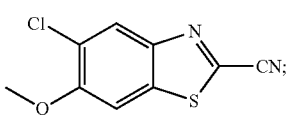
3827

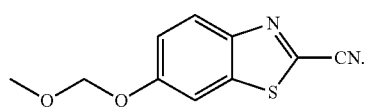
and
3829

4. The method of claim 1 wherein the non-luciferase enzyme comprises UDP glucuronosyl transferase (UGT), glutathione transferase (GST), cytochrome P450 (CYP450), flavin monoamine oxidase (FMO), histone deacetylase (HDAC), or a protease.

5. The method of claim 1, wherein the luciferase reaction mixture further comprises an esterase.

6. The method of claim 1, wherein the cells are hepatocytes.

7. The method of claim 1, wherein the cells are further contacted with a test compound prior to or simultaneously with step (a).

8. The method of claim 7, wherein the test compound is selected from the group consisting of an inhibitor of the non-luciferase enzyme, an inducer for the non-luciferase enzyme, a substrate for the non-luciferase enzyme, and an activator of the non-luciferase enzyme.

9. An in vitro method of detecting a non-luciferase enzyme in a cell comprising:
(a) contacting cells with a substrate for the non-luciferase enzyme, the substrate being a derivative of a 2-cyano-6-substituted benzothiazole, under conditions which allow for a reaction between the enzyme and the substrate, in a first reaction vessel to form an incubation mixture;
(b) transferring at least a portion of the incubation mixture to a second reaction vessel;
(c) adding a luciferase reaction mixture, wherein the luciferase reaction mixture comprises D-cysteine and a firefly luciferase, to the second reaction vessel; and
(d) measuring bioluminescence.

10. The method of claim 9, wherein the derivative is a compound of formula (I)

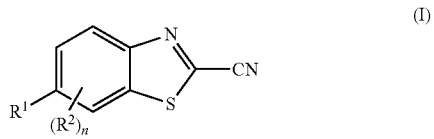

wherein $R^1$ is H, OH, $OR^x$ or $NR^xR^y$;

$R^2$ is $(C_1-C_3)$alkyl, trifluoromethyl, amino, nitro, or halo;

n is 0, 1, 2, or 3;

$R^x$ is (i) $(C_1-C_{10})$alkylaryl wherein the aryl is optionally substituted with one to five groups selected from the group consisting of halo, hydroxy, amino groups, amino acids, peptides and esters, or (ii) $(C_1-C_{10})$alkyl, wherein the alkyl is optionally substituted with one to five groups selected from the group consisting of alkoxy, hydroxy, halo, and amino; and $R^y$ is hydrogen or $(C_1-C_{10})$alkyl.

11. The method of claim 9, wherein the derivative is selected from the group consisting of:

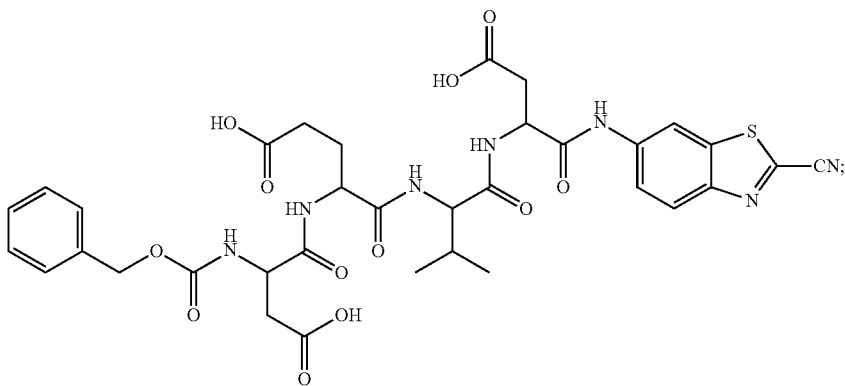
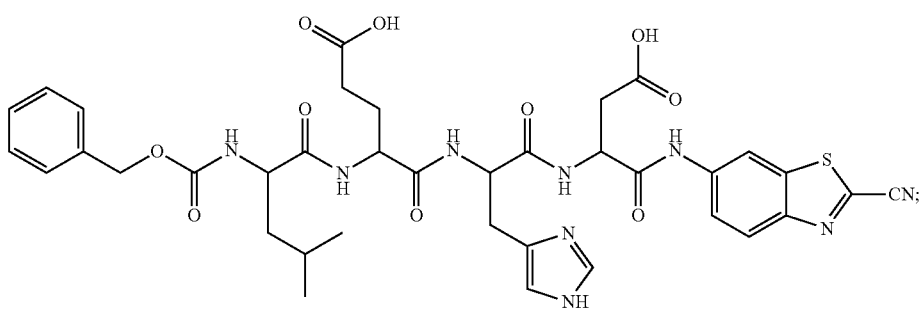
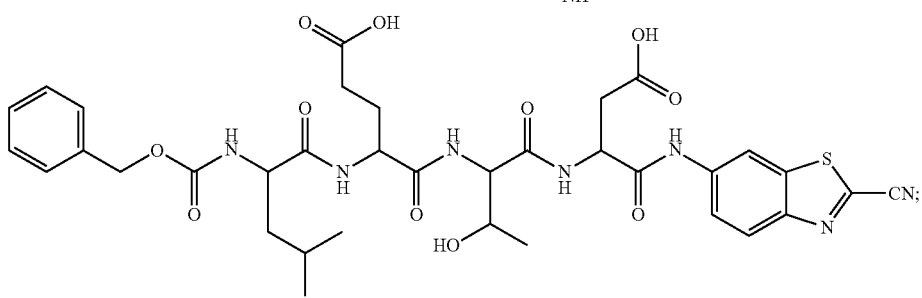
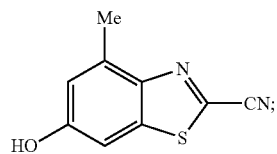
3138
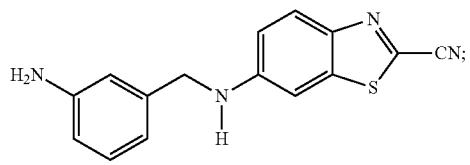
3165
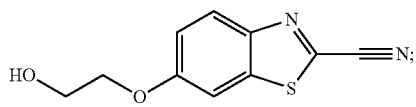
3016
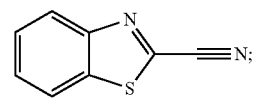
3026
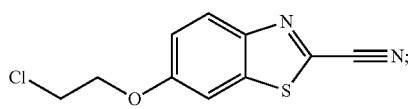
3814
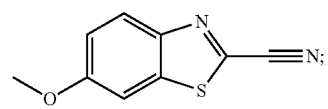
3019
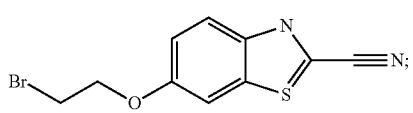
3833
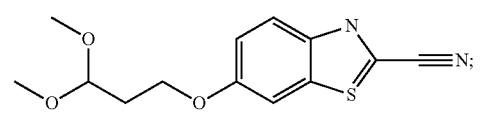
3820

-continued

12. The method of claim 9, wherein the non-luciferase enzyme comprises UGT, GST, CYP450, FMO, HDAC, or a protease.

13. The method of claim 9, wherein the luciferase reaction mixture further comprises an esterase.

14. The method of claim 9, wherein the cells are hepatocytes.

15. The method of claim 9, wherein the cells are further contacted with a test compound prior to or simultaneously with step (a).

16. The method of claim 15, wherein the test compound is selected from the group consisting of an inhibitor of the non-luciferase enzyme, an inducer for the non-luciferase enzyme, a substrate for the non-luciferase enzyme, and an activator of the non-luciferase enzyme.

17. An in vitro method of screening for modulators of a non-luciferase enzyme comprising:
(a) contacting cells with a test compound;
(b) adding a substrate for the non-luciferase enzyme, the substrate being a derivative of a 2-cyano-6-substituted benzothiazole, under conditions which allow for a reaction between the substrate and the non-luciferase enzyme, to form a mixture;
(c) adding a luciferase reaction mixture, wherein the luciferase reaction mixture comprises D-cysteine and a firefly luciferase, to the mixture; and (d) measuring bioluminescence; wherein the bioluminescence is compared to that from cells not contacted with a test compound.

18. The method of claim 17, wherein the derivative is a compound of formula (I)

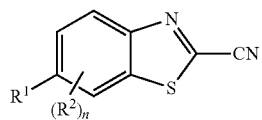

wherein
R¹ is H, OH, OR$^x$ or NR$^x$R$^y$;
R² is (C$_1$-C$_3$)alkyl, trifluoromethyl, amino, nitro, or halo;
n is 0, 1, 2, or 3;
R$^x$ is (i) (C$_1$-C$_{10}$)alkylaryl wherein the aryl is optionally substituted with one to five groups selected from the group consisting of halo, hydroxy, amino groups, amino acids, peptides and esters, or (ii) (C$_1$-C$_{10}$)alkyl, wherein the alkyl is optionally substituted with one to five groups selected from the group consisting of alkoxy, hydroxy, halo, and amino; and
R$^y$ is hydrogen or (C$_1$-C$_{10}$)alkyl.

19. The method of claim 17, wherein the derivative is selected from the group consisting of:

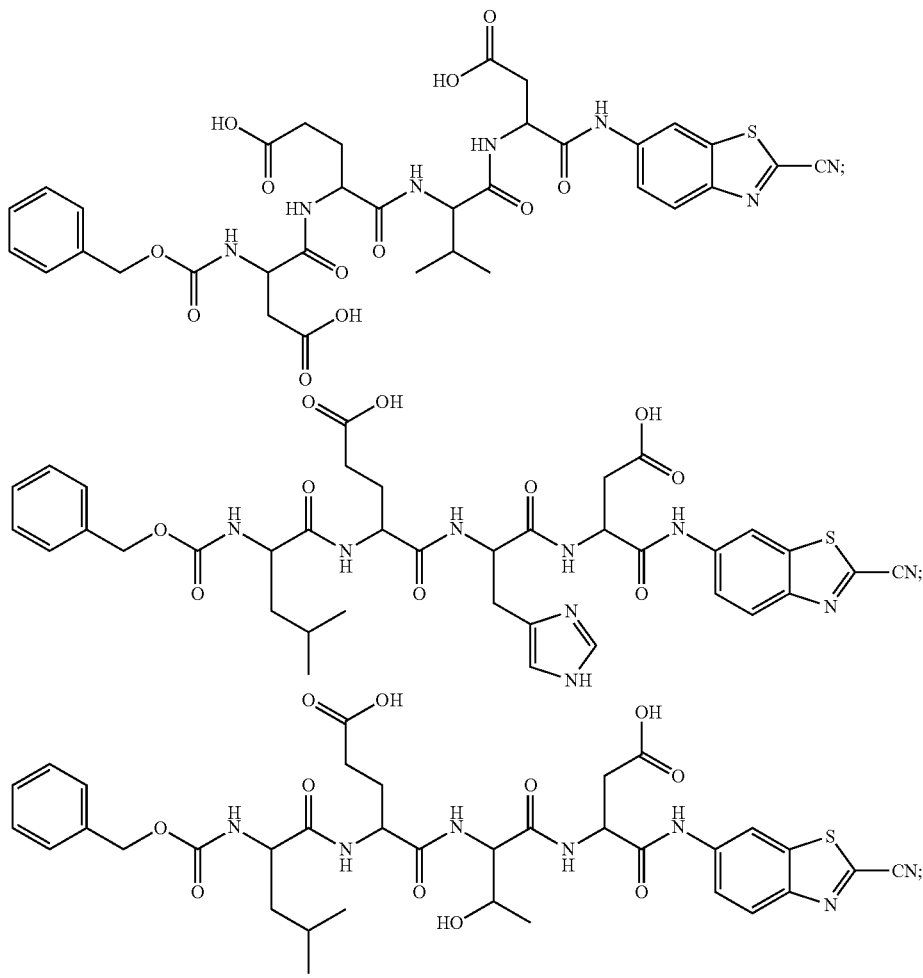

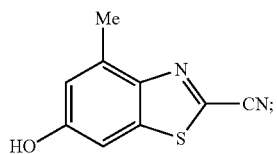

3138

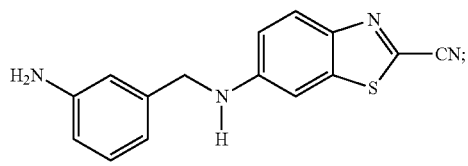

3165

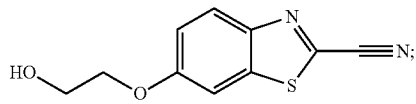

3016

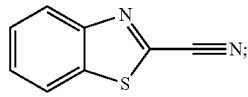

3026

-continued

-continued

3017
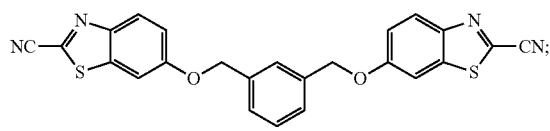

3018
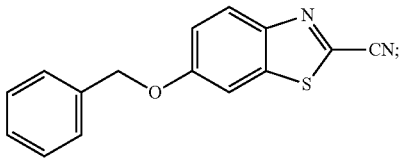

3021
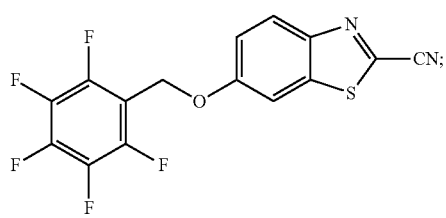

3020
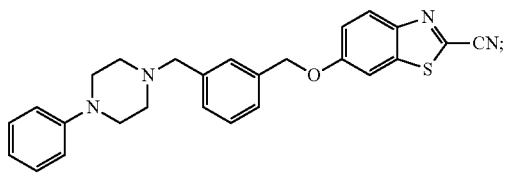

3851
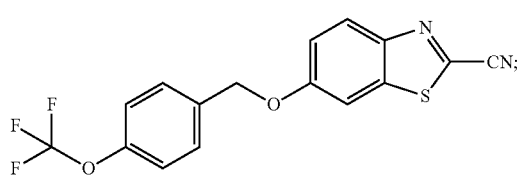

3815
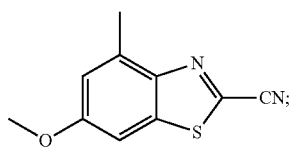

3817
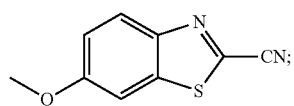

3822
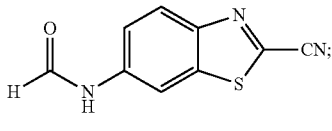

3825
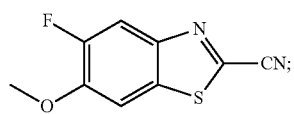

3830

3826
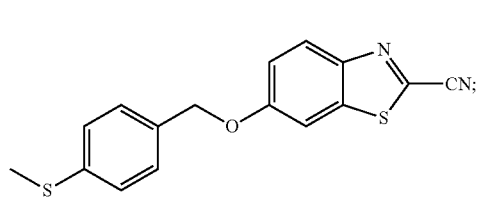

3827
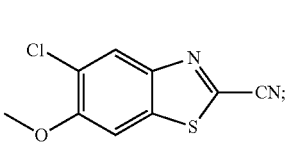

and

3829
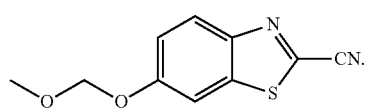

20. The method of claim 17, wherein the non-luciferase enzyme comprises UGT, GST, CYP450, FMO, HDAC, or a protease.

21. The method of claim 17, wherein the luciferase reaction mixture further comprises an esterase.

22. The method of claim 17, wherein the cells are hepatocytes.

23. An in vitro method of detecting more than one non-luciferase enzyme in a cell comprising:

a) contacting cells with more than one bioluminogenic substrate wherein one of the substrates is a derivative of a 2-cyano-6-substituted benzothiazole under conditions which allow for a reaction between the enzymes and the substrates in a first reaction vessel to form a reaction mixture;

b) transferring a portion of the incubation mixture to a second and third reaction vessel;

c) adding to one of the reaction vessels a luciferase reaction mixture comprising D-cysteine and a firefly luciferase and adding to the other reaction vessel luciferase reaction mixture comprising a firefly luciferase without D-cysteine; and d) measuring bioluminescence in both reaction vessels.

24. The method of claim 23, wherein the derivative is a compound of formula (I)

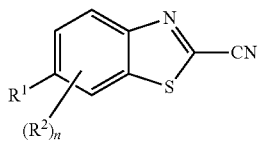

(I)

wherein $R^1$ is H, OH, $OR^x$ or $NR^xR^y$;

$R^2$ is ($C_1$-$C_3$)alkyl, trifluoromethyl, amino, nitro, or halo;

n is 0, 1, 2, or 3;

$R^x$ is (i) ($C_1$-$C_{10}$)alkylaryl wherein the aryl is optionally substituted with one to five groups selected from the group consisting of halo, hydroxy, amino groups, amino acids, peptides and esters, or (ii) ($C_1$-$C_{10}$)alkyl, wherein the alkyl is optionally substituted with one to five groups selected from the group consisting of alkoxy, hydroxy, halo, and amino; and $R^y$ is hydrogen or ($C_1$-$C_{10}$)alkyl.

25. The method of claim 23, wherein the derivative is selected from the group consisting of:

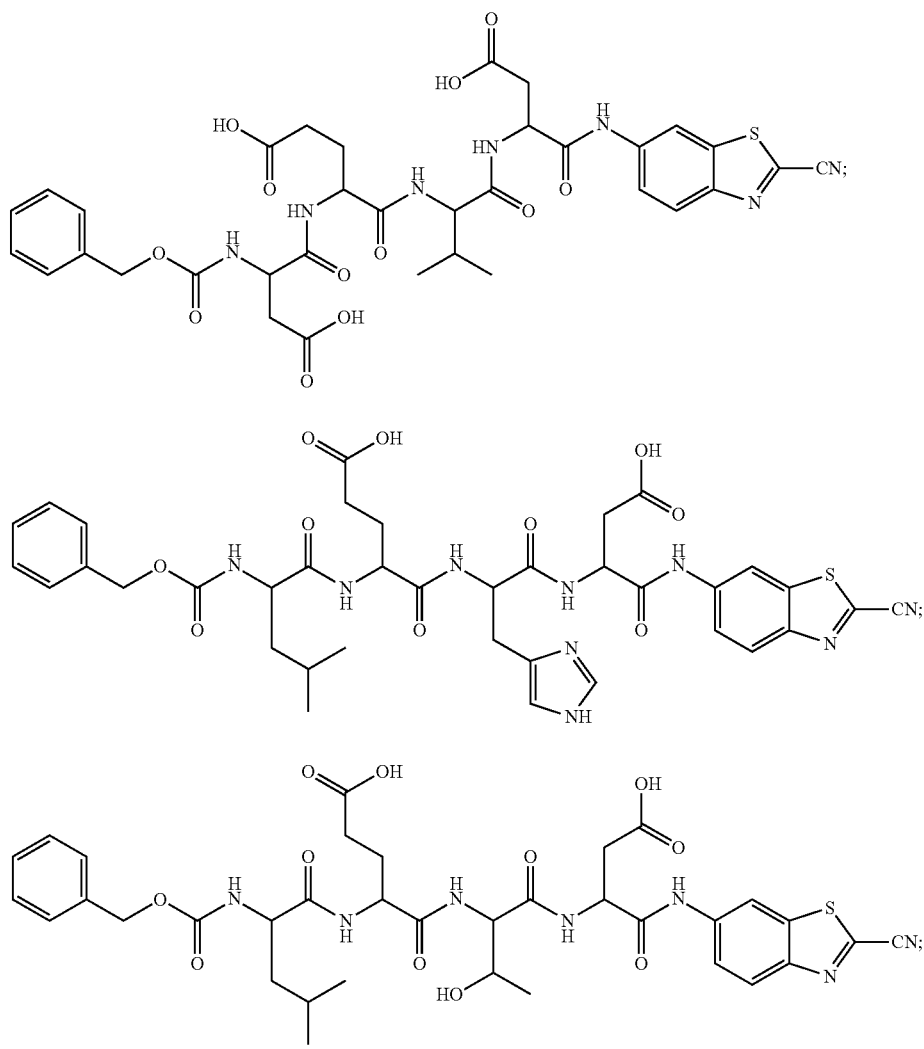

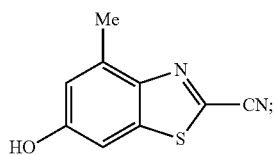

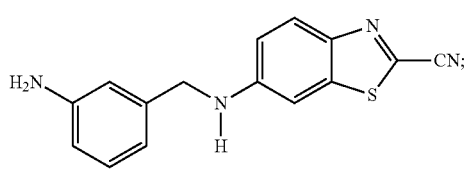

-continued
| | | | |
|---|---|---|---|
| 3016 | 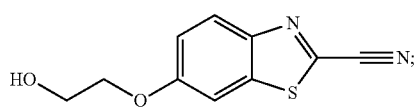 | 3026 | 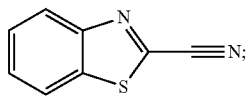 |
| 3814 | 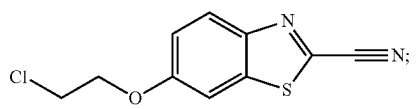 | 3138 | 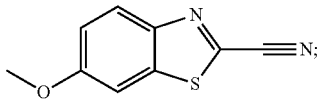 |
| 3833 | 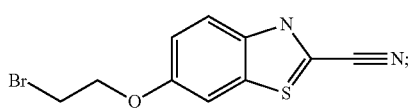 | 3820 | 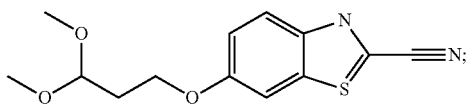 |
| 3806 | 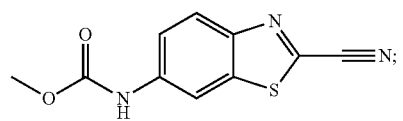 | 3883 | 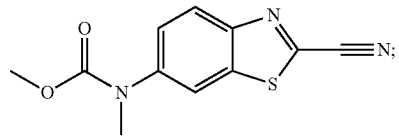 |
| 3821 | 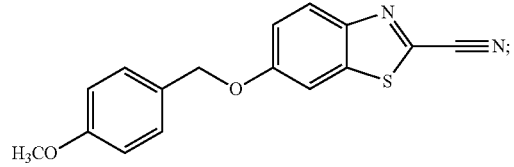 | 3835 | 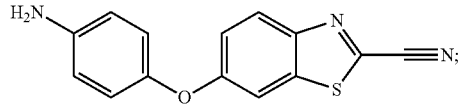 |
| 3866 | 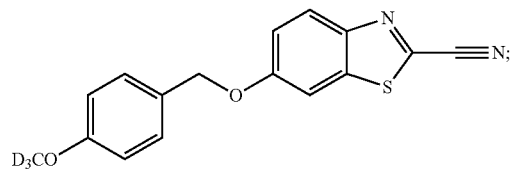 | 3868 | 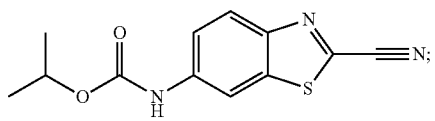 |
| 3819 | 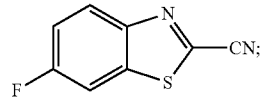 | 3823 | 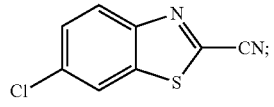 |
| 3023 | 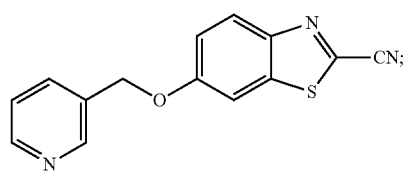 | 3022 | 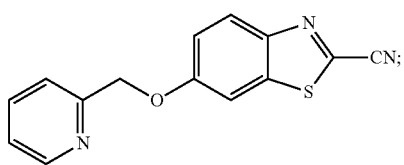 |
| 3024 | 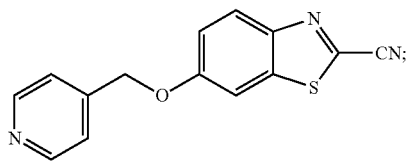 | 3891 | 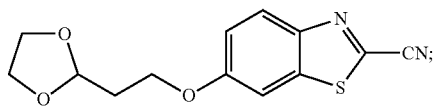 |

-continued

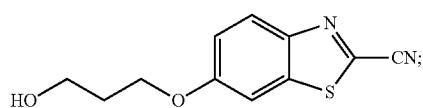
3907

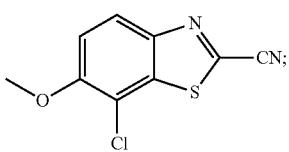
3828

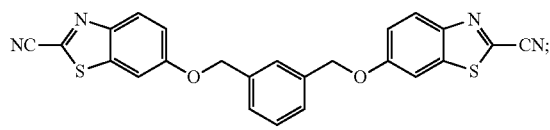
3017

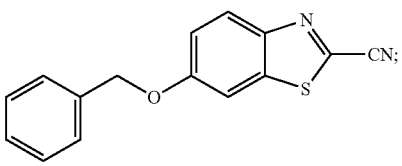
3018

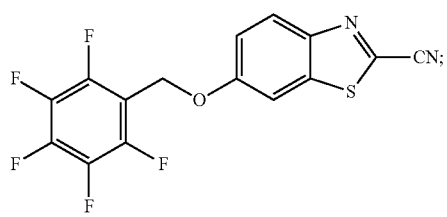
3021

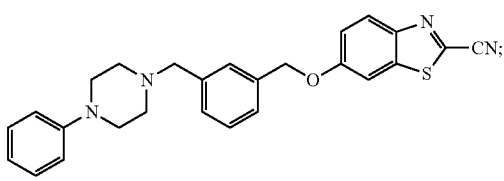
3020

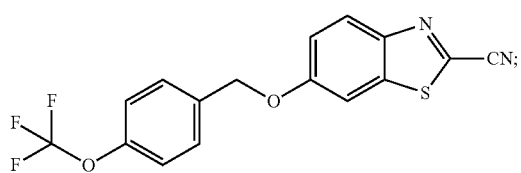
3851

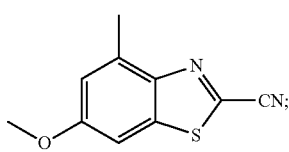
3815

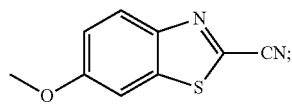
3817

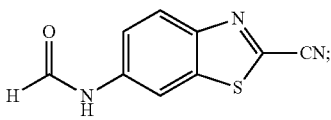
3822

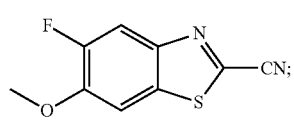
3825

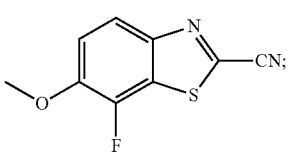
3830

3826

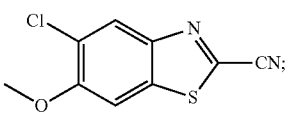
3827

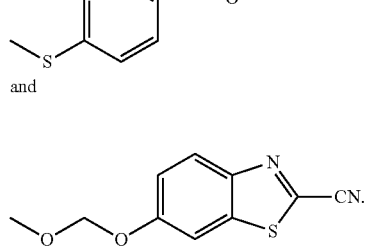
and

3829

26. The method of claim 23, wherein the non-luciferase enzyme comprises UGT, GST, CYP450, FMO, HDAC, or a protease.

27. The method of claim 23, wherein the luciferase reaction mixture further comprises an esterase.

28. The method of claim 23, wherein the cells are hepatocytes.

29. The method of claim 23, wherein the cells are further contacted with a test compound prior to or simultaneously with step (a).

30. The method of claim 23, wherein the other bioluminogenic substrate is a derivative of D-luciferin or aminoluciferin.

* * * * *